US012776394B2

(12) United States Patent
Croquette et al.

(10) Patent No.: US 12,776,394 B2
(45) Date of Patent: Oct. 27, 2026

(54) SIMULACRUM LABWARE SUBSTITUTES AND METHODS THEREFOR

(71) Applicant: Azenta, Inc., Burlington, MA (US)

(72) Inventors: Etienne P. Croquette, Cheshire (GB); Robin Grimwood, Chelford (GB); David Andrew Harding, Lanchashire (GB)

(73) Assignee: Azenta, Inc., Burlington, MA (US)

( * ) Notice: Subject to any disclaimer, the term of this patent is extended or adjusted under 35 U.S.C. 154(b) by 730 days.

(21) Appl. No.: 17/819,179

(22) Filed: Aug. 11, 2022

(65) Prior Publication Data

US 2023/0052944 A1 Feb. 16, 2023

Related U.S. Application Data

(60) Provisional application No. 63/232,971, filed on Aug. 13, 2021.

(51) Int. Cl.
*G16H 10/40* (2018.01)
*G05B 19/4155* (2006.01)

(52) U.S. Cl.
CPC ......... *G16H 10/40* (2018.01); *G05B 19/4155* (2013.01); *G05B 2219/50333* (2013.01)

(58) Field of Classification Search
CPC .................. G16H 1/40; G05B 19/4155; G05B 2219/50333
See application file for complete search history.

(56) References Cited

U.S. PATENT DOCUMENTS

| | | | | |
|---|---|---|---|---|
| 4,969,336 | A | 11/1990 | Knippscheer et al. | |
| 8,252,232 | B2 | 8/2012 | Neeper et al. | |
| 10,897,892 | B1 * | 1/2021 | Sole | A01N 1/162 |
| 11,478,785 | B2 | 10/2022 | Fitzer et al. | |
| 2018/0202908 | A1 | 7/2018 | Croquette et al. | |
| 2019/0293344 | A1 | 9/2019 | Sun et al. | |

OTHER PUBLICATIONS

International Search Report, International Application No. PCT/US2022/074916 dated Jan. 18, 2023.

* cited by examiner

*Primary Examiner* — Jerry-Daryl Fletcher
*Assistant Examiner* — Keith Stanley Myers
(74) *Attorney, Agent, or Firm* — Perman & Green, LLP

(57) ABSTRACT

A temperature controlled sample specimen laboratory storage system, for storing sample specimens disposed in one or more of labware units and labware devices, includes a refrigerated chamber with a storage array therein having predetermined storage locations defining a predetermined capacity of one or more of labware unit storage and labware device storage of the storage array, where the storage array has a predetermined area, and at least one simulacrum labware substitute having a predetermined characteristic that simulates a corresponding one of the one or more of the labware units and labware devices. The at least one simulacrum labware substitute is disposed within the storage array so that the predetermined capacity of the one or more of the labware unit storage and the labware device storage of the storage array, of predetermined area, is unconstrained by the at least one simulacrum labware substitute held in the storage location.

32 Claims, 33 Drawing Sheets

SIMULACRUM LABWARE SUBSTITUTES AND METHODS THEREFOR

CROSS-REFERENCE TO RELATED APPLICATIONS

This application is a non-provisional of and claims the benefit of U.S. provisional patent application No. 63/232,971 filed on Aug. 13, 2021, the disclosure of which is incorporated herein by reference in its entirety.

BACKGROUND

1. Field

The exemplary embodiments generally relate to automated sample stores, and more particularly, to labware handled by the automated sample stores.

2. Brief Description of Related Developments

Cold storage via, for example, freezers, ultra-low freezers, and cryogenic freezers is essential to maintaining the integrity of biological substances over extended periods of storage. At sufficiently low temperatures, all chemical processes and biological functions of such substances are effectively halted, allowing them to be stored safely over nearly any length of time. A storage freezer enables such storage by providing an insulated and temperature controlled environment to accommodate a number of biological or other samples which are held in individual vials/containers or cassettes. In typical storage freezers, the samples held in the individual vials/containers or cassettes are loaded into racks, trays, or boxes, each of which holds several samples. Generally the time between sample collection and freezing of the sample affects a quality of the sample and as such, some research and analysis facilities set prescribed times with which a collected sample is to be frozen.

BRIEF DESCRIPTION OF THE DRAWINGS

The foregoing aspects and other features of the present disclosure are explained in the following description, taken in connection with the accompanying drawings, wherein.

DETAILED DESCRIPTION

Figure 1A:
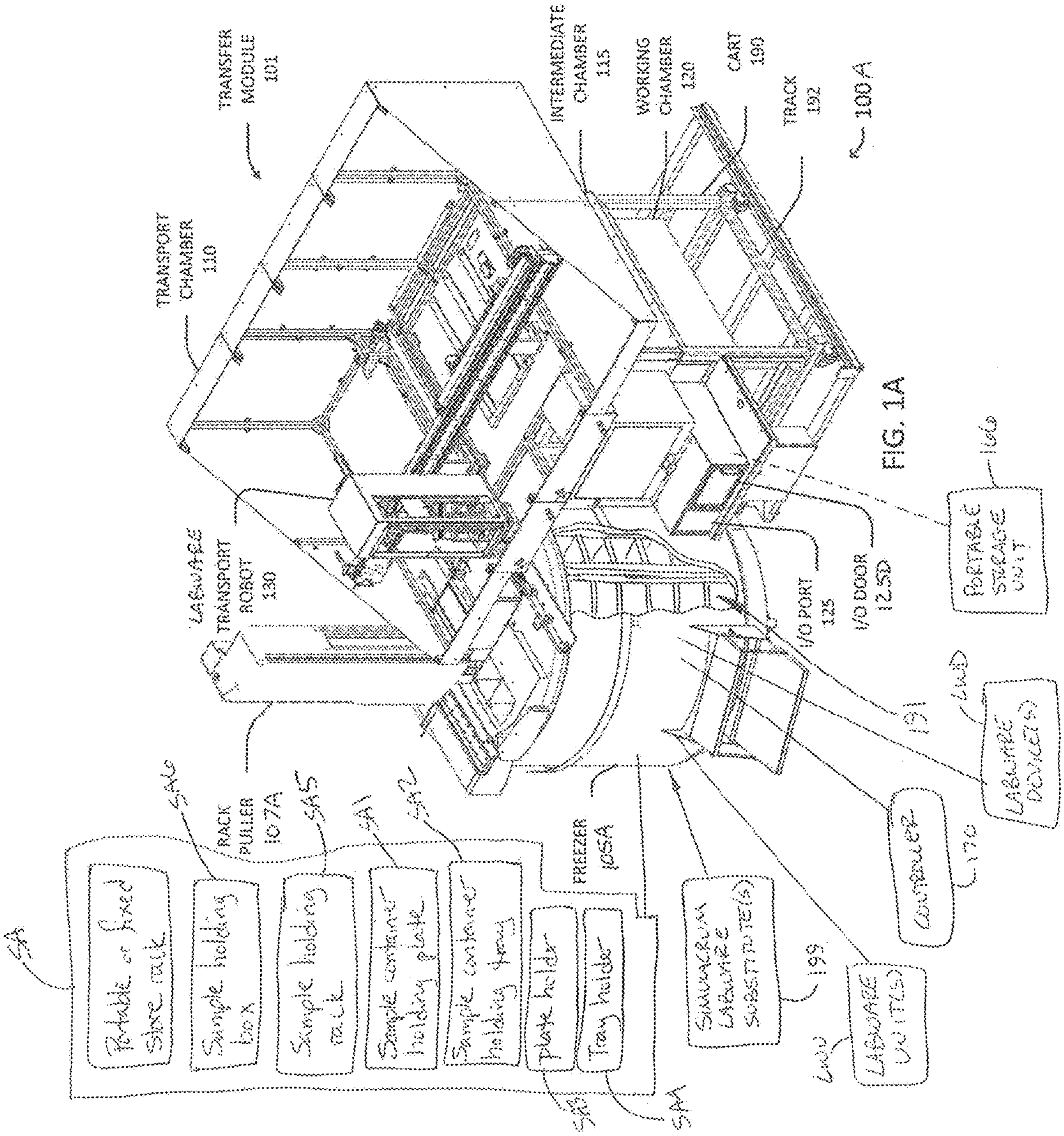
FIG. 1A is a schematic perspective illustration of an automated temperature controlled sample specimen laboratory storage system incorporating aspects of the present disclosure.
Figure 2A:
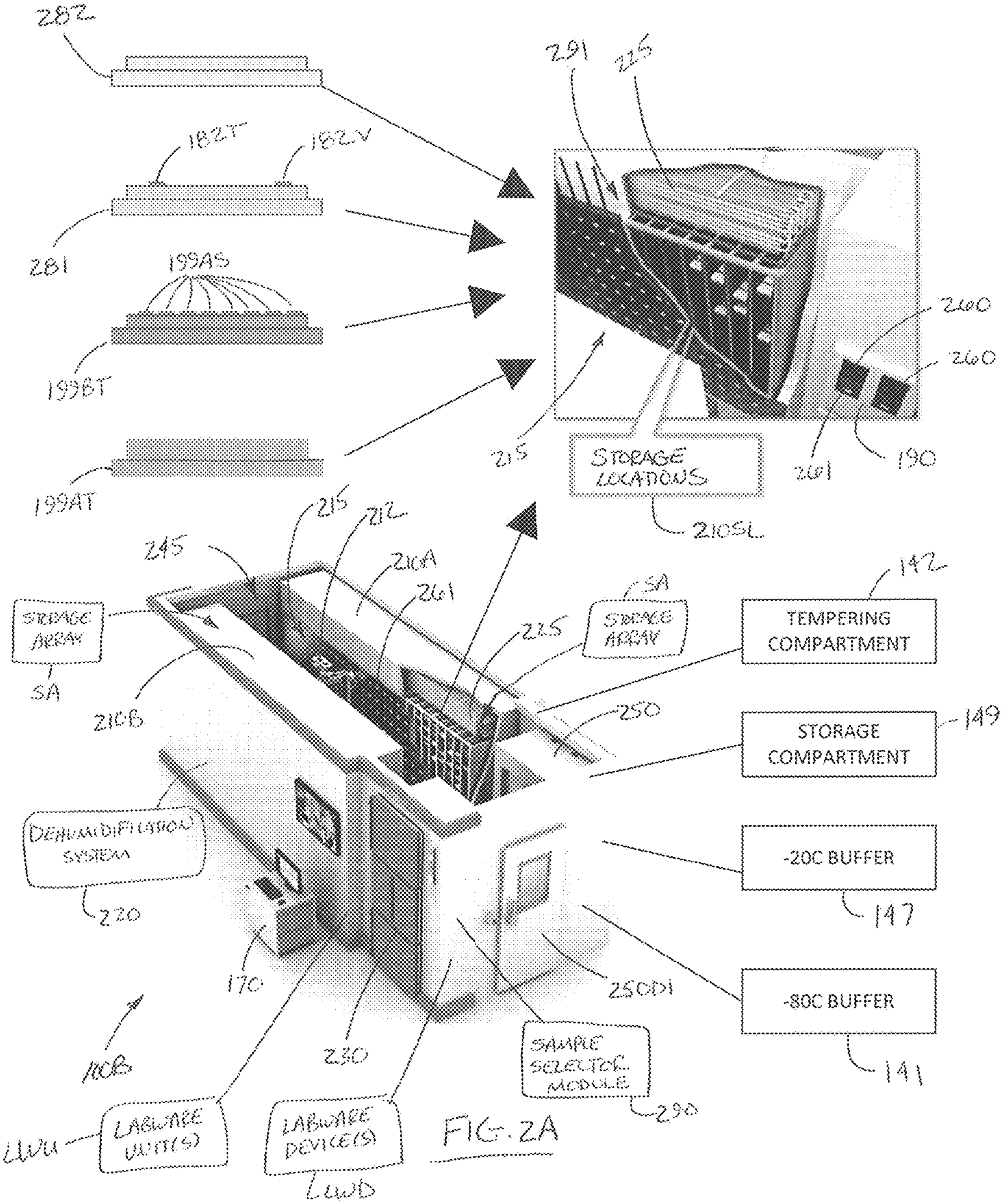
FIG. 2A is a schematic perspective illustration of an automated temperature controlled sample specimen laboratory storage system incorporating aspects of the present disclosure.

FIGS. 1A and 2A illustrate exemplary automated temperature controlled sample specimen laboratory storage systems 100A, 100B (referred to herein as "stores") in accordance with aspects of the present disclosure. Although the aspects of the present disclosure will be described with reference to the drawings, it should be understood that the aspects of the present disclosure can be embodied in many forms. In addition, any suitable size, shape or type of elements or materials could be used.

In some instances sample stores used to store or bank samples, when put in service, have few samples stored therein and as such have a low capacity or low thermal inertia resulting in thermal variations in the store or bank and disruptions/instability to the thermal equilibrium throughout the store or bank with commensurate results that may affect the quality of the samples placed therein. In other instances, samples are placed in a sparsely populated area of the store (whether new to service or not). These partially filled stores and/or sparsely populated areas of the stores may also have poor temperature uniformity and stability (i.e., temperature gradients within the store or within a section of the store) as a result of the low thermal inertia of the store or of a section of the store.

The same or similar low thermal inertia applies to sample storage trays and a position of the sample in a sample storage tray. For example, samples that are isolated on sample storage trays, apart from other samples, (and subject to the low thermal inertia of the sample store) may have an increased time to freeze. Similarly, sample storage trays that have been in a room temperature and holding warm or newly acquired/harvested samples may also impede freezing of the samples when the samples are placed in the store.

In accordance with the aspects of the present disclosure the stores 100A, 100B are configured to store one or more of sample specimens that are disposed in one or more labware units LWU (i.e., sample tubes 182 (FIG. 7), sample cassettes 477, or other container for holding an individual sample) and labware devices LWD that are configured to hold the labware units (e.g., trays, racks, boxes, or any other suitable container for collectively holding a predetermined number of labware units). These labware units LWU and labware devices LWD are referred to as "active labware" herein, as will be described below. The stores 100A, 100B are also configured to hold and are filled with simulacrum labware (units/devices) substitutes 199 (which may be in a form corresponding to an active labware unit or an active labware device which include but are not limited to tissue cassettes, vials, multi-well plates, frames for holding bags (e.g., such as blood bags), racks, or any other suitable labware). The simulacrum labware substitutes 199 are configured so as to substitute active labware disposed in the store 100A, 100B so that a predetermined store 100A, 100B capacity is unconstrained by simulacrum labware substitute 199 storage within the store 100A, 100B or other predetermined storage part of the store 100A, 100B. The simulacrum labware substitutes 199 disposition within the store 100A, 100B is unrestricted/unconstrained and maintains a predetermined storage capacity as a maximum storage capacity of the store 100A, 100B (or other predetermined storage part of the store 100A, 100B).

As will be described in greater detail herein, the simulacrum labware substitutes 199 each have a predetermined characteristic that simulates (i.e., is commensurate with, consistent with, or substantially coincides with) a predetermined characteristic of the active labware. The active labware being labware that is active in, engaged in, and/or effects laboratory functions. In one or more aspects, the active labware is cooled process-ware that effects a cooled process and that is stored cooled for preserving an in process temperature of the samples held in the active labware. It is noted that while labware for cold storage environments are referred to herein, the simulacrum labware substitutes 199 may be any suitable process-ware employed in any suitable storage environments.

The predetermined characteristic of the simulacrum labware substitute 199, that simulates the predetermined characteristic of active labware, includes one or more of (but is not limited to) a size and shape (i.e., form factor) of the simulacrum labware substitute 199. For example, the size and shape of the simulacrum labware substitute 199 simulates (i.e., is commensurate with, consistent with, or substantially coincides with) a size and shape of a corresponding active labware so as to be transported with store 100A, 100B automation in the same manner as the active labware, and held in the same locations in the same manner as the active labware.

In accordance with the aspects of the present disclosure, the store 100A, 100B having its storage area(s) filled with the simulacrum labware substitutes 199 (or having the simulacrum labware substitutes fill area(s) of store 100A, 100B storage areas not occupied by active labware) maintains a substantially steady state or substantially uniform temperature distribution (with refrigeration on or off) within the storage area(s) regardless of whether the storage areas are filled to a predetermined maximum capacity with the active labware (i.e., the predetermined capacity of the one or more of the labware unit storage and the labware device storage of the storage array SA remains a maximum capacity independent of the at least one simulacrum labware substitute(s) 199 held in a storage location(s) 186, 210SL (see FIGS. 1F and 2A) of the storage array SA). For example, a store 100A, 100B having a storage area filled with active labware units LWU to a capacity that is less than a maximum capacity of the storage area (i.e., as little as one active labware within the storage area with the storage areas not holding active labware being referred to as "empty" storage areas) is maintained at a substantially steady state or substantially uniform temperature profile, throughout the storage area (with refrigeration or without refrigeration), by the simulacrum labware substitutes 199 within the storage area (e.g., stored in the "empty" storage areas in place of the active labware), invariant of a location and quantity of active labware units LWU in the storage area. Here, the store capacity of the storage area is unrestrained/unconstrained (i.e., independent or decoupled) from thermal maintenance of the storage area. In accordance with aspects of the present disclosure, the storage array SA within a refrigerated chamber (as described herein) of the stores 100A, 100B is at least one from (1) a sample container holding plate SA1 (e.g., a multi-well plate), (2) a sample (e.g., vial/tube 182, or cassette 477) container holding tray SA2 (e.g., trays 281, 372—FIGS. 2A and 2C), (3) a plate holder SA3 (configured to hold one or more multi-well plates), (4) a tray holder SA4 (configured to hold one or more container holding trays), (5) a sample holding rack SA5 (such as storage rack 185—FIG. 1F), (6) a sample holding box SA6 (such as sample box 180A, 180B—FIG. 1F), and (7) a portable or fixed store rack SA7 (such as fixed 291, carousel type storage racks 191, and portable storage racks 370, 371—FIGS. 1A, 2A, and 2C) disposed for holding one or more of a sample container holding plate SA1, a sample container holding tray SA2, a plate holder SA3, a tray holder SA4, a sample holding rack SA5, and a sample holding box SA6 in stored array.

As will be understood from the description herein, the aspects of the present disclosure address the time it takes to cool/freeze a biological sample (referred to herein generally as a "sample"), contained in an active labware unit, and also the low thermal inertia of sample stores, such as stores 100A, 100B affecting storage of samples. The aspects of the present disclosure provide for a reduction of exposure to higher temperatures for samples stored in the stores 100A, 100B when compared to exposure durations to higher temperatures of samples in newly stored or sparsely populated stores and/or sample holding labware of conventional systems. The aspects of the present disclosure also provide for increased uniformity (substantially uniform distribution or substantially steady state distribution) of temperature within stores 100A, 100B (e.g., substantially eliminates temperature gradients, across distance/areas, caused by unpopulated areas of a store 100A, 100B or sample holding labware). The aspects of the present disclosure provide for a deceleration of a temperature warm-up curve (as described herein) or a thermal inertial bias sustaining thermal equilibrium in case of refrigeration and/or power failure to the store 100A, 100B that would otherwise occur in a sparsely populated store or sparsely populated sample tray. For example, the aspects of the present disclosure provide for a longer "free wheel" phase of the store 100A, 100B with refrigeration units of the store 100A, 100B turned off or inoperable (i.e., the aspects of the present disclosure increase the thermal mass of the store 100A, 100B so that the store 100A, 100B resists increases in temperature or non-steady state temperature fluctuations in general). Here, a reduction in power consumption of the store 100A, 100B may also be realized through employment of the aspects of the present disclosure as increased thermal mass of store 100A, 100B may facilitate a reduced operational time of the refrigeration units.

The aspects of the present disclosure may also decrease the time it takes for a newly acquired/harvested sample to freeze. For example, the increased thermal mass of the store 100A, 100B and/or an increased thermal mass of sample holding labware may decrease exposure of the samples to temperatures higher than (i.e., temperatures exterior to) those temperatures within the store. The increased thermal mass of the store 100A, 100B and/or increased thermal mass of sample holding labware may increase exposure of the samples to a more uniform temperature within the store 100A, 100B.

The aspects of the present disclosure increase the thermal inertia of the store 100A, 100B at both a sample holding labware level and at a store level (compared to a thermal inertia of conventional automated sample stores with conventional sample storage trays configured for automated handling therein), to minimize sample temperature variations within the store 100A, 100B and to reduce a warm-up rate of the samples in the case of a power or refrigeration failure. For example, the aspects of the present disclosure maximize the thermal mass around samples to slow down sample warm-up rates and store 100A, 100B warm-up rates.

Still referring to FIG. 1A and also to FIGS. 1B-1F, in one or more aspects, the store 100A is an automated cryogenic storage system. The store 100A, which includes a transfer module 101, a freezer 105A (also referred to as a refrigerated chamber), and a rack puller 107A. The freezer 105A is a storage area that maintains a cryogenic environment for storing multiple samples, such as sample tubes 182A, 182B assembled in sample boxes 180A, 180B (FIG. 1F) or any other suitable sample holding labware (i.e., "active labware") as described herein. In one or more aspects, the freezer 105A is configured to store samples in an "ultra-cold" environment of about −80° C. or less; while in other aspects the freezer 105A is configured to store samples in a "cold" environment of about −20° C.; while in yet other aspects the freezer 105A is configured to store samples in a "low" temperature environment of less than 0° C. The samples are stored within the freezer 105A in predetermined storage locations, such as defined by the storage locations (e.g., rack slots 186, also referred to as storage locations 186) of storage racks 185 held within the freezer 105*a* (see FIG. 1F). These storage racks 185 are configured to hold at least one of the active labware unit and/or at least one of the active labware device per storage location at a refrigerated thermal equilibrium. Here, the number of storage locations 186 define a predetermined (maximum) capacity of active labware unit and/or active labware device storage of the storage array SA formed by a predetermined (maximum) number of the storage racks 185 within the freezer 105A. In accordance with the present disclosure, the freezer 105A is a cylindrical vessel; however, the freezer can have any shape such as, for example, a rectangular box, such as illustrated in FIG. 2A (which will be described in greater detail below). In one or more aspects, the freezer 105A includes an external wall or shell separated from an inner wall or shell by a vacuum insulated space (e.g., a dewar vessel). The rack puller 107A is mounted to the top of the freezer 105A, and operates to raise a selected storage rack 185 (FIG. 1F) from the freezer 105A. Once raised, an active labware can be added or removed from the storage rack 185, and the rack puller 107A may then replace the storage rack 185 into the freezer 105A. In other aspects, the rack puller 107A may be disposed below the freezer 105A and operate to lower a selected storage rack 185 from the freezer 105A. In still other aspects, the rack puller 107A is mounted to the transfer module 101, and the rack puller 107A is selectively positioned to operate with the freezer 105A as well as one or more other freezers (not shown). Suitable examples of freezers and rack pullers that may be implemented in the store 100A are described in U.S. Pat. No. 10,421,607 (titled "Cryogenic Freezer") issued on Sep. 24, 2019 and 10,336,539 (titled ("Automated Cryogenic Storage System") issued on Jul. 2, 2019, the disclosures of which are incorporated herein by reference in their entireties.

The active labware device is a portable labware unit holder for at least one labware unit. For example, the active labware device is portable to and from the storage array SA and insertable into and removable from each storage location (e.g., holding location 800 of a tray/rack—FIGS. 2D and 2E; rack slot 186 of Rack 185, storage location 210SL of storage rack 291; etc.) of the storage array SA, and is at least one from (1) the sample container holding plate SA1 (e.g., a multi-well plate), (2) the sample (e.g., vial/tube 182, or cassette 477) container holding tray SA2 (e.g., trays 281 and 372—FIGS. 2A and 2C), (3) the plate holder SA3 (configured to hold one or more multi-well plates), (4) the tray holder SA4 (configured to hold one or more container holding trays), (5) the sample holding rack SA5 (such as storage rack 185—FIG. 1F), (6) the sample holding box SA6 (such as sample box 180A, 180B—FIG. 1F), and (7) the portable store rack SA7 (such as tray/plate racks 370, 371—FIGS. 1A and 2A) disposed for holding one or more of a sample container holding plate SA1, a sample container holding tray SA2, a plate holder SA3, a tray holder SA4, a sample holding rack SA5, and a sample holding box SA6 in stored array within the rack and insertable into and removable from store rack storage locations arrayed in the refrigerated chamber(s) described herein. The active labware unit is a portable specimen sample container (and is, in some embodiments, a sample container of unitary construction). For example, the active labware unit is at least one from a vial 182V, tube 182T (see FIG. 2A where the vial 182V and tube 182T are collectively referred to as sample tubes 182), a cassette 477 (FIG. 4), and a multi-well plate (inclusive of microwell plates) 282 (FIG. 2A).

The transfer module 101 operates to transfer active labware, as well as individual sample tubes, between locations while maintaining those samples below a respective glass transition temperature $T_G$ (e.g., about −134° C.), so as to maintain the integrity of those samples. For example, the transfer module 101 transfers active labware between the freezer 105A, additional freezers (not shown), and an input/output (I/O) port 125. In one or more aspects, the transfer module 101 also transfers sample tubes (or other sample holding containers) between the active labware transferred or otherwise held within the transfer module 101. The I/O port 125 is configured to accept a portable storage unit 166 storing one or more active labware, where a user inserts and removes the portable storage unit 166 via an I/O door 125D. An example portable storage unit that may be employed with the store 100A is described in U.S. patent application Ser. No. 14/600,751 (titled "Portable Cryogenic Workstation") and filed on Jan. 20, 2015, the disclosure of which is incorporated herein by reference in its entirety.

The transfer module 101, is in one or more aspects portable so as to be moved or otherwise relocated to service other freezers in addition to the freezer 105A. Here, a cart 190 supports the transfer module 101, and is configured to move the transfer module 101 along a track 192. In one or more aspects, the cart 190 is propelled automatically by a motor assembly in response to a movement command, or in other aspects, may be moved manually by a user. In aspects where the transfer module 101 services multiple freezers, the cart 190 and track 192 enables the transfer module 101 to relocate to each of those multiple freezers. In one or more aspects, a motion system (e.g., gantry type crane) is provided above the transfer module 101, in addition to (or in place of) the cart 190 and track 192, for moving the transfer module 101 between freezers. In still other aspects, in place of the track 192, the transfer module 101 is moved using a trackless motion system that uses a local positioning system (e.g., GPS, Wi-Fi, optical (e.g., camera based), radar, LIDAR, floor or freezer mounted sensors). Propulsion can be provided to the transfer module by any known motion system, such as on-board motors that drive wheels or gears, in floor linear motors, off-board motors that drive cables or gears, or an overhead gantry system.

Figure 1B:
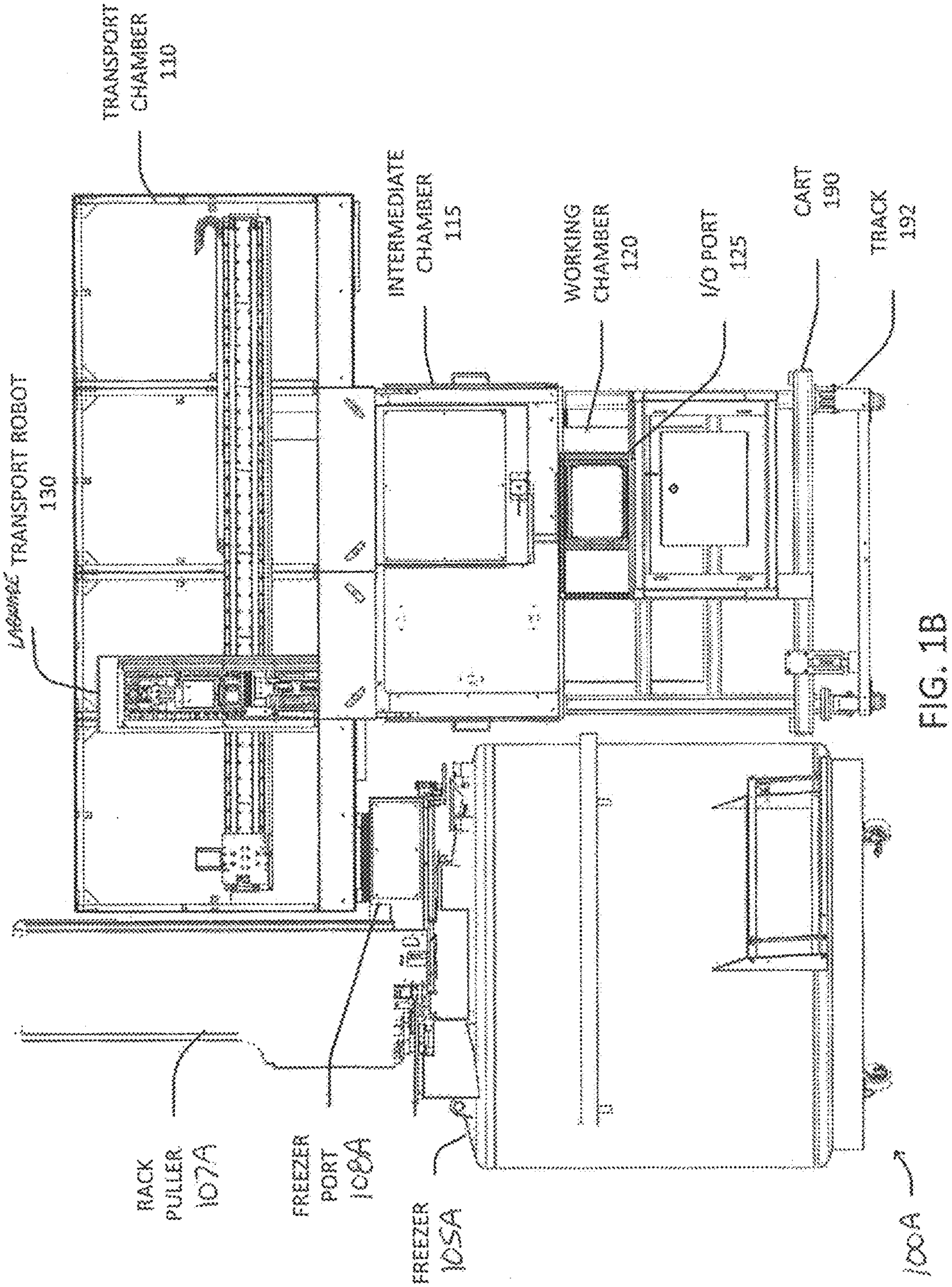
FIG. 1B a schematic front illustration of the automated temperature controlled sample specimen laboratory storage system of FIG. 1A incorporating aspects of the present disclosure.

FIG. 1B illustrates a front view of the store 100A. Here, the disposition of the transfer module 101 is shown in further detail. The transfer module 101 includes three chambers: a transport chamber 110, an intermediate chamber 115, and a working chamber 120. It should be understood that the configuration of the transfer module 101 described herein is exemplary and the transfer module 101 may have any suitable configuration for transporting labware. The chambers 110, 115, 120 are coupled to one another in series, and passage between the chambers is selectively enabled via automated doors (not shown). The transport chamber 110, in both FIGS. 1A and 1B, is shown in a cutaway view to illustrate components internal to the transport chamber 110, including a labware transport robot 130. The transport chamber 110 may be closed as shown in FIG. 1E, which may contribute to preserving the temperature of the samples below the glass transition temperature. The labware transport robot 130 operates to transport labware between the freezer 105A, the I/O port 125, the working chamber 120, and additional locations. The labware transport robot 130 accesses the working chamber 120 by passing through the intermediate chamber 115. A freezer port 108A facilitates the transfer of labware between the freezer 105A and the transfer module 101. In particular, the rack puller 107A, after raising a storage rack 185 (FIG. 1F) from the freezer 105A, moves the labware into the freezer port 108A. The freezer port 108A, in turn, positions the labware for pickup by the labware transport robot 130. Conversely, when returning or storing labware to the freezer 105A, the freezer port 108A moves the labware toward the rack puller 107A, where the labware is added to a storage rack 185 before the rack puller 107A lowers the storage rack 185 into the freezer 105A. The freezer port 108A is mounted to the freezer 105A and couples to the transport chamber 110 when the transfer module 101 is positioned to access the freezer 105A. In such a configuration, the transport chamber 110 includes a port (e.g., an aperture) for connecting to the freezer port 108A, or may include a component of the freezer port 108A. In other aspects, the freezer port 108A may be mounted to the transport chamber 110, and aligns with the rack puller 107A when the transfer module 101 is positioned to access the freezer 105A.

The working chamber 120 maintains a cryogenic environment, and enables the selection and transfer of individual samples between labware. In contrast, the intermediate chamber 115 and transport chamber 110 maintain temperatures and humidity above that of a cryogenic environment.

For example, the transport chamber 110 may be configured absent active temperature or humidity control, and, thus, may maintain a temperature comparable to room temperature. The intermediate chamber 115 may be configured similarly. However, both chambers 110, 115 may be cooled and/or dehumidified via convection from the cryogenic environment of the working chamber 120 and/or other cooling and/or dehumidifying methods. In one or more aspects, the transfer module 101 may include chambers in a different configuration. For example, a single chamber may encompass both the transport chamber 110 and intermediate chamber 115, or the intermediate chamber 115 may be omitted, the transport chamber 110 being coupled directly to the working chamber.

Figure 1C:
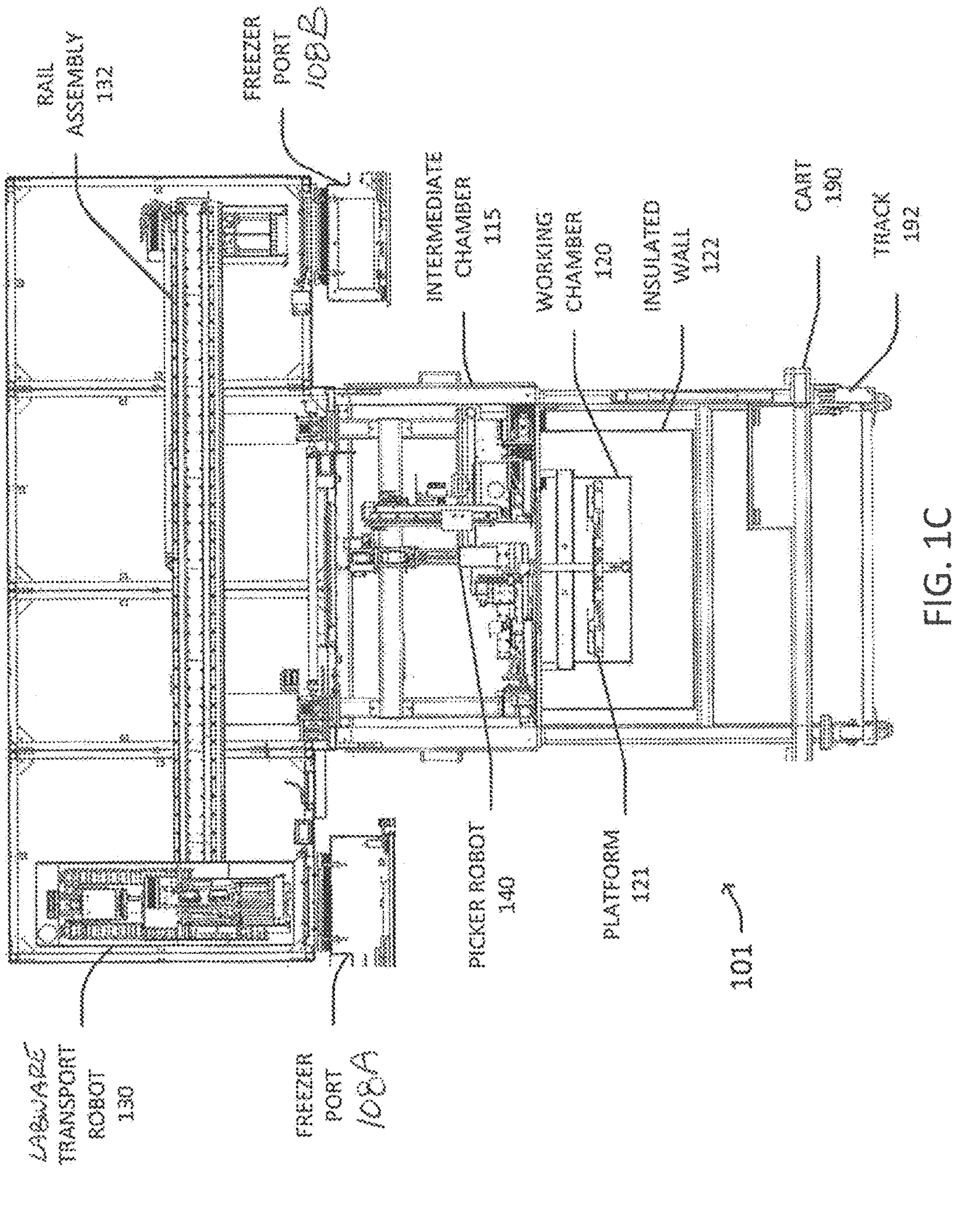
FIG. 1C a schematic perspective illustration of a portion of the automated temperature controlled sample specimen laboratory storage system of FIG. 1A incorporating aspects of the present disclosure.

FIG. 1C shows a cross-section view of the transfer module 101. Here, a second freezer port 108B is shown for servicing a freezer on an opposite side of the transfer module 101 from the freezer 105A. The working chamber 120, as indicated above, is configured to maintain a cryogenic environment, thereby preserving the temperature of the samples within it below a respective glass transition temperature $T_G$ of the samples (e.g., −134° C.). To facilitate this environment, an insulated wall 122 encompasses the bottom and sides of the chamber 120, and the top of the chamber 120 may be substantially isolated from the intermediate chamber 115 (e.g., via a removable cover or door) when sample boxes are not being transferred into or out of the working chamber 120. The working chamber 120 houses a platform 121 that supports multiple labware and configurations, which are moved into and out of the working chamber 120 by the labware transport robot 130.

The intermediate chamber 115 houses operational machinery, including a picker robot 140. The picker robot 140 is configured to transfer individual samples between labware within the working chamber 120. The picker robot 140 substantially resides in the intermediate chamber 115, extending partially into the working chamber 120 during a sample transfer operation. As a result, the picker robot 140 may avoid adverse effects of exposure to the cryogenic environment of the working chamber 120.

Figure 1D:
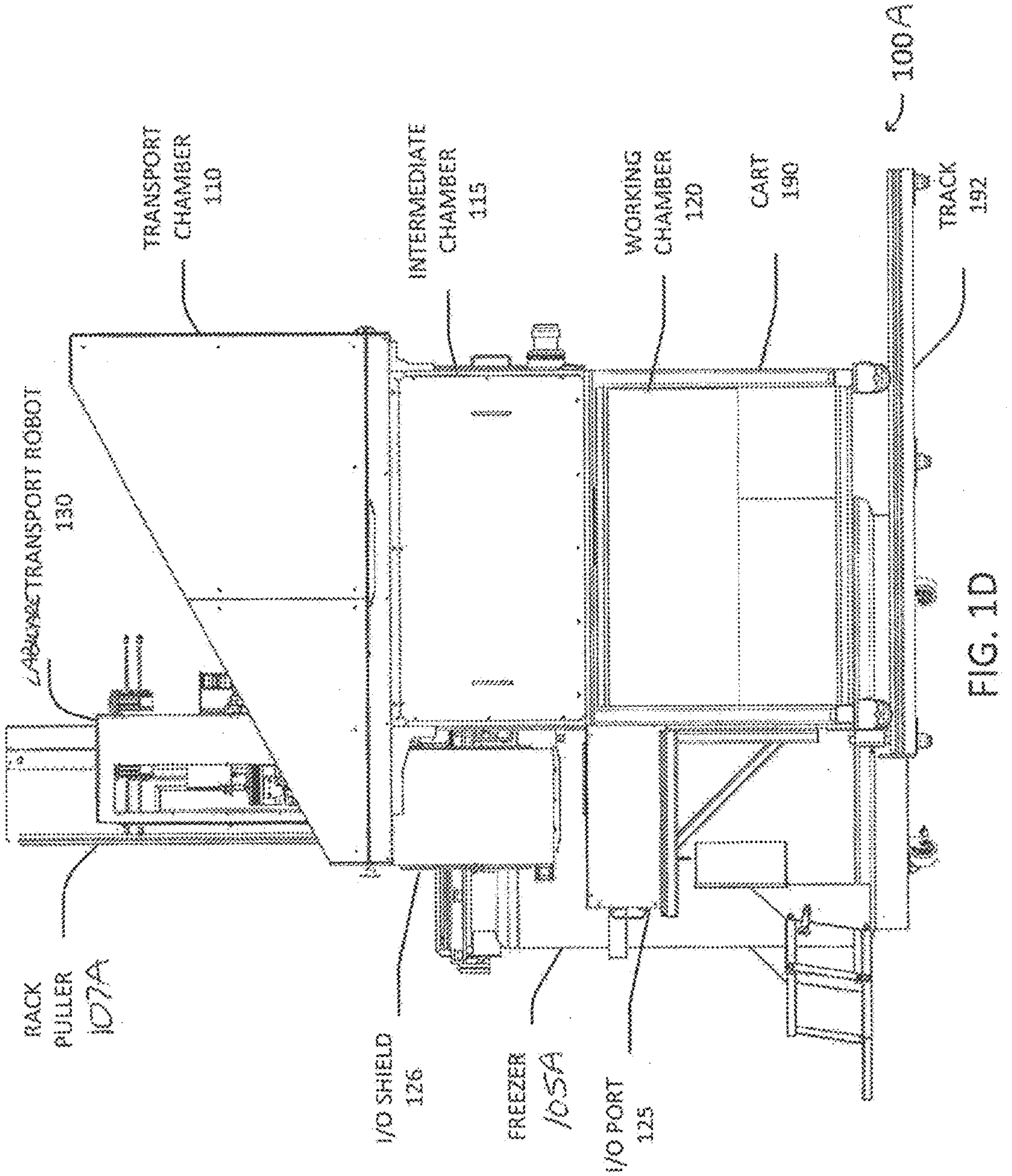
FIG. 1D a schematic side illustration of the automated temperature controlled sample specimen laboratory storage system of FIG. 1A incorporating aspects of the present disclosure.
Figure 1E:
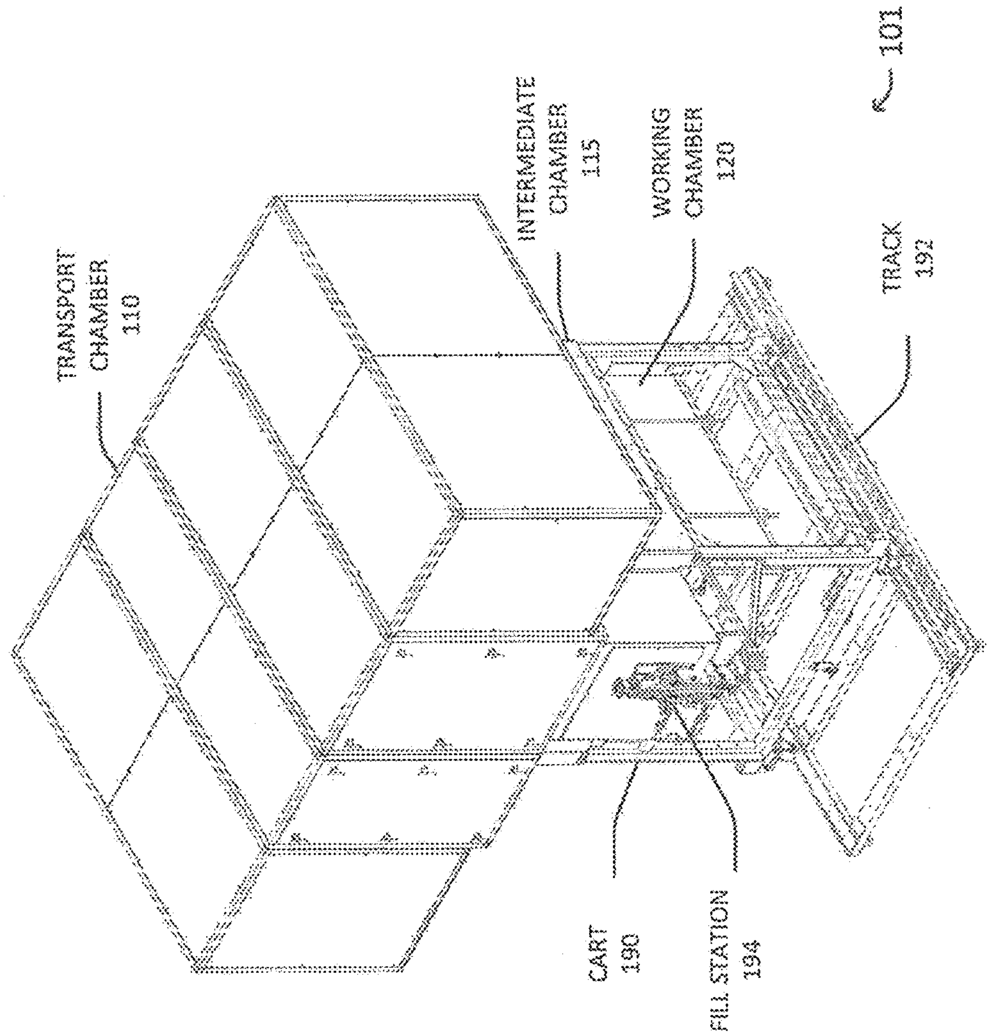
FIG. 1E a schematic perspective illustration of a portion of the automated temperature controlled sample specimen laboratory storage system of FIG. 1A incorporating aspects of the present disclosure.

FIG. 1D illustrates a side view of the store 100A. An I/O (input/output) shield 126 is shown. The I/O shield 126 is coupled to one or both of the I/O port 125 and the transport chamber 110, and serves as a passageway between them. When the labware transport robot 130 adds or removes a labware from the I/O port 125, it extends through the I/O shield 126. The I/O shield 126 is configured to protect the labware and labware transport robot 130 from interference. The I/O shield 126 may also include a removable cover or door at the threshold of the transport chamber 110 to reduce gas transfer between the transport chamber 110 and the external environment.

FIG. 1E illustrates the transfer module 101 in a further view. Here, the transport chamber 110 is shown with its enclosure intact, and a fill station 194 may be located at the front, rear or side of the transfer module 101. The fill station 194 may connect to a liquid coolant source, and directs a liquid coolant (e.g., a cryogenic fluid such as liquid nitrogen) to the working chamber 120 where it cools the working chamber to a cryogenic temperature.

Figure 1F:
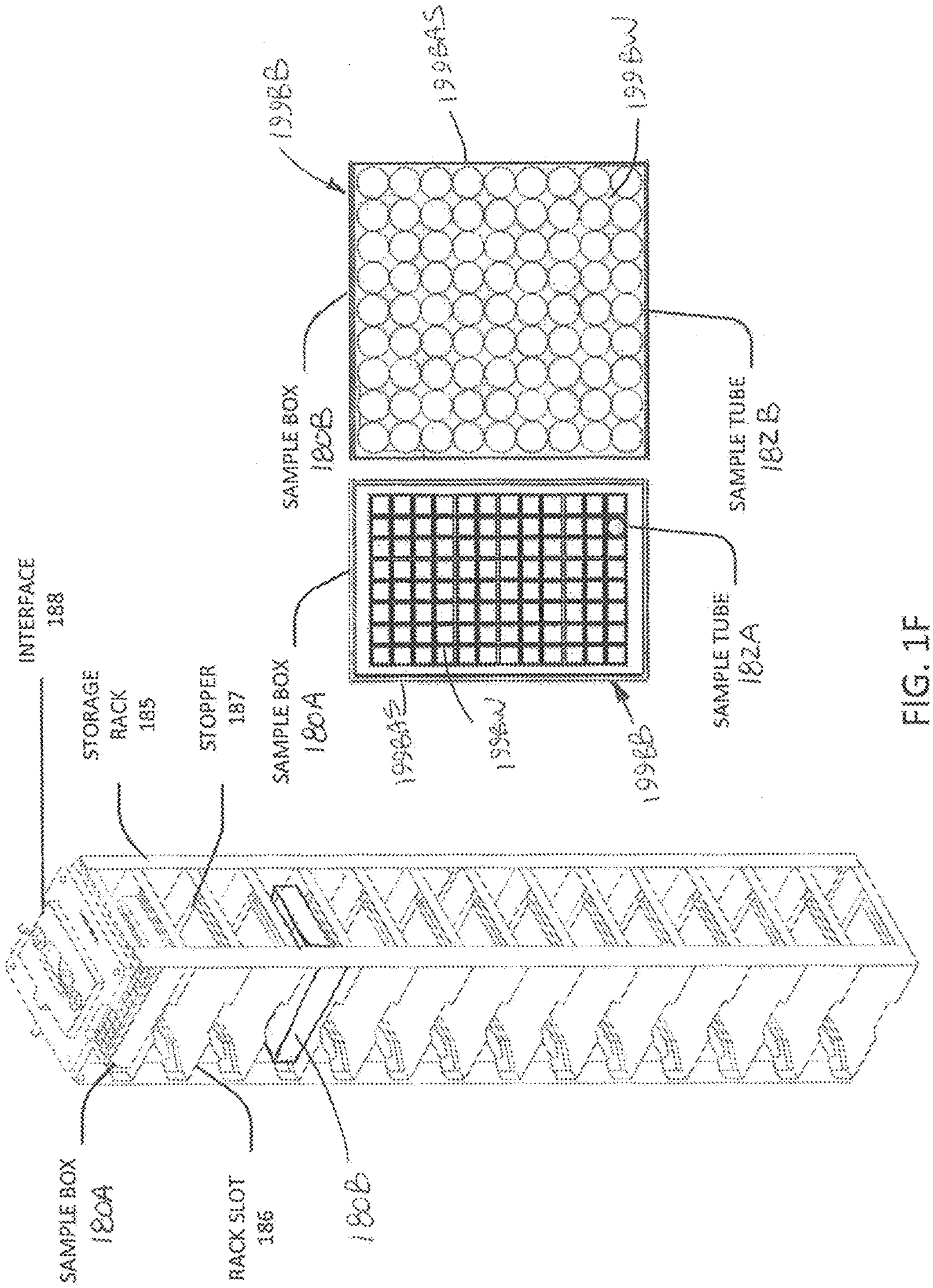
FIG. 1F a schematic perspective illustration of a portion of the automated temperature controlled sample specimen laboratory storage system of FIG. 1A incorporating aspects of the present disclosure.

FIG. 1F illustrates an example storage rack 185 and labware in the form of sample boxes 180A, 180B that may be implemented in the store 100A. The store 100A is configured to store and transfer sample boxes (or other suitable labware) of multiple different formats. For example, sample boxes 180A, 180B, shown in top-down view, correspond to a Society for Biomolecular Screening (SBS) standard format box and a Cryobox standard format box, respectively. Each sample box 180A, 180B includes multiples slots for storing samples, such as sample tubes 182A, 182B.

The storage rack 185 includes multiple rack slots (e.g., storage locations 186) for storing respective labware, such as the sample boxes 180A, 180B. The freezer 105A may store multiple storage racks substantially similar to the storage rack 185 so as to form a storage array SA within the freezer 105A, and the rack puller 107A is configured to selectively raise the storage racks 185 from the freezer 105A by engaging with an interface 188 mounted to the top of each storage rack 185. To accommodate storage of labware in different formats, each storage location 186 may be adapted to accommodate, using the sample boxes 180A, 180B as an example, a largest box format (e.g., sample box 180B, Cryobox), and may optionally include a stopper 187 positioned to accommodate a smaller box format (e.g., sample box 180A, SBS). The stopper 187 prevents the sample box 180A from moving to the rear of the storage rack 185, thereby maintaining a face of the sample box 180A at a front face of the storage rack 185. The stopper 187 may be omitted from slots accommodating the larger box format, or may be shaped to allow passage by the larger box format. As a result, the storage rack 185 can store and present the sample boxes 180A, 180B in a uniform manner. In other aspects, to provide greater storage capacity and maximize use of space within a freezer, the storage rack 185 is adapted to accept a single, uniform box format and orientation.

In other aspects, each of one or more storage locations (similar to storage locations 186) and/or each of one or more store rack locations (similar to storage locations 210SL) may have a spare simulacrum store rack location, or spare simulacrum storage rack location associated with the given store rack location or given storage rack location. For example, a spare simulacrum store rack location (or spare simulacrum storage rack location) may be juxtaposed with the given store rack location (or given storage rack location) (e.g., the spare locations may be interdigitated between storage (non-spare or "active") locations). The spare simulacrum store rack location (or spare simulacrum storage rack location) is arranged to hold simulacrum labware substitutes 199 with the given "active" storage location filled with active labware and with the given "active" storage location empty (i.e., nothing held in the given "active" storage location). In one or more aspects the spare simulacrum store rack location (or spare simulacrum storage rack location) may serve to hold active labware in a manner similar to that of an "active" storage location (e.g., where the simulacrum labware substitute is removed from the storage location and replaced with an active labware having a corresponding form factor (fit up) as the removed simulacrum labware substitute). The controller 170 is configured to select a state of (e.g., selectably switch) each of the spare simulacrum store rack location and spare simulacrum storage rack location between a "spare" storage location for holding simulacrum labware substitutes 199 and an "active" storage location for holding active labware (and the controller 170 includes a registry configured to track the change in states). The spare simulacrum store rack location and spare simulacrum storage rack location may be added to a storage array/rack in addition to the active storage locations so that the holding capacity of the storage array/rack is unaffected (unrestricted) by the respective spare simulacrum store rack locations and spare simulacrum storage rack locations. In other aspects, the spare simulacrum store rack location and spare simulacrum storage rack location may be formed by an active storage location and selectively switched between the active and spare states by the controller 170 so that the holding capacity of the storage array/rack is unaffected (unrestricted) by the respective spare simulacrum store rack locations and spare simulacrum storage rack locations.

Figure 2B:
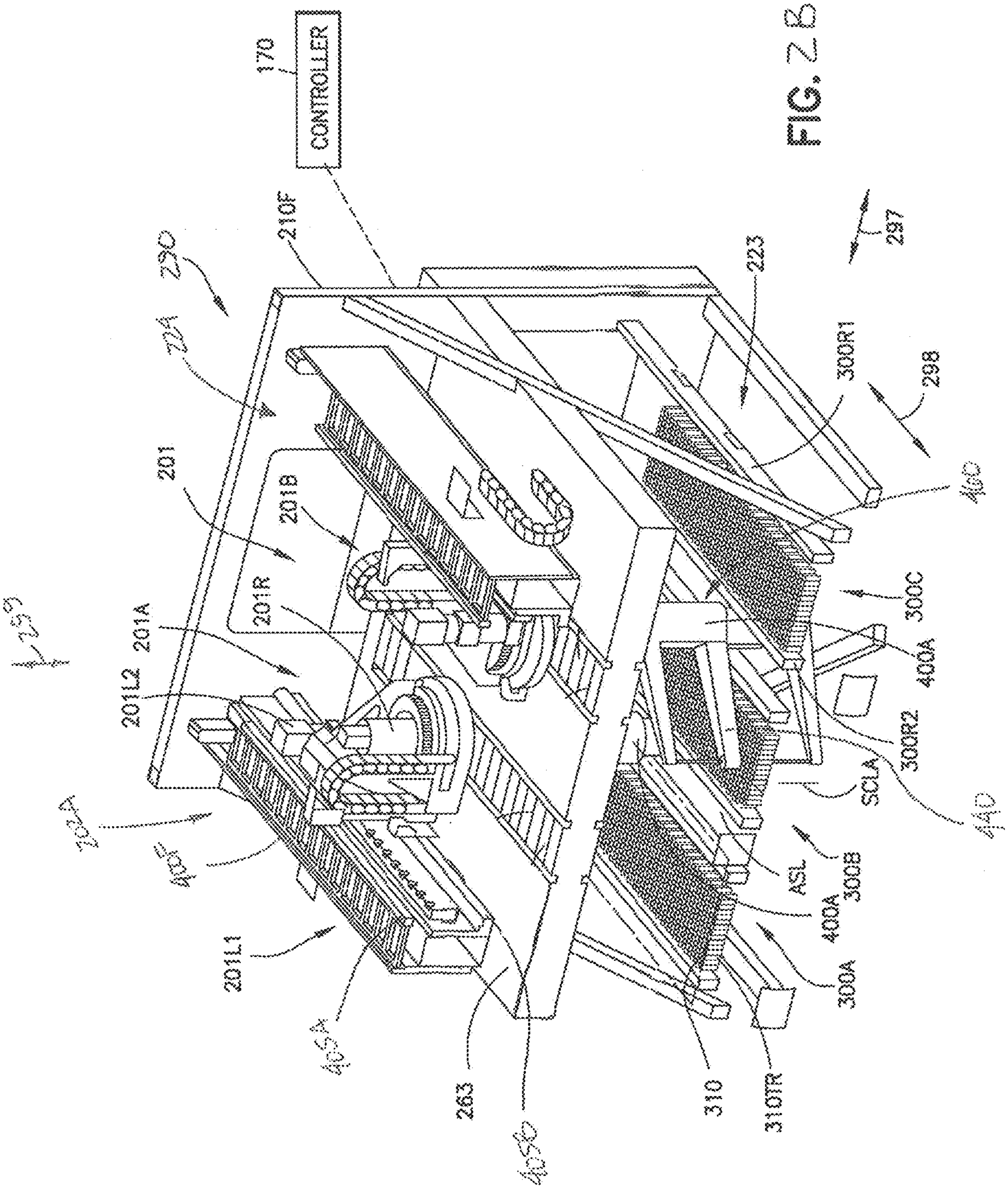
FIG. 2B is a schematic perspective illustration of a portion of the automated temperature controlled sample specimen laboratory storage system of FIG. 2A incorporating aspects of the present disclosure.
Figure 2C:
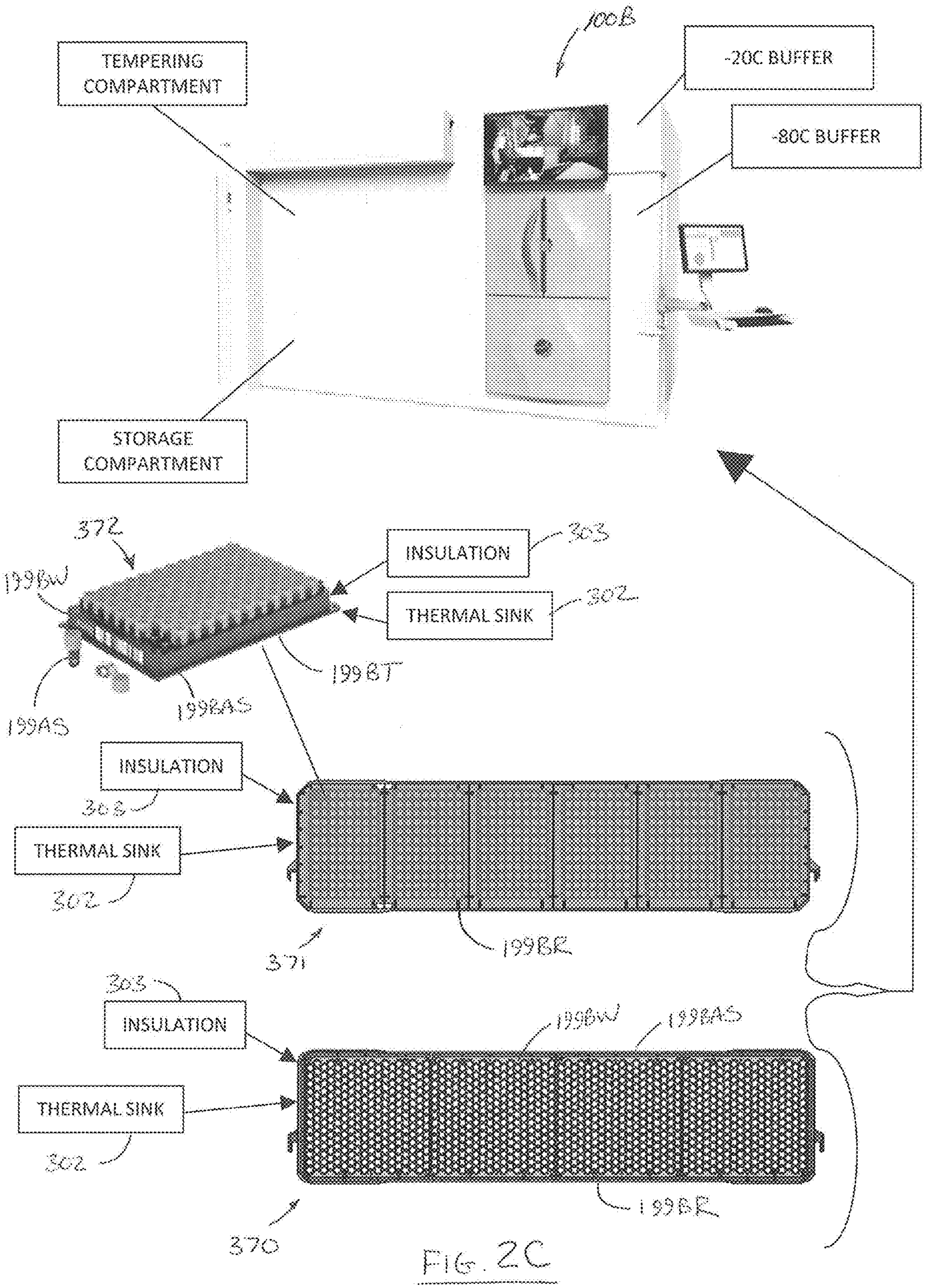
FIG. 2C is a another schematic perspective illustration of the automated temperature controlled sample specimen laboratory storage system of FIG. 2A incorporating aspects of the present disclosure.

Referring now to FIG. 2A, the aspects of the present disclosure may also be implemented in a store 100B such as illustrated in FIGS. 2A-2C. Here, the store 100B may include any suitable number of environmental zones or areas that may be isolated from one another. For example, the store 100B includes one or more low temperature storage zones 210A, 210B (each having a plurality of storage locations 210SL that collectively form a storage array SA—the low temperature storage zones are also referred to as refrigerated chambers), a transport zone 245, and a climate controlled antechamber 250. In other aspects the store 100B may have any suitable number and type of zones/areas in which samples are stored and/or transported and which may be accessed by storage facility personnel. In a manner similar to that described above, the storage locations 210SL in the storage zones 210A, 210B are configured to hold at least one of the active labware unit and/or at least one of the active labware device per storage location. Here the number of storage locations define a predetermined (maximum) capacity of active labware unit and/or active labware device storage of the storage array SA formed by a predetermined (maximum) number of the storage locations 210SL within the storage zones 210A, 210B.

In one aspect the transport zone 245 includes an input/output module 230, a transport shuttle 212 and one or more sample selector/transfer modules 290 where the sample selector modules are disposed at least partly within the transport zone 245. The input/output module 230 may allow transfer of samples and/or labware to and from the store 100B while maintaining a predetermined temperature within the transport zone 245. The sample selector modules 290, which will be described in greater detail below, may provide sorting capability for moving samples/labware within or between standard density (SD) and/or high density (HD) sample racks/trays as described in U.S. Pat. No. 9,630,775 (titled "Sample Selector") and issued on Apr. 25, 2017, the disclosure of which is incorporated herein by reference in its entirety.

The transport zone 245 may be maintained at any suitable low temperature, such as about −20° C., in which the transport shuttle 212 and/or other automation may operate to transfer labware between the low temperature storage zones 210A, 210B, the sample selector modules 290 and the input/output module 230. The transport shuttle 212 may interface with a tile wall 215 where each tile 261 is arranged to create, for example, a robotically friendly insulating closure of the low temperature storage zones 210A, 210B for removing labware from the low temperature storage zones 210A, 210B in any suitable manner. The transport shuttle 212 is configured to transport the labware between the low temperature storage zones 210A, 210B and any other components of the store 100B, which may include but is not limited to transport of labware to and from the sample selector modules 290.

In one aspect the climate controlled antechamber 250 may include door(s) 250D1 for providing personnel access to the at least the transport zone 245 and/or to the sample selector modules 290, at least part of which may be disposed within the climate controlled antechamber 250 (e.g. the sample selector modules 290 may be mounted through a wall separating/isolating the climate controlled antechamber 250 from the transport zone 245. As may be realized, the climate controlled antechamber 250 may be maintained at any suitable temperature allowing for human entry into the climate controlled antechamber 250.

The store 100B may include any suitable refrigeration system(s) 225 and/or dehumidification system(s) 220 for maintaining respective predetermined temperatures within the different zones of the store 100B. In one aspect the transport zone 245, transport shuttle 212, tile wall 215, low temperature storage zones 210A, 210B, transport zone 145 and input/output modules of the store 100B may be substantially similar to those described in U.S. Pat. No. 7,635,246 issued on Dec. 22, 2009, U.S. Pat. No. 7,648,321 issued on Jan. 19, 2010, U.S. Pat. No. 7,793,842 issued on Sep. 14, 2010, U.S. Pat. No. 8,252,232 issued on Aug. 28, 2012 and U.S. Pat. No. 9,702,887 issued on Jul. 11, 2017, and U.S. Pat. No. 10,168,344 issued on Jan. 1, 2019, the disclosures of which are incorporated by reference herein in their entireties.

Referring now to FIG. 2B each sample selector module 290 includes a frame 210F, at least one transfer device or unit 201A, 201B having a drive section 201 connected to the frame 210F and at least one transfer arm portion 400A rotatably connected to the drive section 201. The sample selector module has an isolated climate controlled chamber or zone 223. In one aspect the isolated climate controlled chamber 223 may be maintained at a low temperature, such as for example, about −80° C. or any other suitable low temperature. In one aspect the isolated climate controlled chamber 223 may be actively cooled while in other aspects the isolated climate controlled chamber 223 may be cooled in any suitable manner such as with one or more evaporators in communication with the isolated climate controlled chamber 223.

The sample selector modules 290 include an isolation member 263 disposed opposite to and spaced apart from a top wall of the sample selector module 290 so as to form a drive section chamber 224 that may be maintained at any suitable predetermined temperature suitable for the operation of drive section 201 components as described herein. In one aspect, the drive section chamber 224 may be maintained at any suitable temperature, for example, at a temperature of about or above −20° C.

The sample selector modules 290 include one or more input/output openings or apertures 260, through which labware such as sample trays 310TR pass for insertion to and removal from the isolated climate controlled chamber 223. Each input/output opening 260 may be a sealable or otherwise closable opening that is sealed or otherwise closed by a respective tile 261. Suitable examples of sliding tile closures can be found in, for example, U.S. Pat. No. 7,635,246 issued on Dec. 22, 2009, U.S. Pat. No. 7,648,321 issued on Jan. 19, 2010, U.S. Pat. No. 7,793,842 issued on Sep. 14, 2010, U.S. Pat. No. 8,252,232 issued on Aug. 28, 2012 and U.S. Pat. No. 9,702,887 issued on Jul. 11, 2017, and U.S. Pat. No. 10,168,344 issued on Jan. 1, 2019, previously incorporated by reference herein. In one aspect, any suitable automated transfer mechanism of the store 100B, such as transport shuttle 212, may insert or remove a sample tray 310TR to or from the isolated climate controlled chamber 223 through an input/output opening 260 by aligning an automated transfer mechanism of the transport shuttle 212 with the tile 261 in front of the desired opening. Each tile 261 may be configured with one or more gripping members, such as a recess or protrusion, that allows the automated transfer mechanism to lift the tile 261 for opening the input/output opening 260 in, for example, a manner substantially similar to that described in U.S. Pat. No. 7,635,246 issued on Dec. 22, 2009, U.S. Pat. No. 7,648,321 issued on Jan. 19, 2010, U.S. Pat. No. 7,793,842 issued on Sep. 14, 2010, U.S. Pat. No. 8,252,232 issued on Aug. 28, 2012 and U.S. Pat. No. 9,702,887 issued on Jul. 11, 2017, and U.S. Pat. No. 10,168,344 issued on Jan. 1, 2019, previously incorporated by reference herein. In other aspects the sample selector module 290 may include one or more drives coupled to each of the tiles 261 for opening and closing a respective input/output opening 260.

Referring also to FIG. 2C, each of the input/output openings 260 is associated with a respective sample tray holder 300A, 300B, 300C. Each sample tray holder 300A, 300B, 300C may include respective sample tray supports 300R1, 300R2 that may be supported by the frame 210F in any suitable manner. The sample tray supports 300R1, 300R2 may be spaced from each other by any suitable amount so that a sample tray 310TR may be slid into or out of the respective sample tray holder 300A, 300B, 300C by a tray conveyor that is external to the sample selector module 290 (e.g. the tray conveyor is one that is separate from the sample selector module 290 such as the tray shuttle 112). In one aspect, each sample tray holder 300A, 300B, 300C may have a length suitable for holding a sample tray 310TR having one or more standard density or high density sample racks (see the high density sample racks generally referred to as high density racks 370 in FIG. 2C and the standard density sample racks generally referred to as standard density racks 371 configured to hold standard density trays/plates in FIG. 2C disposed thereon such that the sample racks are arranged end to end. The standard density racks 371 and high density racks 370 configured to hold high density trays/plates are substantially similar to those described in U.S. Pat. No. 9,630,775 (titled "Sample Selector") issued on Apr. 25, 2017, the disclosure of which was previously incorporated by reference herein in its entirety.

Referring now to FIG. 2C, as noted above the sample selector module 290 includes one or more transfer devices 201A, 201B. Each transfer device 201A, 201B (described herein with respect to transfer device 201A but it should be understood that transfer device 201B may be identical to transfer device 201A) includes a respective drive portion 202A of drive section 201 and a transfer arm portion 400A. The drive portion 202A may be disposed within the drive section chamber 224 and include one or more rotary drive motors connected to a frame 400F of the drive portion 202A. In one aspect the drive portion 202A may also include at least one linear drive motor 201L2 connected to the frame 400F for moving at least a portion of the transfer arm portion 400A in the direction of arrow 299.

In one aspect the drive portion 202A may be coupled to the frame 210F of the sample selector module 200 in any suitable manner. For example, the drive portion 202A may be mounted to a linear drive 201L1 of the drive section 201 that is supported within the frame 210F so that a path of travel of the linear drive 201L1 and movement of the transfer arm portion 400A carried by the linear drive 201L1 is substantially in the direction of arrow 298 (e.g. along a longitudinal axis of the sample tray 310TR so that the transfer arm portion travels along a respective aisle ASL formed between the sample tray holders 300A, 300B, 300C. In other aspects the linear drive 201L1 may be a multi-axis linear drive providing movement of the transfer arm portion 400A in the direction of arrows 297, 298. The linear drive 201L1 may be any suitable linear drive such as a linear stepper motor, a belt and pulley system, a screw drive or any other suitable drive. In one aspect the drive portion 202A may ride along one or more linear rails 405A, 405B of the linear drive 201L1 while in other aspects the drive portion 202A may be supported by the linear drive 201L1 in any suitable manner. As may be realized, any suitable encoders or position detectors 406 may be provided for determining, along with controller 170, a position of the transfer arm portion 400A along a length of the linear drive 201L1 for positioning the transfer arm portion 400A relative to the sample holding locations 310 within the sample tray 310TR.

The transfer arm portion 400A may include a coaxial (e.g. concentrically collocated) drive shaft assembly 460 having a common axis of rotation (which may be substantially parallel with a sample container longitudinal axis SOLA), a sample container holder 440, a top (e.g. upper) pusher member 430 and a bottom (e.g. lower) pusher member 420. The top and bottom pusher members 430, 420 are configured to push sample containers to and from the trays in a manner similar to that described herein. A suitable example of the sample selector module 290 is described in U.S. Pat. No. 9,630,775 (titled "Sample Selector") issued on Apr. 25, 2017, the disclosure of which was previously incorporated by reference herein in its entirety.

It is again noted that the configuration of the stores 100A, 100B are exemplary and that the stores 100A, 100B may have any suitable configuration. For example, in addition to stores that are similarly configured (e.g., dewar type stores and insulated wall/tile type stores), other examples of stores in which the aspects of the present disclosure may be employed include the store described in U.S. Pat. No. 10,834,918 (titled "Modular Sample Store") issued on Nov. 17, 2020, the disclosure of which is incorporated herein by reference in its entirety.

In one or more aspects, at least one of the automated transports (e.g., such as the labware transport robot 130 and the rack puller 107A of store 100A and the transport shuttle 212 of store 100B) of the stores 100A, 100B are configured to balance addition and removal of the simulacrum labware substitutes 199 from the storage array SA, with addition and removal of a corresponding active labware unit and active labware device from the storage array SA. For example, the stores 100A, 100B include a controller 170 operably coupled to the automated transports of the respective store 100A, 100B. The controller 170 issues movement/transport commands to the automated transports for adding and removing the simulacrum labware substitutes 199, the active labware units LWU, and the active labware devices LWD to and from the storage arrays SA. As described herein, the addition and removal of the simulacrum labware substitutes 199 is balanced with the addition and removal of the corresponding labware units LWU and/or corresponding labware devices LWD so as to maximize fill of the storage array SA throughout the storage array SA (i.e., maximized in that each storage location 210SL in the storage array SA is filled with one or more of the simulacrum labware substitutes 199, labware units LWU, and labware devices LWD).

As will be described in greater detail herein, the automated transports, such as the labware transport robot 130 and the transport shuttle 212, have a gripper 1280 (see FIGS. 12B and 12C) configured to automatically engage and swap, at each storage location, the one or more of the labware unit and labware device with the at least one simulacrum labware substitute, and vice versa, so that fill of the storage array is substantially constant, throughout the storage array, with addition and removal of the one or more of the labware unit and labware device from each storage location. The gripper 1280 has a holding location (e.g., one of gripper holding locations 1260, 1261—FIG. 12B) for holding the one or more of the labware unit and labware device held by the gripper 1280 of the automated transport, and a spare holding location (e.g., the other one of gripper holding locations 1260, 1261—FIG. 12B) for holding the at least one simulacrum labware substitute 199 held by the gripper 1280 and swapping, at each storage location 210SL, the one or more of the labware unit and labware device and the simulacrum labware substitute 199 with each other.

Referring to FIGS. 1A, 2A, 3A, and 3B, as noted above, the stores 100A, 100B are filled (e.g., pre-loaded) with at least one simulacrum labware substitute 199 configured so as to substitute active labware disposed in the store 100A, 100B. As described herein, the at least one simulacrum labware substitute 199 has a predetermined characteristic that simulates a respective/corresponding one of the labware unit and labware device so that the at least one simulacrum labware substitute 199 and the respective/corresponding one of the labware unit and labware device are interchangeable with respect to each storage location (e.g., storage locations 186, 210SL) holding the at least simulacrum labware substitute 199 swapped for the respective/corresponding one of the one or more of the labware unit and labware device at the storage location (e.g., the at least one of the one or more labware units LWU and labware devices LWD and the at least one simulacrum labware substitute are swapped for each other at the storage location). The at least one simulacrum labware substitute 199 held in the storage location 186, 210SL is disposed within the storage array SA so that the predetermined (maximum) capacity of the labware unit storage and/or the predetermined (maximum) capacity of the labware device storage of the storage array SA is unconstrained by the at least one simulacrum labware substitute 199 held in the storage location 186, 210SL. Disposition of the at least one simulacrum labware substitute 199 held in the storage location 186, 210SL is unconstrained (unrestricted) throughout the storage array SA so that the predetermined capacity of the one or more of the active labware unit storage and/or the active labware device storage of the storage array SA (the storage array SA being of a predetermined area) is maintained at a maximum capacity.

Figure 3A:
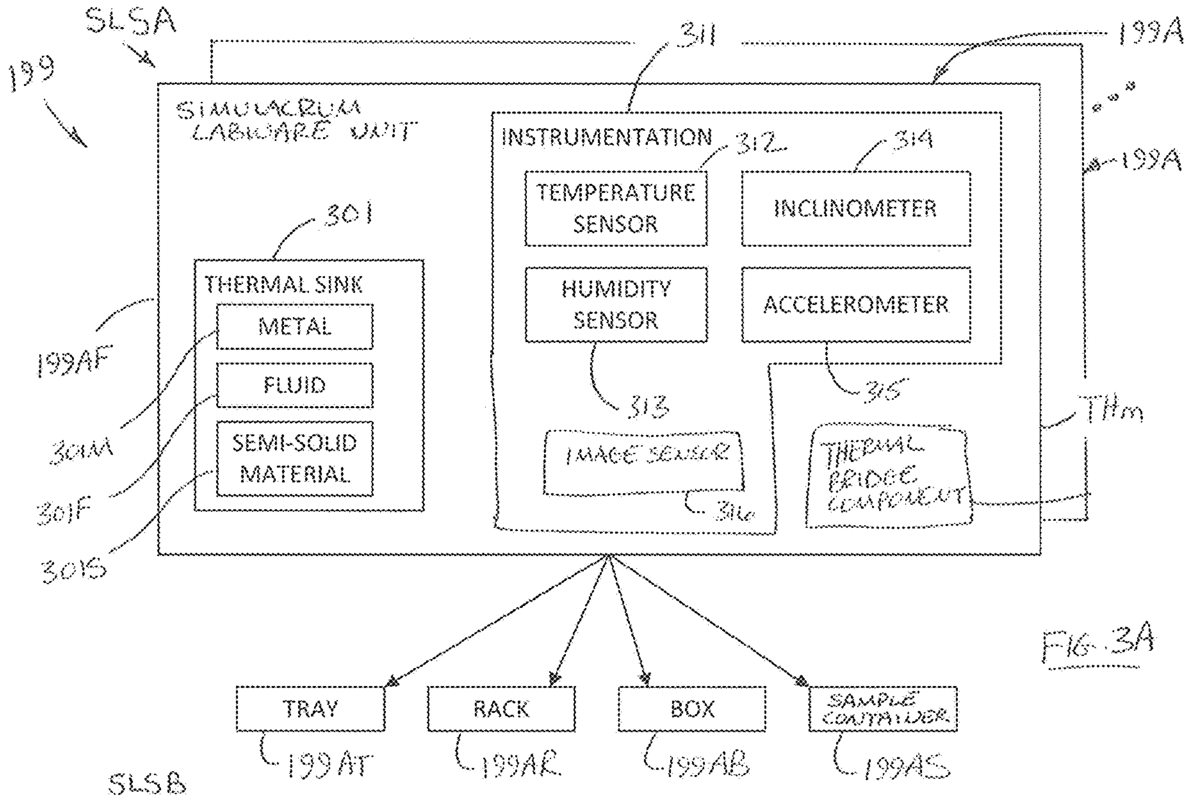
FIGS. 3A and 3B are a schematic block diagrams of simulacrum labware substitutes of the automated temperature controlled sample specimen laboratory storage systems of FIGS. 1A and 2A incorporating aspects of the present disclosure.
Figure 3B:
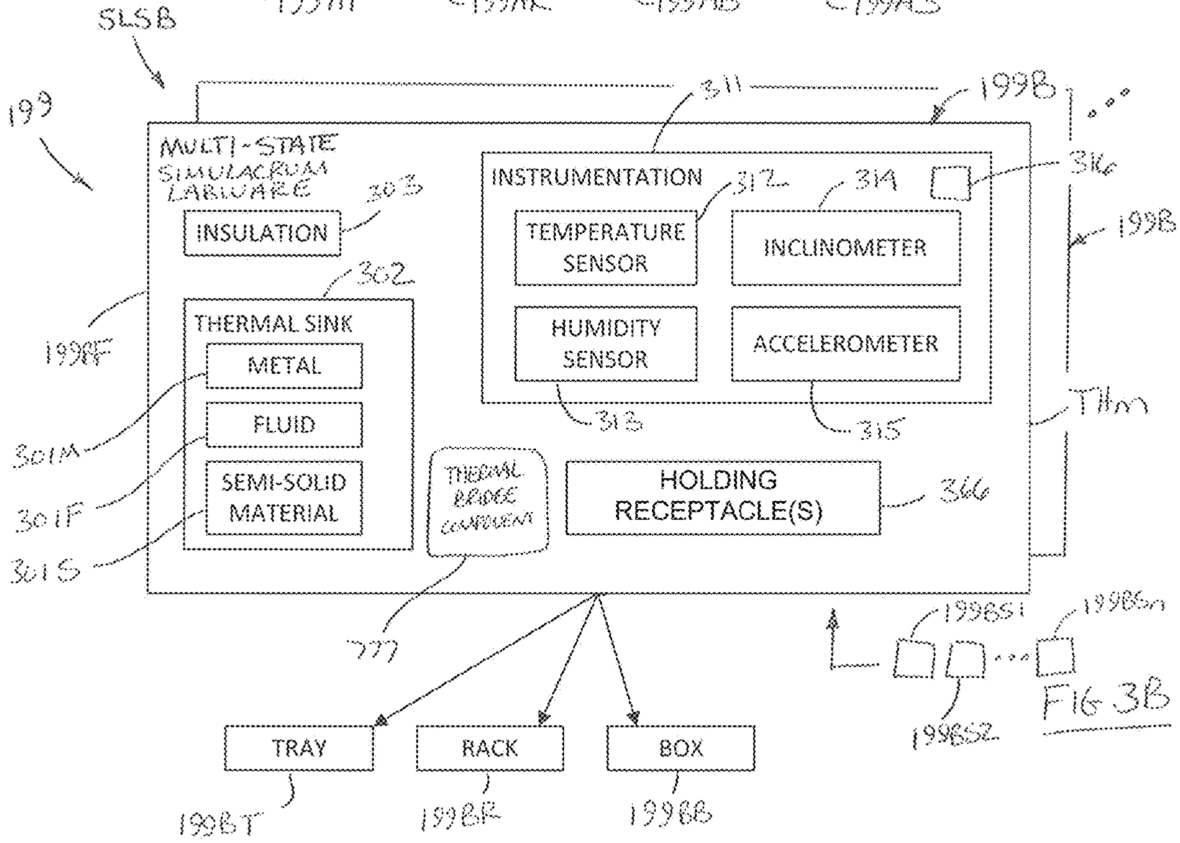

The simulacrum labware substitutes 199 are in the form of, for example, one or more of a simulacrum labware unit 199A (also referred to herein as a simulacrum labware unit substitute) and a multi-state simulacrum labware unit holder 199B (also referred to herein as a labware device substitute or a simulacrum labware device). The simulacrum labware unit 199A is a simulacrum labware substitute 199 that is configured so as to have only a simulacrum state, the simulacrum state being such that the simulacrum labware unit 199A does not receive or otherwise hold active labware and does not have capability to be active in, engaged in, and/or effects laboratory functions. In one or more aspects, the simulacrum labware unit 199A is not openable by a user (i.e., an exterior case of the simulacrum labware unit 199A is permanently sealed), is a monolithic mass (i.e., is solid or otherwise is free of (e.g., does not have/lacks) cavities into which samples are received), or is otherwise configured so as to prevent insertion of a sample specimen therein. The simulacrum labware unit 199A may be provided in a set of simulacrum labware units SLSA (FIG. 3A). Where the simulacrum labware units 199A are provided in a set, each simulacrum labware unit 199A in the set SLSA has a same predetermined thermal characteristic and/or composition; however, in other aspects at least one simulacrum labware unit 199A in the set of simulacrum labware units SLSA has a different predetermined thermal characteristic and/or composition than other simulacrum labware units 199A in the set SLSA. The multi-state simulacrum labware unit holder 199B is a simulacrum labware substitute 199 that is, at least in part, selectably switchable between an active labware state (i.e., holding/transporting samples and/or active sample containers so as to be active in, engaged in, and/or effecting laboratory functions), a simulacrum state, and a mixed (or quasi-active) state (i.e., at least a portion of the multi-state simulacrum labware unit holder 199B has a simulacrum state and at least another different portion of the multi-state simulacrum labware unit holder 199B has an active labware state). The multi-state simulacrum labware unit holder 199B may also be provided in a set of simulacrum labware units SLSB (FIG. 3B), which set may include sample containers 199AS within the holding receptacle(s) 366 of a multi-state simulacrum labware unit holder 199B. Where the simulacrum labware unit holders 199B are provided in a set, each simulacrum labware unit holder 199B in the set has a same predetermined thermal characteristic and/or composition; however, in other aspects at least one simulacrum labware unit holder 199B in the set of simulacrum labware unit holders SLSB has a different predetermined thermal characteristic and/or composition than other simulacrum labware unit holders 199B in the set SLSB.

The simulacrum labware units 199A, 199AT, 199AR, 199AB, 199AS, 199B, 199BT, 199BR, 199BB in the sets of simulacrum labware units SLSA, SLSB may be considered granular units of a respective set SLSA, SLSB. Here, each granular unit is separable (removable) from the set and swappable/interchangeable with another granular unit (i.e., a replacement that may be another simulacrum labware unit or an active labware unit) that is placed within the respective set SLSA, SLSB in its stead. For example, a granular unit (such as a single tray 199AT, rack 199AR, box 199AB, sample container 199AS, tray 199BT, rack 199BR, box 199BB) may be removed from set SLSA, SLSB and replaced (i.e., one-for-one) with an active labware unit having the same form factor (i.e., size and shape). Here, a tray 199AT may be removed from the set SLSA and replaced with an active labware tray; a rack 199AR may be removed from the set SLSA and replaced with an active labware rack or another simulacrum rack; a box 199AB may be removed from the set SLSA and replaced with an active labware box or another simulacrum box; a sample container 199AS may be removed from the set SLSA and replaced with an active labware sample container or another simulacrum sample container; a tray 199BT may be removed from the set SLSB and replaced with an active labware tray or another simulacrum tray; a rack 199BR may be removed from the set SLSB and replaced with an active labware rack or another simulacrum rack; a box 199BB may be removed from the set SLSB and replaced with an active labware box or another simulacrum box; a sample container 199AS may be removed from a holding receptacle 366 of a respective tray 199BT, rack 199BR, or box 199BB and replaced with an active labware sample container or another simulacrum sample container; and/or a whole tray 199BT (with all of the contents held holding receptacles 366), rack 199BR (with all of the contents held holding receptacles 366), or box 199BB (with all of the contents held holding receptacles 366) may be removed (e.g., as a sub-set) and replaced with a corresponding one of another whole simulacrum tray, another whole simulacrum rack, another whole simulacrum box, an active labware tray, an active labware rack, and an active labware box. As can be realized from the above, the granular units of a set SLSA, SLSB may be interchanged in any suitable manner with any suitable level of granularity (e.g., one-for one, at least one sample container held in a holding receptacle 366 of a rack/tray/box, at least one tray/box held in a rack, and/or in any other suitable combination).

As noted above the simulacrum labware units 199A have a predetermined characteristic that simulates a predetermined characteristic of active labware. Here, for exemplary purposes, the simulacrum labware units 199A include, but are not limited to, simulacrum tray units 199AT, simulacrum rack units 199AR, simulacrum box units 199AB, and simulacrum sample container units 199AS. In one or more aspects, the predetermined characteristic of the simulacrum labware units 199A has a first thermal mass characteristic (as described herein) that is an analogue for a second thermal mass characteristic of a respective/corresponding one of the interchangeable (active) labware units LWU for which the simulacrum labware units 199A is a substitute. In other aspects, the predetermined characteristic is any one or more of the characteristics described herein. The first thermal mass characteristic and the second thermal mass characteristic are the same in character and/or magnitude; however, in other aspects the first and second thermal mass characteristics may be different in character and/or in magnitude.

The simulacrum tray units 199AT have a shape and size that simulates (or is otherwise an analogue for) the shape and size of (active) sample tray 281 (FIG. 2A), such as an SBS sample tray or other suitable sample holding trays such as described in U.S. Pat. No. 10,481,171 issued on Nov. 19, 2019 (titled "Automated Sample Storage System Having Storage Consumable With Sub-Optimal Storage Density") and U.S. Pat. No. 7,858,044 (titled "Multi-Well Plate Providing A High-Density Storage And Assay Platform") issued on Dec. 28, 2010, the disclosures of which are incorporated herein by reference in their entireties. The simulacrum tray units 199AT are interchangeable with and handled in the same manner as the sample tray 281, within the stores 100A, 100B. As noted above, the simulacrum tray units 199AT have a thermal mass THm that is an analogue to the thermal mass of the active sample tray 281. In one aspect the thermal mass THm is an analogue of the thermal mass of the active sample tray 281 with the active sample tray 281 filled to maximum capacity with active labware units LWU; while in other aspects, the thermal mass THm is an analogue of the thermal mass of the active sample tray 281 without active labware units LWU or a thermal mass of the active sample tray 281 holding any suitable predetermined number of active labware units LWU.

The simulacrum rack units 199AR have a shape and size that simulates the shape and size of one or more of the (active) high density racks 370 (FIG. 2C) and the (active) standard density racks 371 (FIG. 2C). The simulacrum rack units 199AR are interchangeable with and handled in the same manner as the high density racks 370 and the standard density racks 371, within the stores 100A, 100B. As noted above, the simulacrum rack units 199AR have a thermal mass THm that is an analogue to the thermal mass of a respective one of the high density racks 370 and the standard density racks 371. In one aspect the thermal mass THm is an analogue of the thermal mass of the high density racks 370 and the standard density racks 371 with the rack filled to maximum capacity with active labware units LWU; while in other aspects, the thermal mass THm is an analogue of the thermal mass of the respective one of the high density racks 370 and the standard density racks 371 without active labware units LWU or a thermal mass of the respective one of the high density racks 370 and the standard density racks 371 holding any suitable predetermined number of active labware units LWU.

The simulacrum box units 199AB have a shape and size that simulates the shape and size of one or more of the (active) sample boxes 180A, 180B (FIG. 1F). The simulacrum box units 199AB are interchangeable with and handled in the same manner as the sample boxes 180A, 180B, within the stores 100A, 100B. As noted above, the simulacrum box units 199AB have a thermal mass THm that is an analogue to the thermal mass of a respective sample box 180A, 180B. In one aspect the thermal mass THm is an analogue of the thermal mass of the respective sample box 180A, 180B with the sample box 180A, 180B filled to maximum capacity with active labware units LWU; while in other aspects, the thermal mass THm is an analogue of the thermal mass of the sample box 180A, 180B without active labware units LWU or a thermal mass of the sample box 180A, 180B holding any suitable predetermined number of active labware units LWU.

Figure 4:
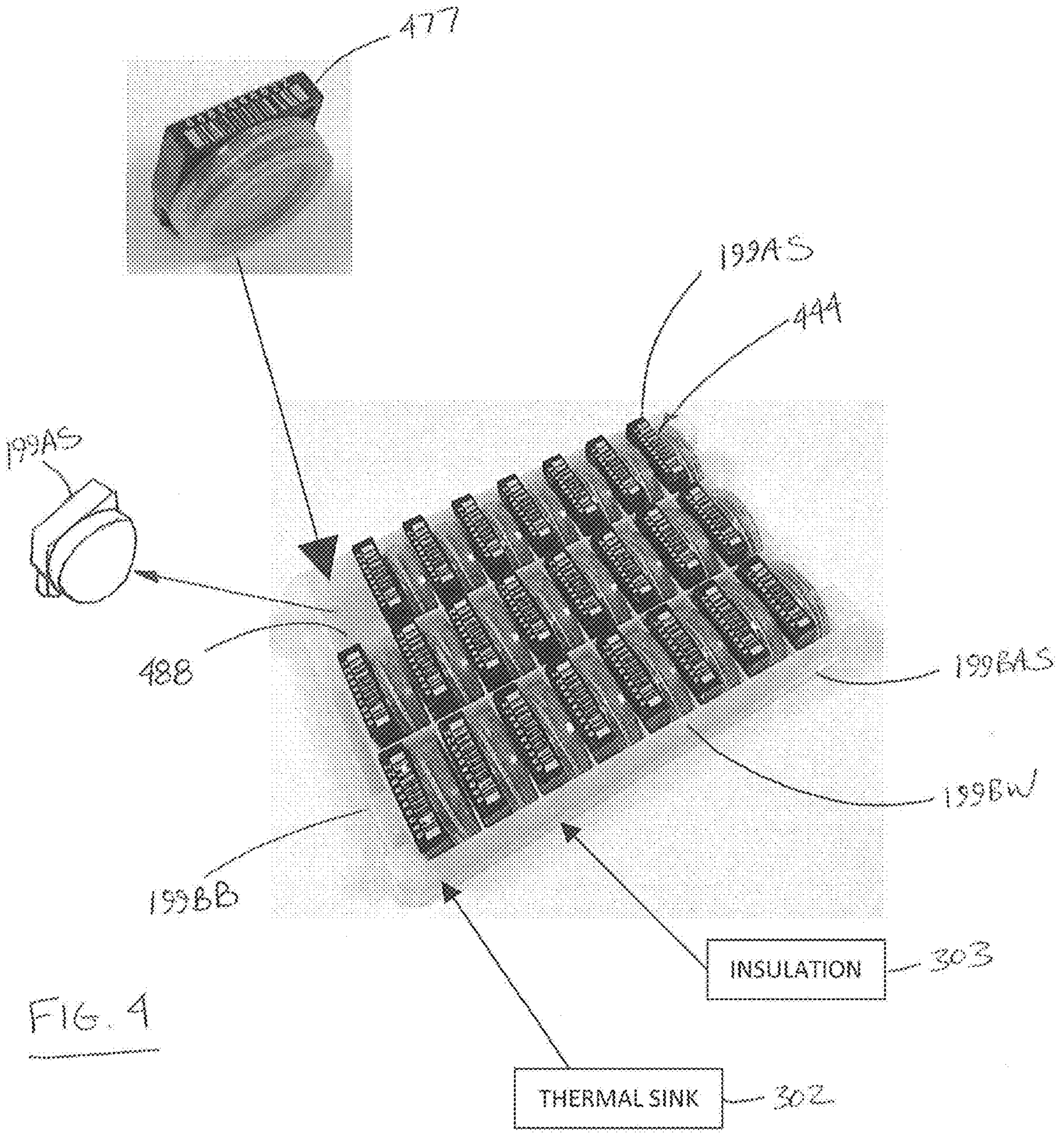
FIG. 4 is an exemplary perspective illustration of a simulacrum labware substitutes and active labware in accordance with aspects of the present disclosure.

The simulacrum sample container units 199AS have a shape and size that simulates the shape and size of one or more of the (active) sample containers/tubes 182A, 182B, 477 (FIGS. 1F and 4). The simulacrum sample container units 199AS are interchangeable with and handled in the same manner as the sample containers/tubes 182A, 182B, 477, within the stores 100A, 100B. As noted above, the simulacrum sample container units 199AS have a thermal mass THm that is an analogue to the thermal mass of a respective containers/tubes 182A, 182B, 477 filled with sample.

Still referring to FIG. 3A, each of the simulacrum labware units 199A (e.g., which include, as described herein, simulacrum tray units 199AT, simulacrum rack units 199AR, simulacrum box units 199AB, and simulacrum sample container units 199AS) include a frame or exterior case 199AF and a thermal sink or thermal mass 301. The frame 199AF houses or is integrally formed the thermal sink 301. The frame 199AF is configured for storage at each of the sample specimen labware storage locations of, for example, the stores 100A, 100B, the storage rack 185 or any other suitable place sample specimen labware units (e.g., active labware units LWU) are stored. As also described herein, the frame 199AF is sized and shaped commensurate with size and shape of a corresponding sample specimen labware unit (e.g., active labware units LWU, active labware devices LWD, etc. described herein) so that the simulacrum labware units 199A and the corresponding sample specimen labware unit are interchangeable with each other at each of the sample specimen labware unit storage locations. The frame 199AF and the thermal sink 301 material are configured so that the simulacrum labware units 199A may be stably stored at room temperature for extended periods of time (e.g., for longer than 6 months or longer than 1 year).

Figure 10:
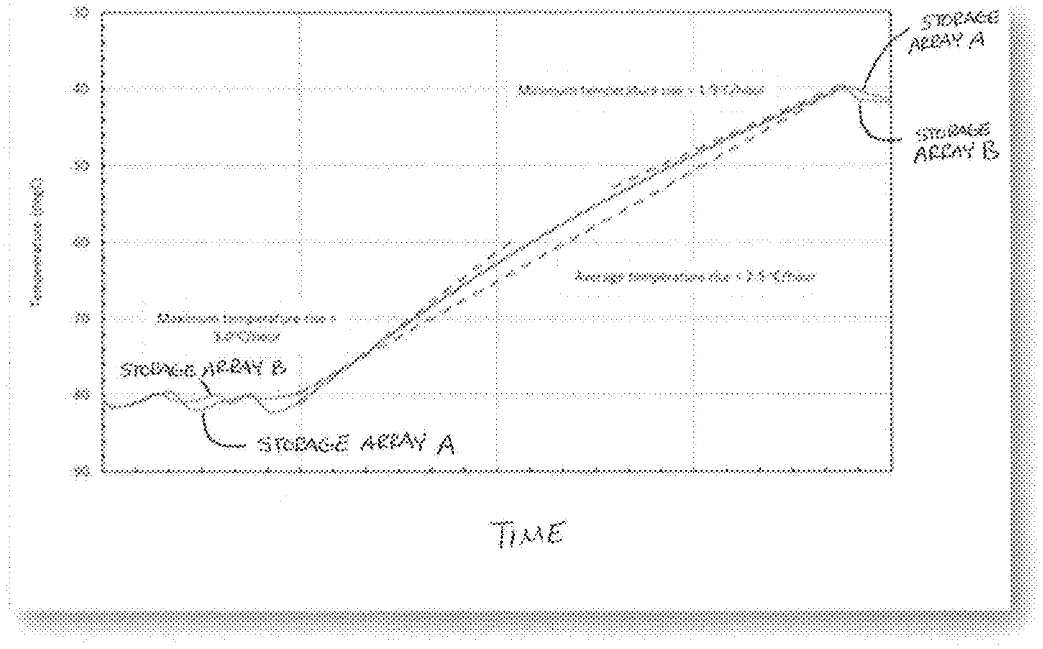
FIG. 10 is an exemplary graph of temperature rise in storage arrays of an automated temperature controlled sample specimen laboratory storage system in accordance with aspects of the present disclosure.

The thermal sink 301 forms a temperature control with the simulacrum labware unit 199A in the temperature controlled sample specimen labware store. As described herein, the frame 199AF and thermal sink 301 provide the simulacrum labware unit 199A with a predetermined thermal characteristic so that the simulacrum labware unit 199A forms a substitute for the corresponding sample specimen labware unit (e.g., active labware units LWU) at each storage location. Here, at each of the storage locations, the simulacrum labware unit 199A and the active labware unit LWU are fungible with respect to the predetermined thermal characteristic, and are swapped as like kind. The thermal sink 301 includes one or more a metal 301M (e.g., aluminum, stainless steel, bismuth, a metal alloy mass, or other suitable metal), a fluid 301F (e.g., which is inclusive of phase change materials such as wax, eutectics, or any other substance that is non-aqueous and non-saline (i.e., a non-aqueous/non-saline substance) that stabilizes temperature of the labware by melting or solidifying to absorb or release heat whenever temperatures are warmer or cooler than the melting point of the substance, and in some aspects aqueous and/or saline substances that do not include biological materials or samples, where the aqueous and/or saline substances being permanently sealed within the exterior case of the simulacrum labware unit and/or device), and a semi-solid material 301S (e.g., a gel such as dimethyl sulfoxide), or any other suitable high thermal mass material (e.g., any suitable material that is characterized by a high heat capacity, high density, and/or low reflectivity (e.g., dark or matte in color) such as, for example, Tylose®). It is noted that high heat capacity refers to the resistance in change to temperature refrigeration purposes and as such high heat capacity materials maintain an average temperature rise within a storage array of less than a temperature rise (e.g., less than about 2° C. per hour) in an empty storage area (see FIG. 10 which illustrates changes in temperature (e.g., maximum, minimum, and average temperature rises) of empty storage arrays A, B in accordance with aspects of the present disclosure, where the storage areas A, B are substantially similar to storage arrays SA described herein).

In one or more aspects, the thermal sink 301 (and other components of the simulacrum labware units 199A described herein) are over-molded by the frame 199AF (i.e., the frame 199AF is molded over and around the thermal sink 301 and/or the other components of the simulacrum labware units 199A described herein so as to encase the thermal sink 301 and other components. In one or more aspects, the frame 199AF may comprise a plastic, metal, composite, or other suitable material. In one or more aspects, both the frame 199AF and the thermal sink 301 comprise a metal such that the frame 199AF forms the thermal sink 301. In other aspects, the thermal sink 301 and/or the other components of the simulacrum labware units 199A are coupled to the frame 199AF in any suitable manner, such as with mechanical and/or chemical fasteners. In some aspects, the thermal sink 301 may be configured for removable insertion into/coupling with an active labware unit LWU.

Figure 5:
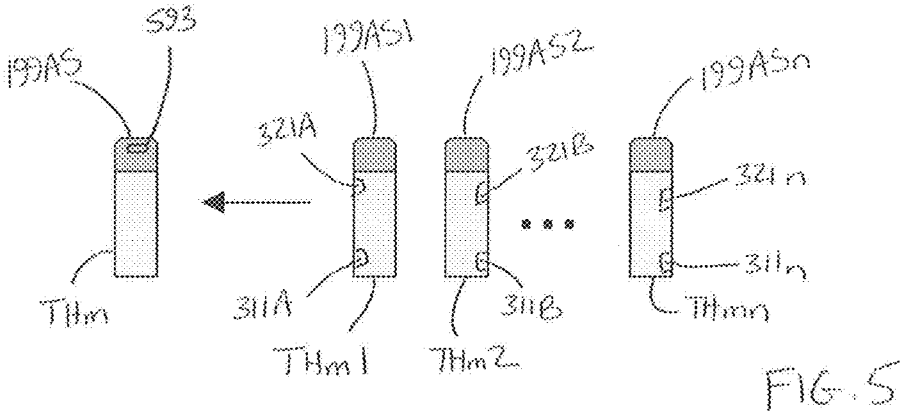
FIG. 5 is an exemplary illustration of a selection of different a simulacrum labware substitutes in accordance with aspects of the present disclosure.

In one or more aspects, also referring to FIG. 5, the simulacrum labware units 199A are selectable from a number of different simulacrum labware units, each having a different characteristic that is different from at least one other simulacrum labware units 199A. For exemplary purposes, the simulacrum sample container units 199AS are selectable from a number of different simulacrum sample container units 199AS1-199ASn (where “n” is a whole number that denotes an upper limit of the number of simulacrum sample container units).

In one or more aspects, the simulacrum labware units 199A of a corresponding active labware unit, is selectable from other different interchangeable simulacrum labware units 199AS1-199ASn each of which corresponds to the active labware unit, and each of the different simulacrum labware units 199AS1-199ASn have a different thermal mass characteristic. For example, each of the different simulacrum sample container units 199AS1-199ASn may have a respective thermal mass THm1-THmn (e.g., inclusive of, for descriptive purposes, thermal conductivities, heat capacities, and/or thermal lag) that is different than a thermal mass THm1-THmn of at least one other simulacrum sample container units 199AS1-199ASn. Here, the different simulacrum sample container units 199AS1-199ASn with different thermal masses THm1-THmn may be selected for placement in the store 100A, 100B so as to vary a thermal profile across a storage array SA of the stores 100A, 100B (e.g., storage arrays SA within the freezer 105A (FIG. 1A), the low temperature storage zones 210A, 210B, or any other suitable location of the store 100A, 100B in which samples are held). For example, simulacrum sample container units 199AS1-199ASn having higher thermal mass (compared to the thermal masses of at least one other simulacrum sample container unit) may be selected for placement in areas of the store 100A, 100B that are not storing or have sparsely stored active labware to increase the thermal load/density in these areas so as to maintain a substantially steady state or substantially uniform (or predetermined) refrigerated thermal inertia (thermal bias) profile (e.g., refrigerated thermal equilibrium), or (thermal bias) gradient in at least one axis across the storage array SA. In some aspects, the thermal lag of one or more of the simulacrum labware substitutes 199 has a configuration that minimizes thermal lag (e.g., the materials of the simulacrum labware substitute 199 maximizes heat absorption as a function of time via the heat capacity and/or heat conductivity of the thermal mass and/or of a material sheathing the thermal mass).

The store 100A, 100B includes a controller 170 that is configured (e.g., programmed with any suitable non-transitory program code) to select an appropriate simulacrum sample container unit 199AS1-199ASn desired for a predetermined location within the store 100A, 100B so as to provide a desired thermal profile for that predetermined location within the store 100A, 100B. For example, the controller 170 is configured to automatically balance a need for heat absorption in the predetermined location(s) with, for example, a weight of the labware units/labware devices by mixing and matching different simulacrum labware units/devices. The controller 170 may also be configured to control a thermal lag in one or more areas of the stores 100A, 100B (such as where there is a lack of active labware). The controller 170 is configured to optimize the temperature profile of the storage arrays SA (or other holding areas of the store 100A, 100B described herein) with the different simulacrum sample container units 199AS1-199ASn so that the temperature profile is substantially the same/uniform throughout the storage array SA. For example, the simulacrum labware substitutes 199 described herein are configured and disposed within the storage array SA so that the simulacrum labware substitute 199 held in each storage location 186, 210SL effects sustainment of refrigerated thermal equilibrium across each other storage location 186, 210SL of the storage array SA separate and distinct from refrigeration of the refrigerated chamber (e.g., such as the freezer 105A and low temperature storage zones 210A, 210B or any of the other refrigerated sample holding locations described herein). As described herein, the at least one simulacrum labware substitute 199 held in each storage location throughout the storage array SA effects thermal bias response, about a thermal equilibrium of the refrigerated chamber (such as those described herein) of the store 100A, 100B, so as to maintain the refrigerated thermal equilibrium throughout the storage array SA. In one or more aspects, different simulacrum sample container units 199AS1-199ASn having at least one of which has different thermal mass than another, are disposed in storage locations (e.g., such as storage location 185, 210SL, 800) of the storage array SA to provide a predetermined refrigerated thermal inertia (thermal bias) profile, or (thermal bias) gradient in at least one axis relative to a predetermined storage location holding the at least one simulacrum sample container units 199AS1-199ASn. The simulacrum labware substitutes 199 effect thermal equilibrium from within the respective storage locations 1186, 210SL holding the simulacrum labware substitutes 199 in swap for holding a corresponding one or more of the active labware unit LWU and active labware device LWD in the storage location.

Still referring to FIG. 3A, in one or more aspects, the simulacrum labware units 199A include instrumentation 311 coupled to, housed within, or otherwise carried by the frame 199AF. The instrumentation 311 is configured to monitor a state of the simulacrum labware unit 199A and/or a state of the store 100A, 100B. For example, the instrumentation 311 includes one or more of a temperature sensor 312, a humidity sensor 313, an inclinometer 314, an accelerometer 315, an image sensor 316, and any other suitable sensors for monitoring environmental, physical, and/or kinematic characteristics of the labware and/or stores. The instrumentation 311 is configured to record data (in any suitable memory) from one or more of the above-noted sensors and or transmit the data in substantially real time to, for example a controller 170 of the store 100A, 100B where the data is employed by the controller 170 to insert or remove simulacrum labware to or from the storage arrays to maintain a predetermined thermal profile within the storage array SA. In one or more aspects, the different characteristics of the different simulacrum sample container units 199AS1-199ASn may be the instrumentation 311A-311*n* carried by the different simulacrum sample container units 199AS1-199ASn. Here, the different simulacrum sample container units 199AS1-199ASn are selected, at least, based on, for example, a characteristic (e.g., temperature, humidity, inclination, vibration, etc.) of the store 100A, 100B (or labware within the store—the labware holding, e.g., the simulacrum labware unit 199AS) that is to be monitored. In one or more aspects, one or more of the simulacrum labware units 199A include both the instrumentation 311 and the thermal sink 301; while in other aspects one or more of the simulacrum labware units 199A include the instrumentation 311 or the thermal sink 301.

In one or more aspects, the different characteristics of the different simulacrum sample container units 199AS1-199ASn may be a fit up and conformance with a gripper of the transport robots within the store 100A, 100B. For example, the different simulacrum sample container units 199AS1-199ASn may have different grip interfaces 321A-321*n* configured to interface with one or more of the transport robots (e.g., rack puller 107A, labware transport robot 130, transport shuttle 212, sample selector module 290, etc.) within the store 100A, 100B. Here, the different simulacrum sample container units 199AS1-199ASn are selected, at least, based on, for example, a predetermined gripper characteristic of the transports handling the different simulacrum sample container units 199AS1-199ASn. For example, in one or more aspects, at least one of the different simulacrum sample container units 199AS1-199ASn includes a ferrous insert 593 (FIG. 5) that provides for magnetic picking/gripping of the at least one of the different simulacrum sample container units 199AS1-199ASn with a magnetic gripper of any suitable transport (such as those noted above, e.g., the tray conveyor external to the sample selector module 290) of the store 100A, 100B.

In one or more aspects, the different characteristics of the different simulacrum sample container units 199AS1-199ASn may be a fit up and conformance with a predetermined interface characteristic of a storage position within a storage array SA of the store 100A, 100B. For example, the different simulacrum tray units 199AT, simulacrum rack units 199AR, simulacrum box units 199AB, and simulacrum sample container units 199AS have respective shapes and sizes so as to fit within and conform with positions within the stores 100A, 100B that correspond with a respective labware which the different simulacrum labware units 199A simulate.

It should be understood that while the simulacrum sample container units 199AS are used in the examples above, the simulacrum tray units 199AT, the simulacrum rack units 199AR, the simulacrum box units 199AB may be similarly configured so as to be selectable from other simulacrum labware units having one or more of the different simulacrum labware unit characteristics (noted above) in the manner described above.

Referring to FIGS. 1A, 2A, 2C, 2D, 2E, 3B, 4, and 6A-9 the multi-state simulacrum labware unit holder 199B have a predetermined characteristic that simulates a predetermined characteristic of active labware. For exemplary purposes, the multi-state simulacrum labware unit holder 199B include, but are not limited to, multi-state simulacrum trays 199BT, multi-state simulacrum racks 199BR, and multi-state simulacrum boxes 199BB. Each of the multi-state simulacrum labware unit holder 199B includes at least one holding receptacle 366 configured to hold respective (active) sample containers/tubes 182A, 182B, 477 (and simulacrum labware units 199A corresponding to the respective sample containers/tubes). As noted above, each multi-state simulacrum labware unit holder 199B has a predetermined characteristic that simulates a respective one of the (active) labware device LWD so that the multi-state simulacrum labware unit holder 199B and the respective labware device LWD are interchangeable with respect to or at each storage location 186, 210SL (FIGS. 1F and 2A) holding the multi-state simulacrum labware unit holder 199B swapped for the respective labware device LWD. Here, in a manner similar to that described above, the predetermined characteristic of the multi-state simulacrum labware unit holder 199B has a first thermal mass characteristic (as described herein) that is an analogue for a second thermal mass characteristic of a respective one of the interchangeable labware devices LWD for which the multi-state simulacrum labware unit holder 199B is a substitute. In other aspects, the predetermined characteristic is any one or more of the characteristics described herein. In one or more aspects, the first thermal mass characteristic and the second thermal mass characteristic are the same in character and/or in magnitude; however, in other aspects the first and second thermal mass characteristics may be different in character and/or in magnitude.

The multi-state simulacrum trays 199BT have a shape and size that simulates the shape and size of (active) sample tray 281 (FIG. 2A), such as an SBS sample tray 372 or other suitable sample holding trays (e.g., multi-well plates) such as described in U.S. Pat. No. 10,481,171 issued on Nov. 19, 2019 (titled "Automated Sample Storage System Having Storage Consumable With Sub-Optimal Storage Density") and U.S. Pat. No. 7,858,044 (titled "Multi-Well Plate Providing A High-Density Storage And Assay Platform") issued on Dec. 28, 2010, the disclosures of which were previously incorporated herein by reference in their entireties. The multi-state simulacrum trays 199BT are interchangeable with and handled in the same manner as the sample tray 281, 372 and the simulacrum tray units 199AT, within the stores 100A, 100B. As noted above, the multi-state simulacrum trays 199ST have a thermal mass THm that is an analogue to the thermal mass of a respective (active) sample tray 281, 372. In one aspect the thermal mass THm is an analogue of the thermal mass of the sample tray 281, 372 without the sample tray 281, 372 filled with active labware units LWU, noting that the multi-state simulacrum trays 199ST are capable of receiving both active labware units LWU and simulacrum labware units 199A.

Figure 7:
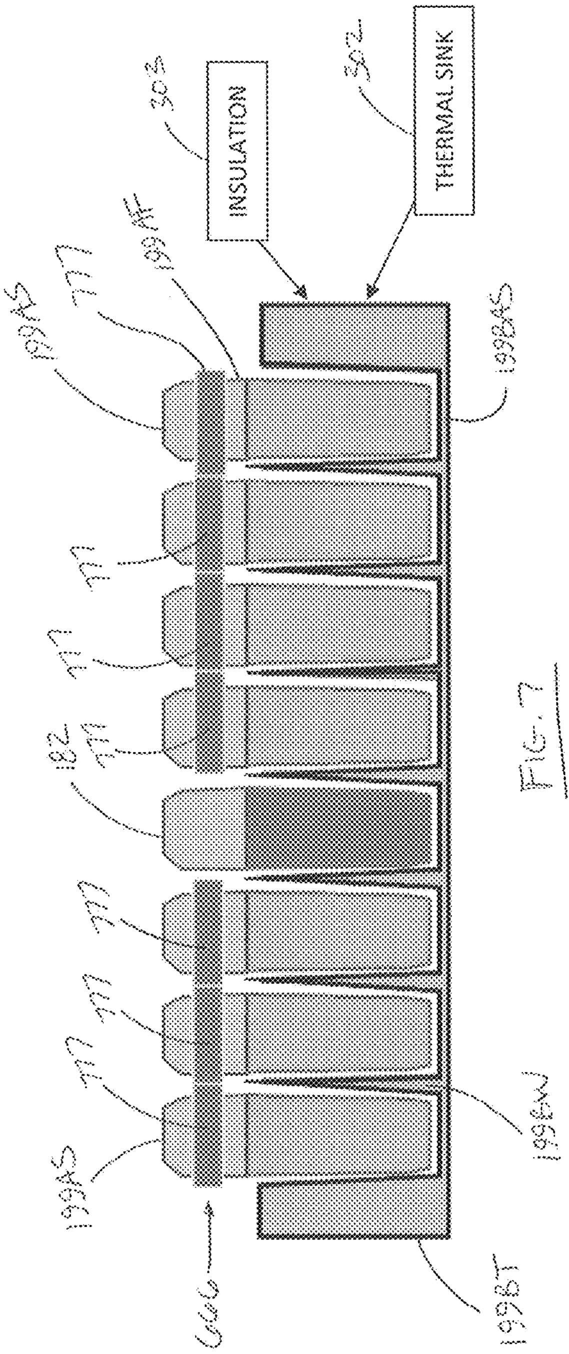
FIG. 7 is an exemplary cross-sectional illustration of the simulacrum labware substitute of FIG. 6A holding one or more of simulacrum labware units and active labware units in accordance with aspects of the present disclosure.
Figure 6B:
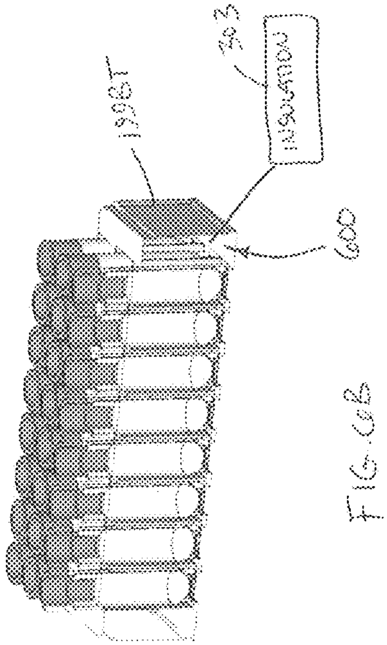
FIG. 6B is an exemplary cross-sectional illustration of the simulacrum labware substitute of FIG. 6A in accordance with aspects of the present disclosure.
Figure 6A:
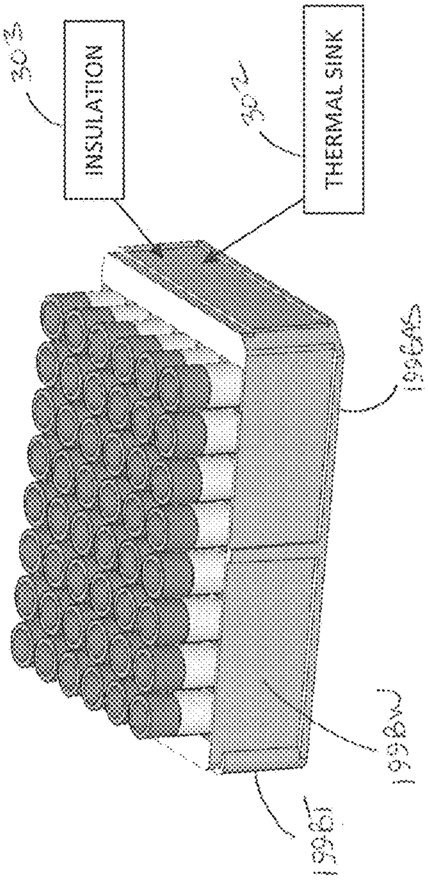
FIG. 6A is an exemplary perspective illustration of simulacrum labware substitute holding one or more of simulacrum labware units and active labware units in accordance with aspects of the present disclosure.
Figure 8:
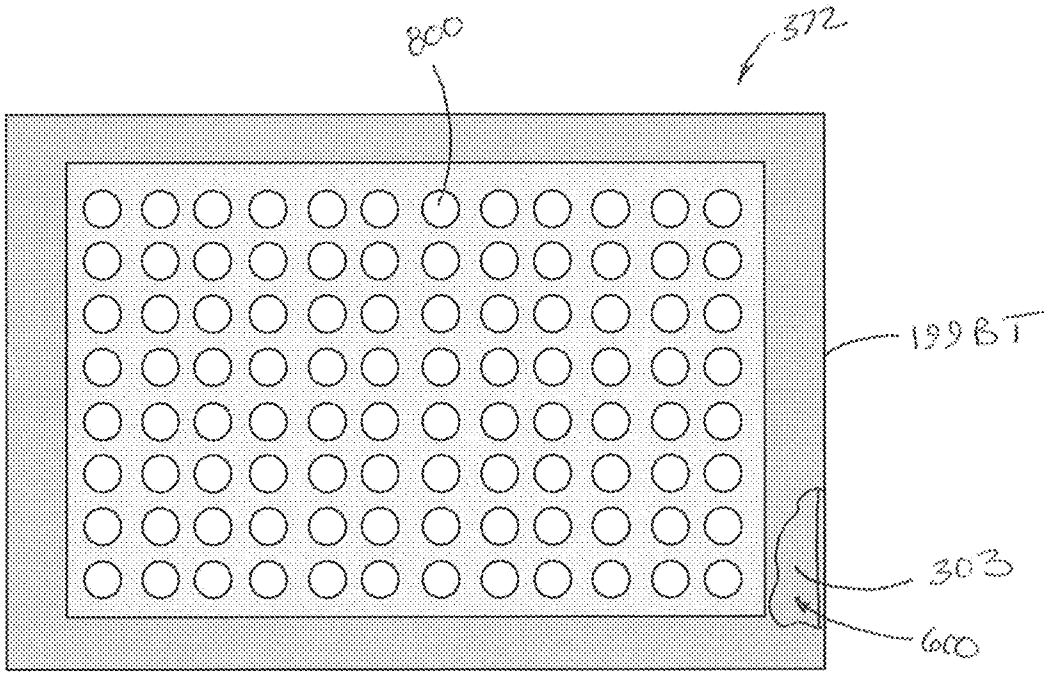
FIGS. 8 and 9 are exemplary plan illustrations of simulacrum labware substitutes in accordance with aspects of the present disclosure.
Figure 9:
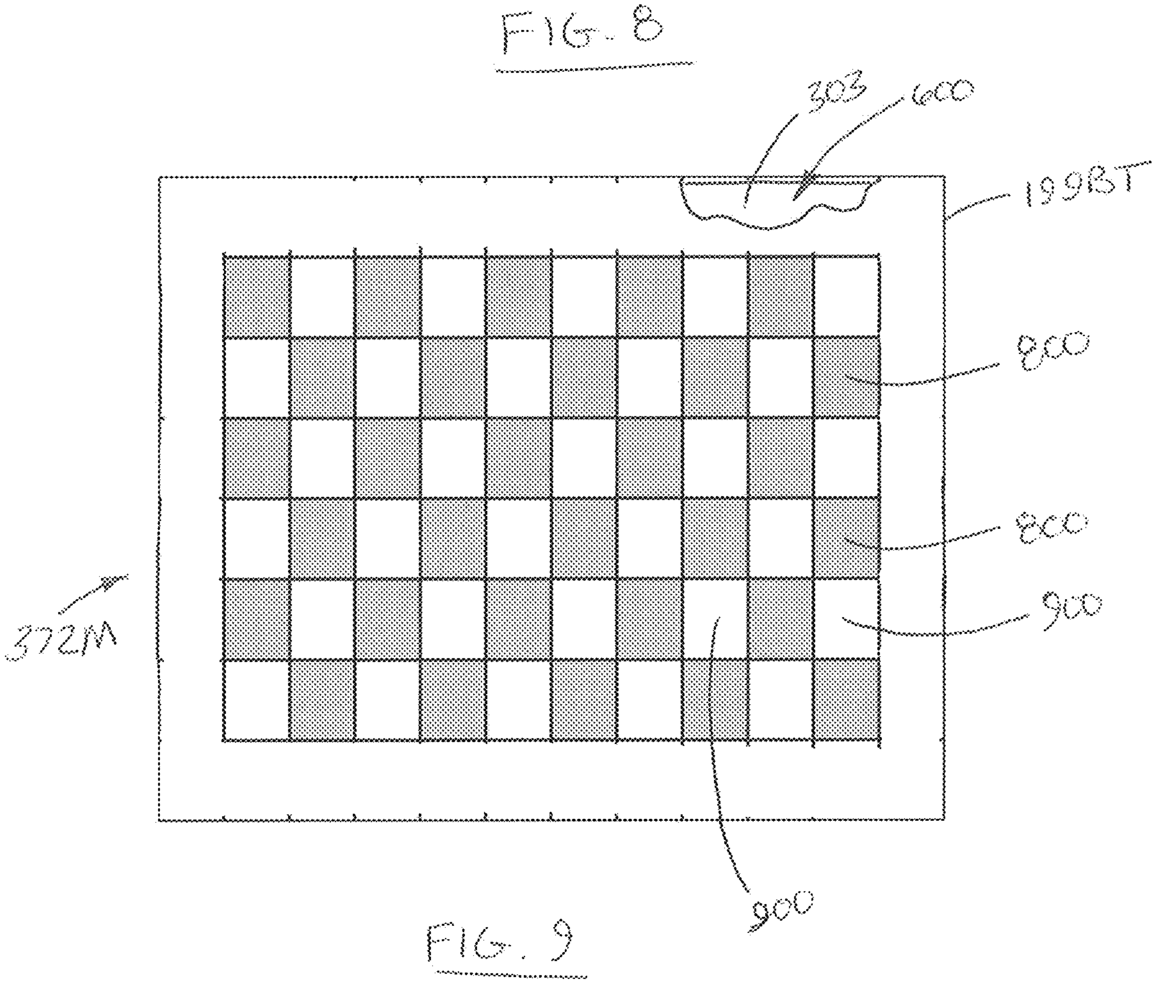

Examples of the multi-state simulacrum trays 199BT are illustrated in, for example, FIGS. 6A-9, where the multi-state simulacrum trays 199BT include one or more of the insulation 303 and thermal sink 302. In FIGS. 6A-8 a multi-state simulacrum tray 199BT is illustrated as a multi-well plate configured to hold sample tubes 182 (also referred to as sample vials) in holding locations 800. While a thermal sink 302 is not illustrated in FIGS. 6A, 6B, and 8, a thermal sink 302 may be provided (as shown in FIG. 7) underneath the holding locations 800 in a base of the multi-well plate. FIG. 9 illustrates a modified (or reduced capacity) multi-well plate 372M that has stanchions 900 disposed between adjacent holding locations 800 so as to define the holding locations 800. Each of the stanchions 900 comprise a thermal sink (which thermal sinks may be in thermal communication with each other). Here, the thermal sink not only provides cooling from underneath the sample tubes 182 but also along the sides of the sample tubes 182 (so as to form a cooling recess that surrounds a labware unit or the simulacrum labware unit 199A on all but one (access) side of the labware unit or the simulacrum labware unit 199A).

The multi-state simulacrum racks 199BR have a shape and size that simulates the shape and size of one or more of the (active) high density racks 370 (FIG. 2C) and the (active) standard density racks 371 (FIG. 2C). The multi-state simulacrum racks 199AR are interchangeable with and handled in the same manner as the high density racks 370, the standard density racks 371, and the simulacrum rack units 199AR within the stores 100A, 100B. As noted above, the multi-state simulacrum racks 199BR have a thermal mass THm that is an analogue to the thermal mass of a respective one of the high density racks 370 and the standard density racks 371. In one aspect the thermal mass THm is an analogue of the thermal mass of the high density rack 370 or the standard density rack 371 without the high density rack 370 or the standard density rack 371 filled with active labware units LWU, noting that the multi-state simulacrum racks 199BR are capable of receiving both active labware units LWU and simulacrum labware units 199A.

Figure 2D:
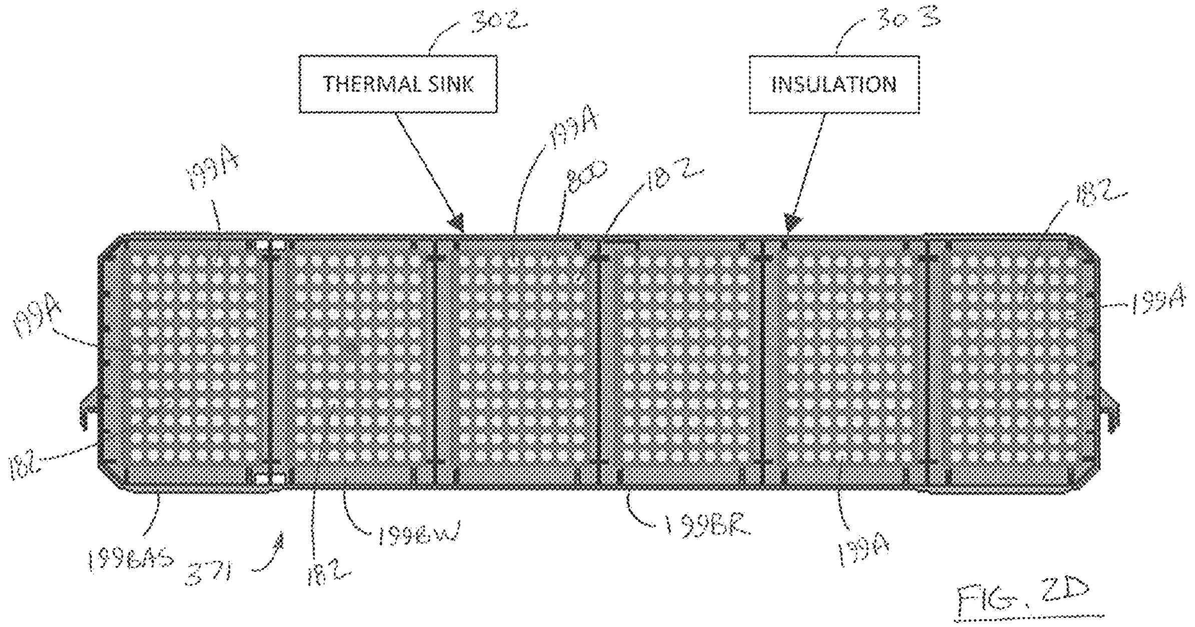
FIGS. 2D and 2E are schematic plan illustrations of portions of the automated temperature controlled sample specimen laboratory storage system of FIG. 2A incorporating aspects of the present disclosure.
Figure 2E:
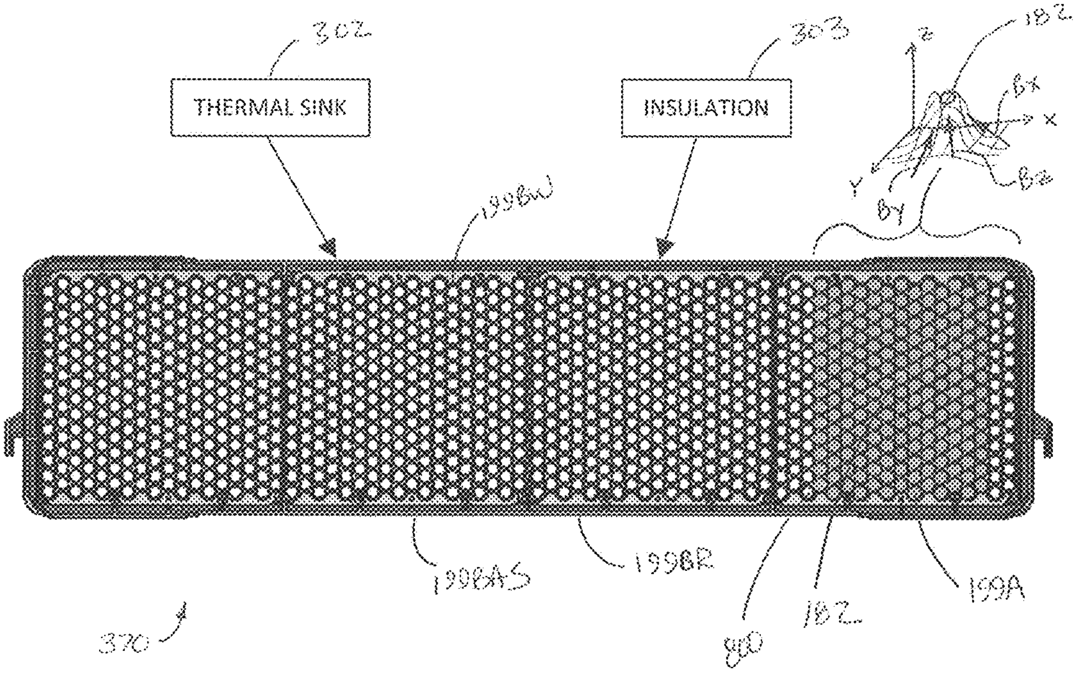

Examples of the multi-state simulacrum racks 199BR are illustrated in, for example, FIGS. 2C-2E, where the multi-state simulacrum racks 199BR include one or more of the insulation 303 and thermal sink 302. Here the multi-state simulacrum racks 199BR are configured as a standard density rack 371 (configured to hold active trays 281, 372, multi-state simulacrum trays 199BT such as those illustrated in FIGS. 6A-9, or simulacrum tray units 199AT) and a high density rack 370 (configured to hold labware units LWU (such as sample tubes 182) and simulacrum sample container units 199AS). The multi-state simulacrum racks 199BR include insulation 303 within an outer peripheral wall (in a manner similar to that illustrated in, e.g., FIG. 6B so as to form an insulating frame around the outermost labware units/simulacrum labware units/simulacrum labware trays held in the rack) and/or a thermal sink 302 located in the base of the multi-state simulacrum racks 199BR The multi-state simulacrum boxes 199BB have a shape and size that simulates the shape and size of one or more of the (active) sample boxes 180A, 180B (FIG. 1F—collectively referred to as sample box 180). The multi-state simulacrum boxes 199BB are interchangeable with and handled in the same manner as the sample boxes 180A, 180B and simulacrum box units 199AB, within the stores 100A, 100B. As noted above, the multi-state simulacrum boxes 199BB have a thermal mass THm that is an analogue to the thermal mass of a respective one of the sample boxes 180A, 180B. In one aspect the thermal mass THm is an analogue of the thermal mass of the sample box 180A, 180B without the sample box 180A, 180B filled with active labware units LWU, noting that the multi-state simulacrum boxes 199BB are capable of receiving both active labware units LWU and simulacrum labware units 199A.

An example of the multi-state simulacrum box 199BB is illustrated in, for example, FIG. 4 where the multi-state simulacrum box 199BB includes one or more of the insulation 303 and thermal sink 302. In FIG. 4 the multi-state simulacrum box 199BB is illustrated as a box configured to hold tissue cassettes 477. In other aspects, the multi-state simulacrum box 199BB may be configured to hold any suitable labware units and/or any suitable simulacrum labware units 199A.

Each of the multi-state simulacrum labware unit holder 199B (e.g., which include, as described herein multi-state simulacrum trays 199BT, multi-state simulacrum racks 199BR, and multi-state simulacrum boxes 199BB) include a frame or exterior case 199BF. The frame 199BF houses or is integrally formed with one or more of a thermal sink or thermal mass 302, insulation 303, and instrumentation 311 in a manner similar to that described above with respect to the simulacrum labware units 199A. In other aspects, the thermal sink 302, insulation, and instrumentation 311 are coupled to the frame 199BF in any suitable manner, such as with mechanical and/or chemical fasteners. The frame 199BF is configured for storage at each of the sample specimen labware storage locations of, for example, the stores 100A, 100B, the storage rack 185 or any other suitable place sample specimen labware devices (e.g., active labware devices LWD) are stored. As also described herein, the frame 199BF is sized and shaped commensurate with size and shape of a corresponding sample specimen labware devices (e.g., active labware devices LWD) so that the simulacrum labware devices 199B and the corresponding sample specimen labware devices are interchangeable with each other at each of the sample specimen labware device storage locations.

The thermal sink 302 forms a temperature control with the simulacrum labware device 199B in the temperature controlled sample specimen labware store. As described herein, the frame 199BF and thermal sink 302 provide the simulacrum labware device 199B with a predetermined thermal characteristic so that the simulacrum labware device 199B forms a substitute for the corresponding sample specimen labware device (e.g., active labware devices LWD) at each storage location. Here, at each of the storage locations, the simulacrum labware device 199B and the active labware device LWD are fungible with respect to the predetermined thermal characteristic, and are swapped as like kind. The thermal sink 302 is substantially similar to thermal sink 301 described above and may form any suitable portion of the multi-state simulacrum labware unit holder 199B including, but not limited to, a base 199BAS and holding receptacle walls 199BW of the multi-state simulacrum labware unit holder 199B. In some aspects, the thermal sink 302 may be configured for removable insertion into/coupling with an active labware device LWD. The insulation 303 may be any suitable insulator having a high thermal mass including, but not limited to, foam, fiberglass, vacuum, and gas. Where the insulation 303 is a vacuum or gas the frame 199BF and/or thermal sink 302 forms a cavity 600 (FIG. 6B) in which the vacuum or gas insulation 303 is disposed. It is noted that vacuum insulation 303 within the multi-state simulacrum labware unit holder 199B may mitigate moisture presence on the multi-state simulacrum labware unit holder 199B. In a manner similar to that described above, in one or more aspects, one or more of the multi-state simulacrum labware unit holders 199B include both the instrumentation 311 and the thermal sink 301; while in other aspects one or more of the simulacrum labware unit holders 199B include the instrumentation 311 or the thermal sink 301. In a manner similar to that described above, the frame 199BF the thermal sink 302, insulation 303 material are configured so that the simulacrum labware devices 199B may be stably stored at room temperature for extended periods of time (e.g., for longer than 6 months or longer than 1 year).

In one or more aspects, the multi-state simulacrum labware unit holder 199B are selectable (in a manner substantially similar to that described above with respect to simulacrum sample container units 199AS1-199ASn) from a number of different multi-state simulacrum labware unit holder 199BS1-199BSn, each having a different characteristic that is different from at least one other simulacrum labware units 199B. For exemplary purposes, the multi-state simulacrum sample labware 199B are selectable from a number of different multi-state simulacrum labware unit holder 199BS1-199BSn (where "n" is a whole number that denotes an upper limit of the number of simulacrum sample container units).

In a manner similar to that noted above, the multi-state simulacrum labware unit holder 199B of a corresponding active labware device LWD, is selectable from other different interchangeable multi-state simulacrum labware unit holders 199BS1-199BSn each of which corresponds to the active labware device LWD, and each of the different multi-state simulacrum labware unit holder 199BS1-199BSn have a different thermal mass characteristic. For example, the different multi-state simulacrum labware unit holder 199BS1-199BSn may have one or more of a respective thermal mass THm1-THmn (that is different than a thermal mass THm1-THmn of at least one other multi-state simulacrum labware unit holder 199BS1-199BSn), respective instrumentation 311A-311*n* (that is different than instrumentation 311A-311*n* of at least one other multi-state simulacrum labware unit holder 199BS1-199BSn—see FIG. 5), a respective grip interface(s) 321A-321*n* (that is different than a grip interface(s) 321A-321*n* of at least one other multi-state simulacrum labware unit holder 199BS1-199BSn—see FIG. 5), and a respective fit up and conformance with a predetermined interface characteristic of a storage position within a storage array SA of the store 100A, 100B (the fit up and conformance being different than at least one other multi-state simulacrum labware unit holder 199BS1-199BSn). The different multi-state simulacrum labware unit holder 199BS1-199BSn are selected for placement within a store in a manner similar to that described above so as to, for example, in conjunction with or in lieu of the simulacrum labware units 199A and/or active labware within the store 100A, 100B, maintain a substantially steady state or substantially uniform (predetermined) refrigerated thermal inertia (thermal bias) profile, or (thermal bias) gradient in at least one axis over the storage array SA of the store 100A, 100B. In one or more aspects, the different multi-state simulacrum labware unit holder 199BS1-199BSn having at least one of which has different thermal mass than another, are disposed in storage locations (e.g., such as storage locations 185, 210SL) of the storage array SA to provide a predetermined refrigerated thermal inertia (thermal bias) profile, or (thermal bias) gradient in at least one axis relative to a predetermined storage location holding the at least one multi-state simulacrum labware unit holder 199BS1-199BSn.

As described above, the multi-state simulacrum labware unit holder 199B is, at least in part, selectably switchable between the active labware state, the simulacrum state, and the mixed (or quasi-active) state. Here, the multi-state simulacrum labware unit holder 199B is switchable between an initial state (i.e., one of the active labware state, the simulacrum state, and the mixed state) to a final state (i.e., another of the active labware state, the simulacrum state, and the mixed state). The controller 170 is configured to select a state of (e.g., selectably switch) each of the multi-state simulacrum labware unit holders 199B between the active labware state, the simulacrum state, and the mixed state (and the controller 170 includes a registry configured to track the change in states of each of the multi-state simulacrum labware unit holders 199B). In the simulacrum state, the multi-state simulacrum labware unit holder 199B holds respective simulacrum labware units 199A. For example, referring to FIG. 4, the multi-state simulacrum box 199BB in the simulacrum state is filled with simulacrum sample container units 199AS (having the form factor of a tissue cassette) so that filled the multi-state simulacrum box 199BB has a thermal mass substantially equivalent to the simulacrum box units 199AB and/or a thermal mass substantially equivalent to an active labware box filled with tissue cassettes (e.g., so as to simulate the active labware box filled with tissue cassettes). Still referring to FIG. 4, the multi-state simulacrum box 199BB in the mixed state has a fixed predetermined number wells 488 holding simulacrum sample container units 199AS, while the remaining number of wells 488 hold active labware (e.g., in this example active tissue cassettes 477). In the active labware state, the multi-state simulacrum box 199B has all of the wells thereof holding active tissue cassettes 477. However, to transition to and from the active labware state from either the simulacrum state or the mixed state, a progressive selection of labware units is performed to change the state of the multi-state simulacrum labware unit holder 199B by adding or removing simulacrum labware units 199A from the multi-state simulacrum labware unit holder 199B.

In one or more aspects the multi-state simulacrum labware units holder 199B held in the storage arrays SA of the stores 100A, 100B (FIGS. 1A, 2A) can all have the same state (i.e., all of the multi-state simulacrum labware unit holder 199B have the state of the active labware state, the simulacrum state, or the mixed state) to effect a single mode of simulacrum operation; while in other aspects the multi-state simulacrum labware units holder 199B held in the storage arrays SA of the stores 100A, 100B (FIGS. 1A, 2A) can have a combination of two of the three states (i.e., two of the active labware state, the simulacrum state, and the mixed state) to effect a dual mode of simulacrum operation; while in still other aspects the multi-state simulacrum labware units holder 199B held in the storage arrays SA of the stores 100A, 100B (FIGS. 1A, 2A) can have a mixture of the active labware state, the simulacrum state, and the mixed state to effect a mixed mode of simulacrum operation. The stores 100A, 100B can be switched between the single mode, dual mode, and mixed mode of simulacrum operation through the addition or removal of multi-state simulacrum labware unit holders 199B having the active labware state, the simulacrum state, and/or the mixed state. As may be realized, the multi-state simulacrum labware units holders 199B (having any one or more of the active labware state, the simulacrum state, and the mixed state) and the simulacrum labware units 199A may be used in combination, within the same storage array SA of the store 100A, 100B, for a further mixed mode of simulacrum operation as illustrated in FIG. 2A.

Referring again to FIGS. 1G and 2A, in one or more aspects, the stores 100A, 100B include, in addition to storage arrays SA, one or more of a simulacrum tempering compartment 142, a simulacrum storage compartment 149, a simulacrum buffer having a temperature of about −20° C. (referred to as −20° C. buffer 147), and a simulacrum buffer having a temperature of about −80° C. (referred to as −80° C. buffer 141). The −20° C. buffer 147 and the −80° C. buffer 141 are configured to hold any suitable number of simulacrum labware substitutes 199 for use in the storage arrays SA so that the simulacrum labware substitutes 199 enter the storage at a predetermined temperature (e.g., about −20° C. or about −80° C.) of the storage array SA. The buffers, e.g., −20° C. buffer 147, the −80° C. buffer 141, or any other suitable buffer held at any suitable temperature, are disposed in any suitable refrigerated chamber (such as the freezer 105A, the transport chamber 110, the intermediate chamber 115, the working chamber 120, transport zone 245 or any other suitable refrigerated chamber of the stores 100A, 100B), for the simulacrum labware substitute, the buffer being separate and distinct from the storage array and each storage location of the storage array. As may be realized, simulacrum labware substitutes 199 may be moved from the −20° C. buffer 147 or the −80° C. buffer 141 to the simulacrum tempering compartment 142 or the simulacrum storage compartment 149. The simulacrum labware substitutes 199 may be moved between the storage arrays SA, the simulacrum tempering compartment 142, the simulacrum storage compartment 149, the −20° C. buffer 147, and the −80° C. buffer 141 by any suitable automation of the stores 100A, 100B, such as transport shuttle 212 and labware transport robot 130.

The simulacrum tempering compartment 142 is configured to temper the simulacrum labware substitutes 199 to or from a predetermined temperature (e.g., about room temperature, about −20° C., or about −80° C.), for example, for introduction or removal of the simulacrum labware substitutes 199 to or from the store 100A, 100B. Once the simulacrum labware substitutes 199 are tempered to, for example, about −20° C. or about −80° C., the tempered simulacrum labware substitutes 199 can be moved directly to a predetermined storage array SA (i.e., the storage array having a temperature substantially the same as the tempering temperature), to one of the −20° C. buffer 147 and the −80° C. buffer 141, or to the simulacrum storage compartment 149.

The simulacrum storage compartment 149 may be a dedicated storage (i.e., without active labware units LWU and without active labware devices LWD) for the simulacrum labware substitutes 199. The simulacrum storage compartment 149 is configured to store the simulacrum labware substitutes 199 at about −20° C. and/or about −80° C. (e.g., the simulacrum storage compartment 149 may have two compartments each at a different one of the about −20° C. and the about −80° C. temperatures). The simulacrum labware substitutes 199 may be moved from the simulacrum storage compartment 149 directly to a storage array SA, to the −20° C. buffer 147, to the −80° C. buffer 171, or to the simulacrum tempering compartment 142.

Figure 1G:
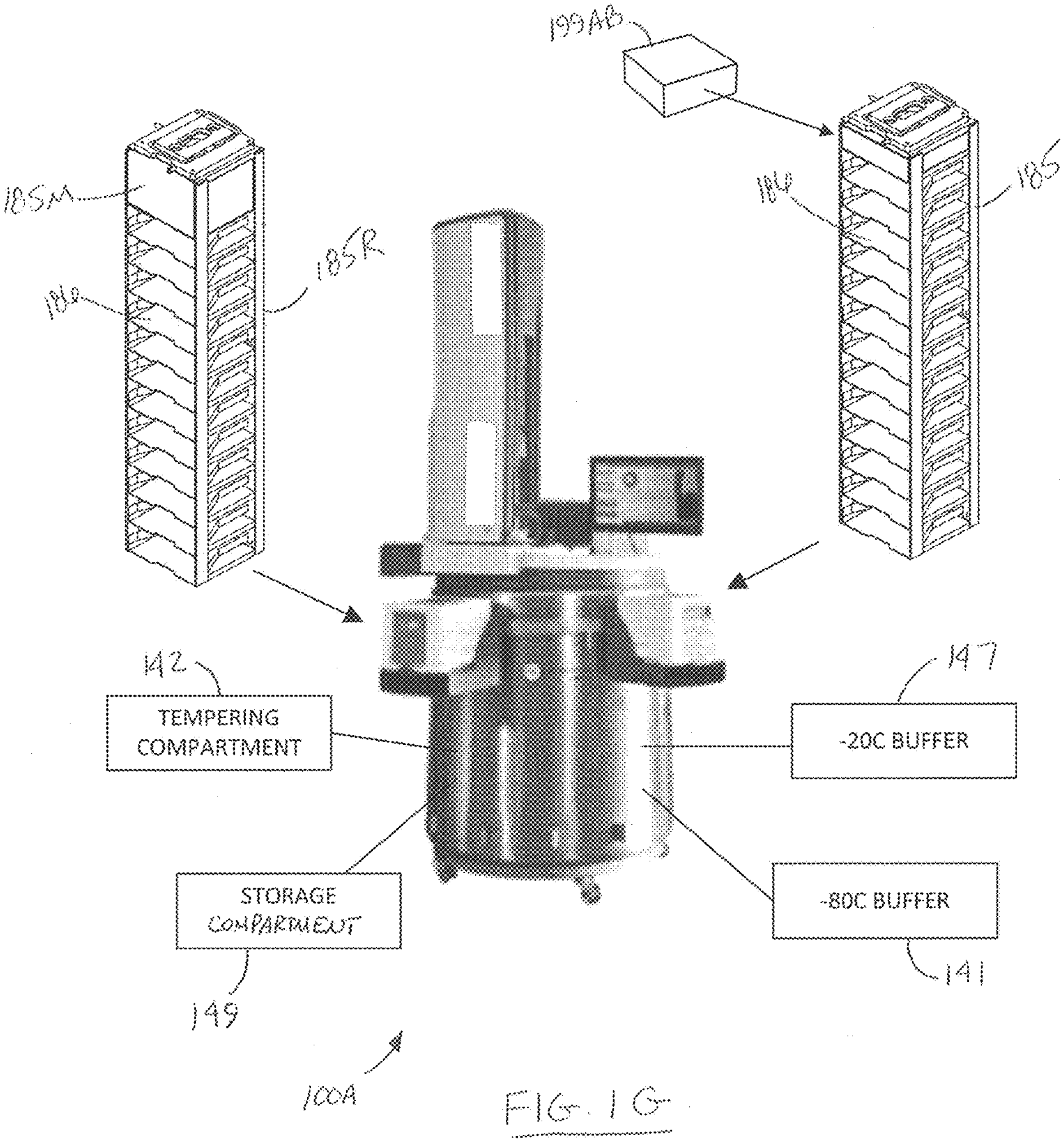
FIG. 1G a schematic perspective illustration of the automated temperature controlled sample specimen laboratory storage system of FIG. 1A incorporating aspects of the present disclosure.

Referring now to FIGS. 1G, 2D, and 2E, as described herein the simulacrum labware units 199A can be inserted and removed from active labware devices LWD and multi-state simulacrum labware unit holders 199B. The simulacrum labware units 199A may be placed within the active labware devices LWD and multi-state simulacrum labware unit holders 199B in areas most affected by heat loss or to thermally protect one or more active labware unit (e.g., the simulacrum labware substitutes 199 may be placed to encircle a location of one or more active labware units/devices within a tray or rack, may be placed to form a thermal perimeter barrier around the perimeter of a tray or rack, and/or may be placed above and/or below active labware in a storage rack 185).

Referring to FIG. 1G, one or more of the simulacrum box units 199AB (or a multi-state simulacrum boxes 199BB filled with simulacrum labware units 199A or an active box filled with simulacrum labware units 199A) is placed at the top of the storage rack 185 (e.g., above active labware held in the storage rack 185) adjacent the port door of the freezer 105A. Here a high thermal mass adjacent the port door (when the port door is opened) may mitigate any thermal effects on samples held in the storage rack 185 as a result of the opening the port door. In other aspects, the high thermal mass 185M may be built into or integral with a top portion of a reduced capacity storage rack 185R (as may be realized, a high thermal mass may be built into or integral with a reduced capacity tray or reduced capacity rack in a manner substantially to that described for the reduced capacity storage rack 185R).

As can be seen in FIG. 2D, the simulacrum labware units 199A are placed in holding locations 800 of the trays held in the standard density rack 199BR (or an active standard density rack) that form an outer perimeter around the rack 199BR. Here the simulacrum labware units 199A surround and form a perimeter thermal barrier for active labware units LWU such as sample tubes 182 (or other suitable active labware units LWU such as those described herein). As can be seen in FIG. 2E, simulacrum labware units 199A are placed in holding locations 800 so as to surround/encircle a sample tube 182 and form a thermal barrier of high thermal mass around the sample tube 182. Different thermal inertia gradients/thermal inertia bias profiles may be formed across storage locations 210SL, 186, 800 of any of the storage arrays described herein. These thermal inertia gradients/thermal inertia bias profiles may be formed along one or more axes of the storage array (e.g., one-dimensional bias profiles, two-dimensional bias profiles, or three-dimensional bias profiles) with respect to desired storage locations within a refrigerated space. For example, an exemplary thermal inertia gradients/thermal inertia bias profile is illustrated in FIG. 2E with respect to the portion of the high density rack 370 holding sample container/tube 182. Here the sample container/tube 182 is inserted into the rack 370 and has a higher temperature than the surrounding simulacrum labware units 199A as shown in the three-dimensional thermal inertia bias profile graph. A thermal bias Bx, By, Bz along one of more axes X, Y, Z if formed so that heat flow is between the sample container/tube 182 and the surrounding simulacrum labware units 199A (and between adjacent simulacrum labware units 199A) so that the thermal bias lowers the temperature of the sample container/tube 182. It is noted that the thermal inertia bias profile graph and the contents thereof illustrated in FIG. 2E are exemplary only and in other aspects the data represented in the graph and the thermal biases generated thereby may have any suitable profile shapes.

Referring to FIG. 7, in one or more aspects, the simulacrum labware units 199A are shaped so that at least one simulacrum labware unit 199A, held in a storage location (e.g., such as storage locations 185, 800, 210SL) and another simulacrum labware unit 199A held in another storage location (such as other ones of storage locations 185, 800, 210SL) communicate with each other over a thermal transfer link so as to cooperate in sustainment of refrigerated thermal equilibrium across each other storage location of the storage array SA separate and distinct from refrigeration of the refrigerated chamber in which the storage locations is disposed. The at least one simulacrum labware substitute 199 held in each storage location throughout the storage array SA effects thermal bias response, about a thermal equilibrium of the refrigerated chamber (such as those described herein) of the store 100A, 100B, so as to maintain the refrigerated thermal equilibrium throughout the storage array SA.

The multi-state simulacrum labware unit holders 199B may also be shaped (in addition to or in lieu of the thermal linking of the simulacrum labware units 199A) so that at least one multi-state simulacrum labware unit holders 199B, held in a storage location (such as storage locations 185, 210SL) and another multi-state simulacrum labware unit holders 199B held in another storage location (such as other ones of storage locations 185, 210SL) communicate with each other over a thermal transfer link so as to cooperate in sustainment of refrigerated thermal equilibrium across each other storage location of the storage array SA separate and distinct from refrigeration of the refrigerated chamber in which the storage locations is disposed. For example, a simulacrum labware substitute 199 may be thermally coupled to at least one other simulacrum labware substitutes 199 in any suitable manner so that the thermal mass of simulacrum labware substitutes 199 is increased by virtue of the thermal coupling of more than one simulacrum labware substitute 199. For example, referring to simulacrum sample container units 199AS for exemplary purposes only, the simulacrum labware substitute 199 include a thermal bridge component 777 (or thermal transfer link) that radiates or otherwise peripherally extends from the frame 199AF (or frame 199BF with respect to the multi-state simulacrum labware unit holder 199B) of a respective simulacrum labware substitute 199. The thermal bridge component 777 is sized so that with simulacrum labware substitutes 199 (each having a respective thermal bridge component 777) placed in adjacent holding locations (e.g., within a storage array, within a rack, within a tray, etc.) the thermal bridge components 777 of the adjacent simulacrum labware substitutes 199 substantially abut/contact each other to create a heat transfer conduit (or thermal bridge) 666 between the adjacent simulacrum labware substitutes 199. Here the collective of thermally coupled simulacrum labware substitutes 199 has a higher thermal mass than the individual simulacrum labware substitutes 199. In the example illustrated in FIG. 7, the thermal bridge 666 may extend around/encircle the sample tube 182. As may be realized, the substantial abutting contact of the bridge components 777 and the separability of one bridge component 777 from another adjacent bridge component 777 (e.g., provided by the substantial abutting contact) maintains the ability of the store 100A, 100B to handle individual simulacrum labware units 199A (such as the simulacrum sample container units 199AS) and individual active labware units (such as sample tubes 182 and cassettes 477). The multi-state simulacrum labware unit holders 199B may include thermal bridge components substantially similar to thermal bridge component 777 described above.

Still referring to FIG. 7 and to FIG. 3, in one or more aspects, a grid of simulacrum labware units 199A (e.g., with or without the bridge components 777), such as for exemplary purposes only, simulacrum sample containers 199AS, may be inserted into a conventional active labware device (e.g., such as an SBS tray, box, rack, etc.) so that the conventional active labware device is converted into a simulacrum labware substitute. As an example, the simulacrum sample containers 199AS may be inserted into an active labware tray in a manner substantially similar to the placement of the stanchions 900 in FIG. 9 so that the converted active labware device holds a combination of active and simulacrum labware units. In other aspects, the simulacrum sample containers 199AS may be inserted into an active labware tray so that the converted active labware device holds only simulacrum labware units 199A.

Figure 11A:
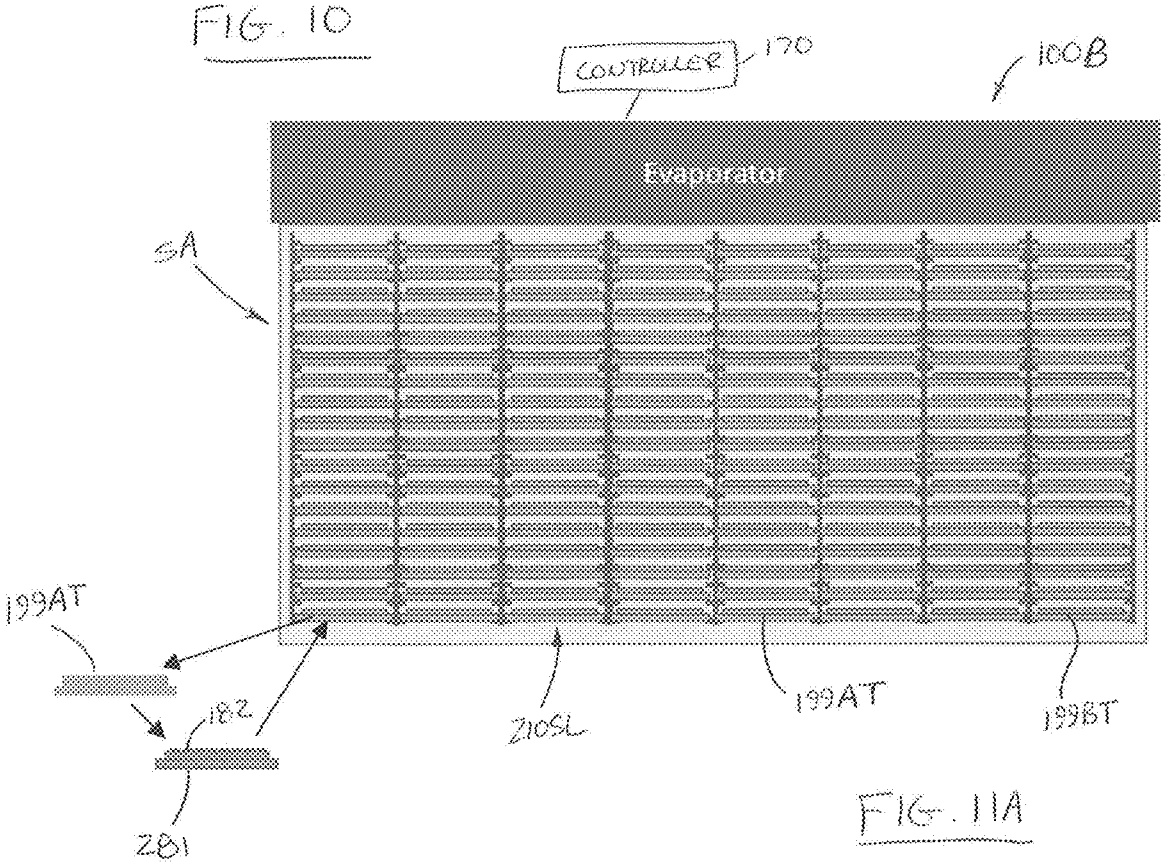
FIG. 11A is an exemplary schematic illustration of a storage array of the automated temperature controlled sample specimen laboratory storage system of FIG. 2A in accordance with aspects of the present disclosure.
Figure 11B:
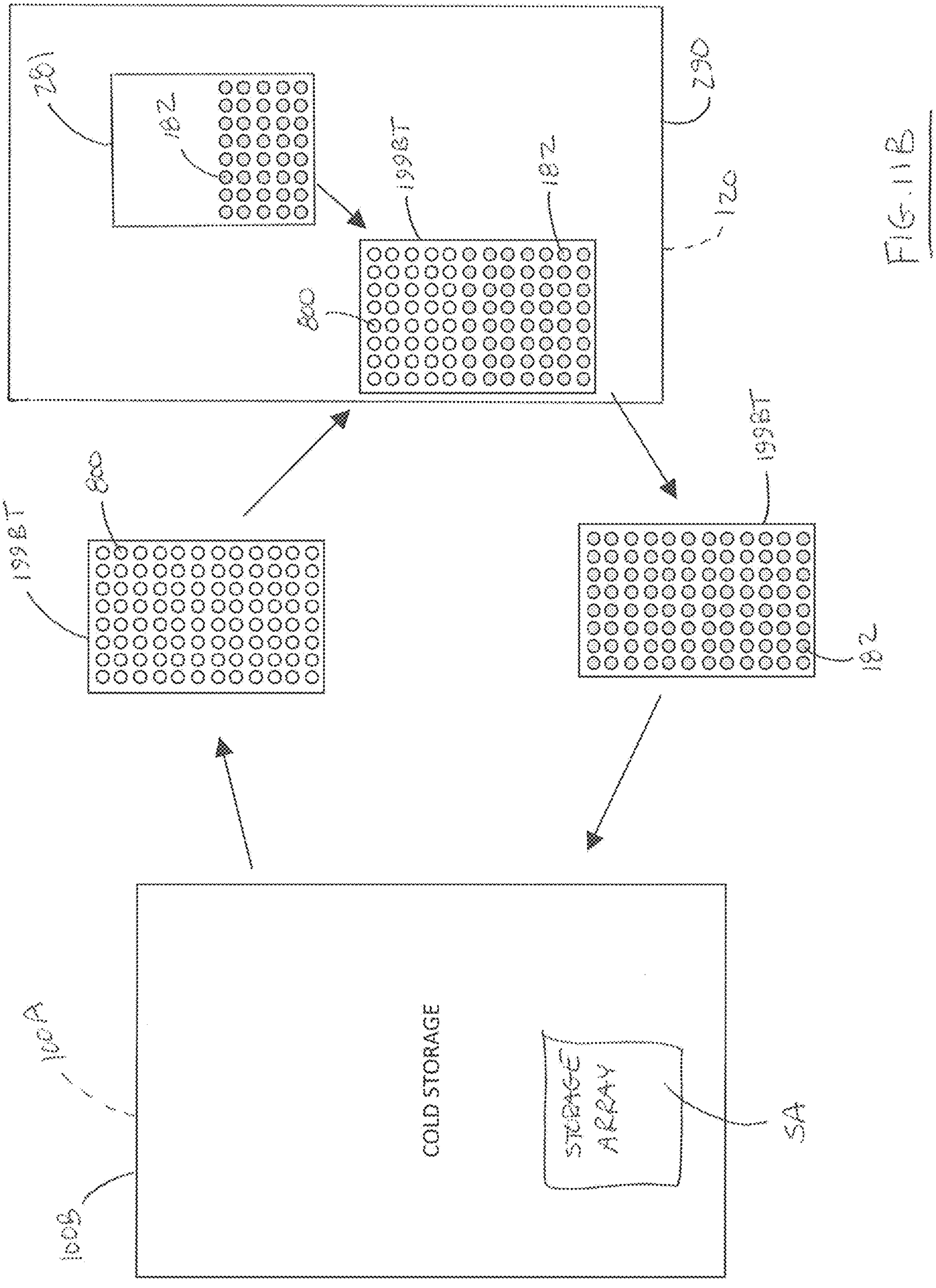
FIG. 11B is an exemplary schematic illustration of an active labware and simulacrum labware substitute swap in a storage array of the automated temperature controlled sample specimen laboratory storage system of FIGS. 1A and 2A in accordance with aspects of the present disclosure.
Figure 18:
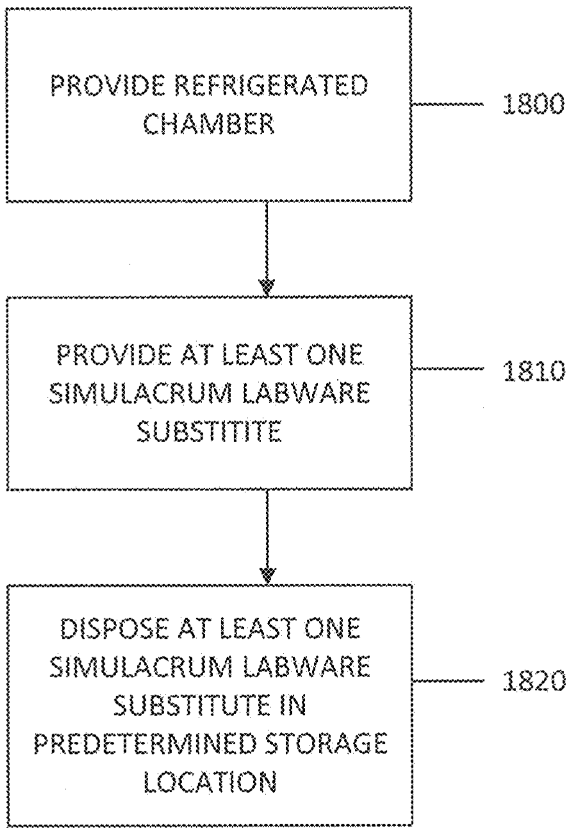

Referring to FIGS. 11A and 11B an exemplary operation of the store 100B will be described, noting that the operation of store 100A is substantially similar. In accordance with the aspects of the present disclosure, a refrigerated chamber is provided (FIG. 18, Block 1800). The refrigerated chamber includes a storage array therein having predetermined storage locations. The predetermined storage locations define a predetermined capacity of one or more of labware unit storage and labware device storage of the storage array, where the storage array has a predetermined area. Each of the storage locations is also configured for holding therein at least one of the one or more of the labware units LWU and labware devices LWD per storage location at a refrigerated thermal equilibrium.

At least one simulacrum labware substitute 199 is provided (FIG. 18, Block 1810). The at least one simulacrum labware substitute 199 has a predetermined characteristic that simulates a corresponding one of the one or more of the labware units LWU and labware devices LWD so that the at least one simulacrum labware substitute 199 and the corresponding one of the one or more of the labware units 199A and labware devices 199B are interchangeable with respect to each storage location holding the at least one simulacrum labware substitute 199 swapped for the corresponding one of the one or more of the labware units LWU and labware devices LWD. For example, in one or more aspects, each of the at least one simulacrum labware substitute 199 has a predetermined thermal mass THm analogous with that of each of the at least one of the one or more labware units LWU and labware devices LWD, and the at least one simulacrum labware substitute 199 and the at least one of the one or more of the labware units LWU and the labware devices LWD are interchangeable at each storage location (such as those described herein) for holding the one or more of the labware units LWU and the labware devices so that the at least one of the one or more labware units LWU and labware devices LWD and the at least one simulacrum labware substitute are swapped for each other at the storage location. The at least one simulacrum labware substitute 199 is disposed in at least one of the predetermined storage locations within the storage array SA (FIG. 18, Block 1820) so that the predetermined capacity of the one or more of the labware unit storage and the labware device storage of the storage array, of predetermined area, is unconstrained by the at least one simulacrum labware substitute held in the at least one predetermined storage location. The at least one simulacrum labware substitute 199 held in each storage location (such as those described herein) throughout the storage array SA effects predetermined thermal inertia bias so as to maintain refrigerated thermal equilibrium, via thermal inertia bias, throughout the storage array SA separate and distinct from refrigeration of the refrigerated chamber.

Upon installation of the store 100B the store is filled (e.g., pre-loaded) with simulacrum labware substitutes 199. For example, the store includes a storage area SA having predetermined storage locations 210SL configured to store active sample trays 281. At installation of the store 100B, simulacrum store units 199AT and/or multi-state simulacrum trays 199BT are inserted/pre-loaded into the storage array SA so that each of the predetermined storage locations 210SL is holding simulacrum labware substitutes 199. Here the simulacrum labware substitutes 199 in each of the predetermined storage locations 210SL maximizes the thermal capacity of the storage array SA (e.g. by filling the storage array with a thermal mass substantially equivalent to a thermal mass of the storage array filled to a maximum capacity with samples) so that a uniform temperature is present throughout the storage array SA. The thermal mass of the simulacrum labware substitutes 199 also provides for a slower rate of storage array SA heating in the event of a loss of power or loss of refrigeration.

Figure 19:
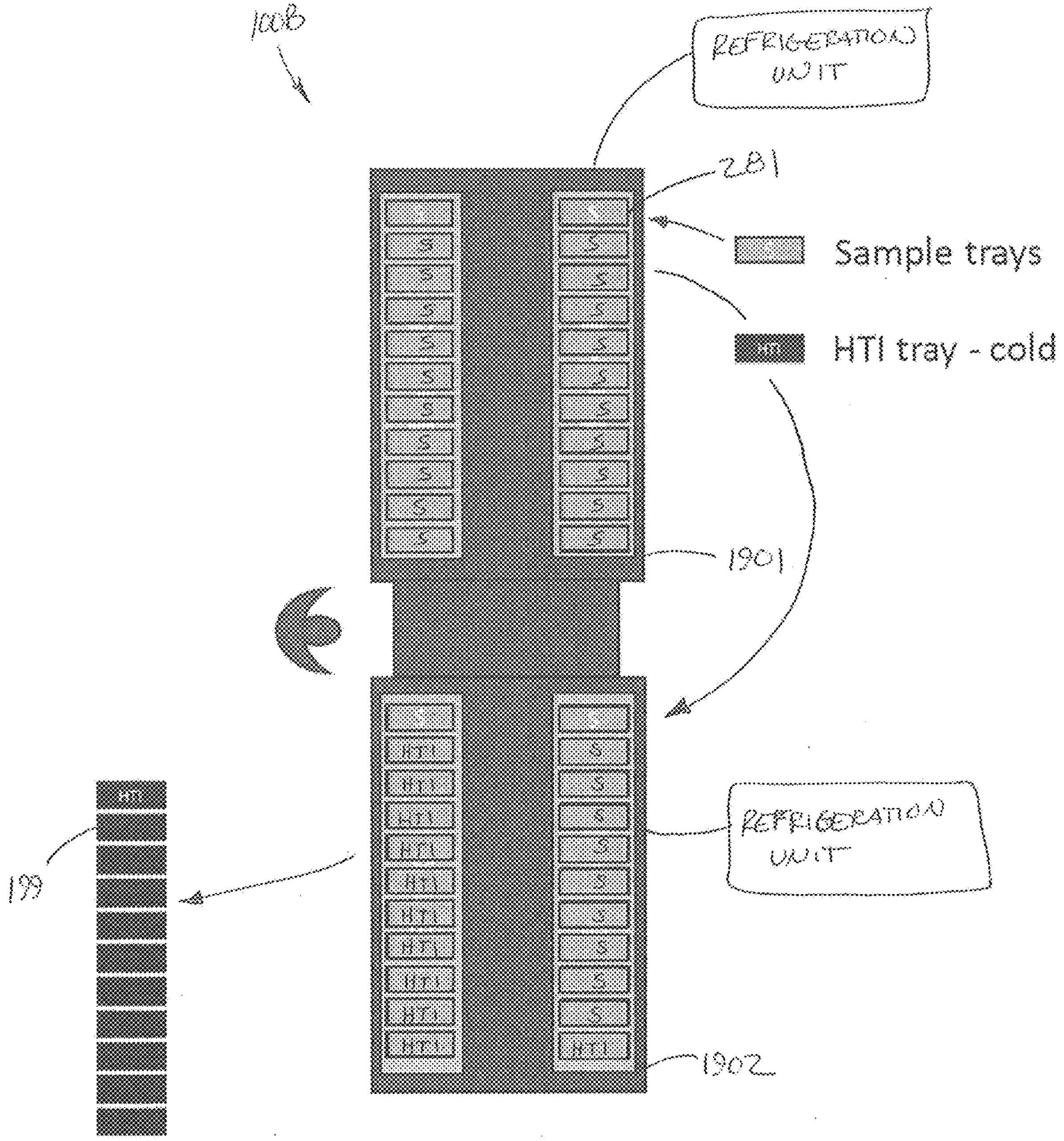
FIG. 19 is a schematic illustration of a multi-bank automated temperature controlled sample specimen laboratory storage system incorporating aspects of the present disclosure.
Figure 22:
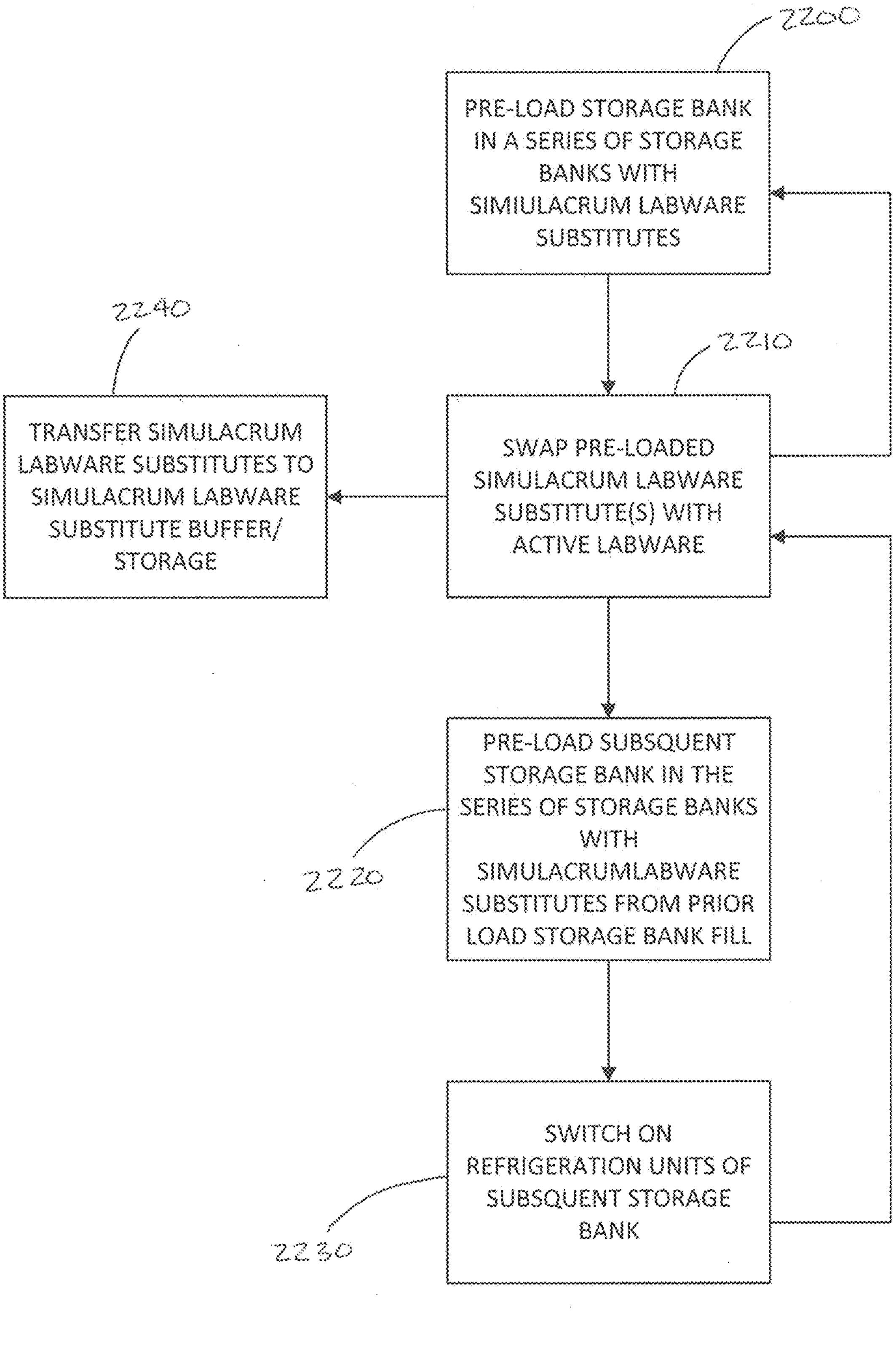
FIG. 22 is a flow chart of an exemplary method incorporating aspects of the present disclosure.

In one aspect, referring also to FIGS. 19 and 22, the store 100B includes multiple independently operated (e.g., independently cooled) storage banks 1901, 1902 that are isolatable from each other. Each of the storage banks 1901, 1902 are substantially similar to those described herein. In a manner similar to that noted above, the controller 170 is configured to effect (e.g., includes any suitable non-transitory program code that effects control of the herein mentioned storage systems to) pre-load each storage bank 1901, 1902 with simulacrum labware substitutes 199 prior to production use of the storage banks 1901, 1902 as described herein. In one or more aspects, the storage banks 1901, 1902 may be pre-loaded with the simulacrum labware substitutes 199 to pre-load fill respective storage banks 1901, 1902, with simulacrum labware substitutes, in series so that the respective storage banks 1901, 1902 are pre-loaded to develop a desired high thermal density and high thermal inertia (e.g., the high thermal density and high thermal inertia being commensurate/analogous to the thermal density and thermal inertia of corresponding active labware) in the respective storage banks 1901, 1902 as needed in advance of or just prior to storage of active labware (such as active sample trays 281 or any other suitable active labware) in each respective storage bank 1901, 1902. For example, storage bank 1901 may be pre-loaded with simulacrum labware substitutes 199 immediately prior (so as to generate the desired high thermal density and high thermal inertia within the given storage bank, where the generated desired high thermal density and high thermal inertia may not require total fill of each storage location throughout the storage bank; rather, a lesser number than total (e.g., 50%, 75%, 80% or any other suitable percentage preload with simulacrum labware substitutes that are evenly distributed through the storage locations of the storage bank) may be sufficient to provide the desired thermal response (e.g., desired predetermined rate of temperature change without refrigeration and desired thermal profile steady state across the storage locations of the storage bank)) to insertion of active labware (FIG. 22, Block 2200) while storage bank 1902 remains empty with refrigeration units to storage bank 1902 in a low power mode or switched off (i.e., in an unused or dormant state so that storage bank 1902 has minimum or no refrigeration). As sample trays 281 are loaded into storage bank 1901 (e.g., in the manner described herein) so that the simulacrum labware substitutes 199 are swapped with active labware (FIG. 22, Block 2210), the simulacrum labware substitutes 199 from storage bank 1901 are transferred to storage bank 1902 (with the refrigeration units of storage bank 1902 remaining off) (FIG. 22, Block 2220). It is noted that the transfer of the simulacrum labware substitutes 199 to the storage bank 1902 is separate and distinct from any transfer of simulacrum labware substitutes 199 to a buffer or storage location (as described herein) dedicated to simulacrum labware substitutes 199. As storage bank 1901 approaches “full” capacity, the refrigeration unit for storage bank 1902 is switched on (FIG. 22, Block 2230) so as to refrigerate the simulacrum labware substitutes 199 previously transferred to storage bank 1902 from storage bank 1901 so as to bring storage bank 1902 to a substantially steady state or substantially uniform temperature distribution as described herein. As may be realized, as active labware is transferred into storage bank 1902 (e.g., so that the simulacrum labware substitutes are swapped with the active labware—FIG. 22, Block 2210), the simulacrum labware substitutes 199 are removed from storage bank 1902 and transferred to any suitable location, such as other storage banks of the store 100B or any suitable buffer/storage location as described herein (FIG. 22, Blocks 2210 and 2240). For example, where there are multiple storage banks (e.g., storage sections), the pre-loading of the multiple storage sections occurs in series, storage section by storage section, until the last storage section in the sequence is filled (e.g., with the simulacrum labware substitutes 199 from the last storage section, substituted by the insertion of active labware into the last storage section, being transferred to a simulacrum labware substitute storage/buffer (as described herein) or to another store). It should also be realized that while the sequential storage bank to storage bank preloading is described with respect to store 100B, such sequential preloading may be applied to any suitable store having multiple storage banks, such as store 100A.

The pre-loading of simulacrum labware substitutes 199 in the storage banks 1901, 1902 is according to a programmed load sequence of the active labware (e.g., the pre-loading of simulacrum labware substitutes 199 is a cascaded/sequenced loading of the load sections/storage banks that conform to a predetermined load sequence of active labware in the load sections/storage banks). For example, as noted above, preloading of a next designated load section or storage bank to be loaded with active labware (in the example above, storage bank 1902) is initiated once the instant load section or storage bank (in the example above, storage bank 1901) is complete. Here, a high thermal capacity preload step immediately precedes a load sequence with simulacrum labware substitutes 199 released from a prior load section/storage bank fill.

In one or more aspects, the transfer of the simulacrum labware substitutes 199 from storage bank 1901 to storage bank 1902 is a balanced load out (e.g., swap) of simulacrum labware substitutes 199. For example, a swap rate of active labware to simulacrum labware substitutes 199 is a 1:1 ratio where for one active labware transferred into, e.g., storage bank 1901 a corresponding one of the simulacrum labware substitutes 199 is removed from the storage bank 1901 and transferred to storage bank 1902. However, in other aspects, the ratio of the load out of simulacrum labware substitutes 199 may be a 1:n ratio where “n” is any suitable number of simulacrum labware substitutes 199. For example, for one active labware transferred into, e.g., storage bank 1901 a corresponding two of the simulacrum labware substitutes 199 is removed from the storage bank 1901 and transferred to storage bank 1902 for a load out ratio of 1:2.

The controller 170 is configured to track placement of each simulacrum labware substitute 199 (i.e., the controller tracks which simulacrum labware substitutes 199 is placed in which storage location 210SL) in any suitable manner. As an example, each simulacrum labware substitutes 199 includes any suitable indicia 444 (see FIG. 4) that identifies the simulacrum labware substitutes 199. The controller 170 includes a matrix correlating the simulacrum labware substitutes 199 to the storage locations 210SL based on the indicia 444. In one aspect, the indicia 444 comprises a barcode, number serialization, or other suitable identifying indicia (e.g., RFID tags, etc.) that can be read by any suitable reader and conveyed by the reader to the controller 170.

Insertion of for example, active sample trays 281 filled (or partially filled) with sample tubes is performed by substituting one of the simulacrum labware substitutes 199 with the active sample tray 281. As an example, referring also to FIG. 2A, the active sample tray 281 is inserted into the store 100B through the input/output module 230. The transport shuttle 212 transports the active sample tray 281 to a predetermined storage location 210SL. The transport shuttle 212 removes the simulacrum labware substitute 199 from the predetermined storage location 210SL and then inserts the active sample tray 281 into the predetermined storage location 210SL. The simulacrum labware substitute 199 may be transported to one of the simulacrum tempering compartment 142, the simulacrum storage compartment 149, the −20° C. buffer 147), or the −80° C. buffer 141). In other aspects, the simulacrum labware substitute 199 may be transported out of the store 100B.

In one or more aspects, active samples such as held in sample tubes 182 or cassettes 477 are inserted into the storage array where the active samples do not fill an entire tray 281 or are to be transferred to a simulacrum labware device 199, such as a multi-state simulacrum labware unit holder 199B, to maintain a predetermined quality of the sample where the placement of the samples in the simulacrum labware device 199 may decrease the time it takes for the sample to reach low temperatures (e.g., "freeze time") and provide for increased consistency with respect to the freeze time as the storage array SA is held at a substantially uniform low temperature across the storage array SA as noted above. For example, the heat capacity of the simulacrum labware device 199 effects a temperature drop of the sample that is both uniform and quick compared to freezing the sample in an active tray or rack within the storage array SA.

Figure 14:
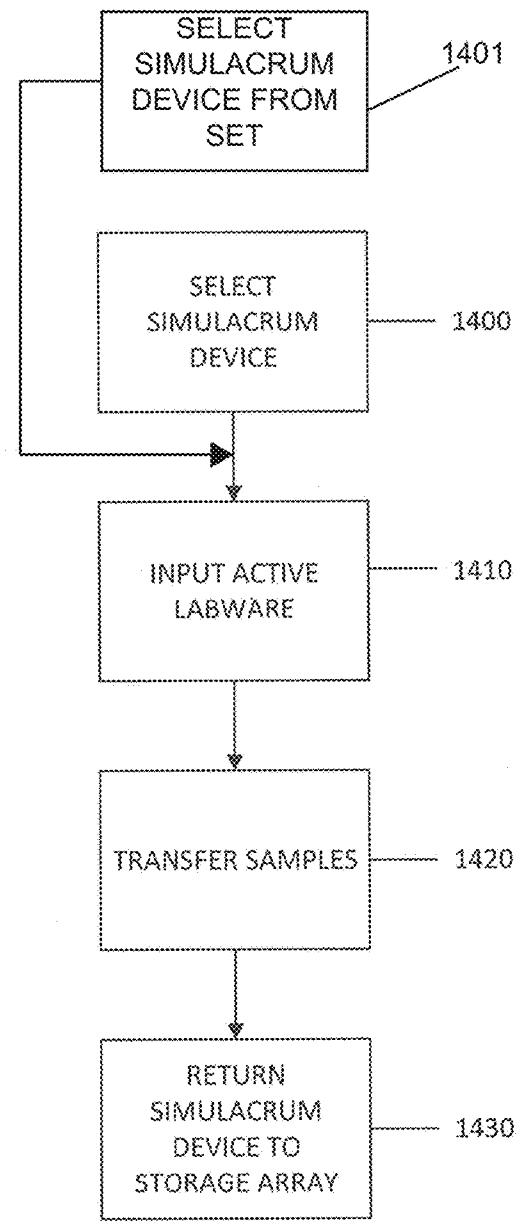
FIGS. 14-18 are flow chart of exemplary methods incorporating aspects of the present disclosure.

Referring to FIGS. 2A, 11B, and 14 (and to sample tubes 182, multi-state simulacrum trays 199BT (trays can be high density or standard density), and active sample tray 281), to transfer individual samples into the storage array SA the controller 170 selects a simulacrum device, such as a multi-state simulacrum tray(s) 199BT, from the storage array SA (FIG. 14, Block 1400) and effects transfer of the multi-state simulacrum tray(s) 199BT to, for example, the sample selector module 290. Where, for example, the simulacrum device is part of a set of simulacrum devices (such as set SLSB—see FIG. 3B), the controller 170 selects the simulacrum device from the set of simulacrum devices SLSB (FIG. 14, Block 1401). Active labware, such as the active sample tray 281, is input to the store 100B (FIG. 14, Block 1410) through, for example the input/output module 230 and transferred to the sample selector module 290 (such as with the transport shuttle 212). The sample selector module 290 transfers the samples 182 (FIG. 14, Block 1420) from the active sample tray 281 to the multi-state simulacrum trays 199BT in a manner that is substantially similar to that described in U.S. Pat. No. 9,630,775 (titled "Sample Selector") and issued on Apr. 25, 2017, the disclosure of which was previously incorporated herein by reference in its entirety. With a desired number (or all) of the samples 182 transferred to the multi-state simulacrum trays 199BT, the transport shuttle 212 transfers/returns the filled multi-state simulacrum tray 199BT to the storage array SA (FIG. 14, Block 1430). Removal of the samples 182 from the storage array SA occurs in substantially a reverse manner to that describe above.

Figure 15:
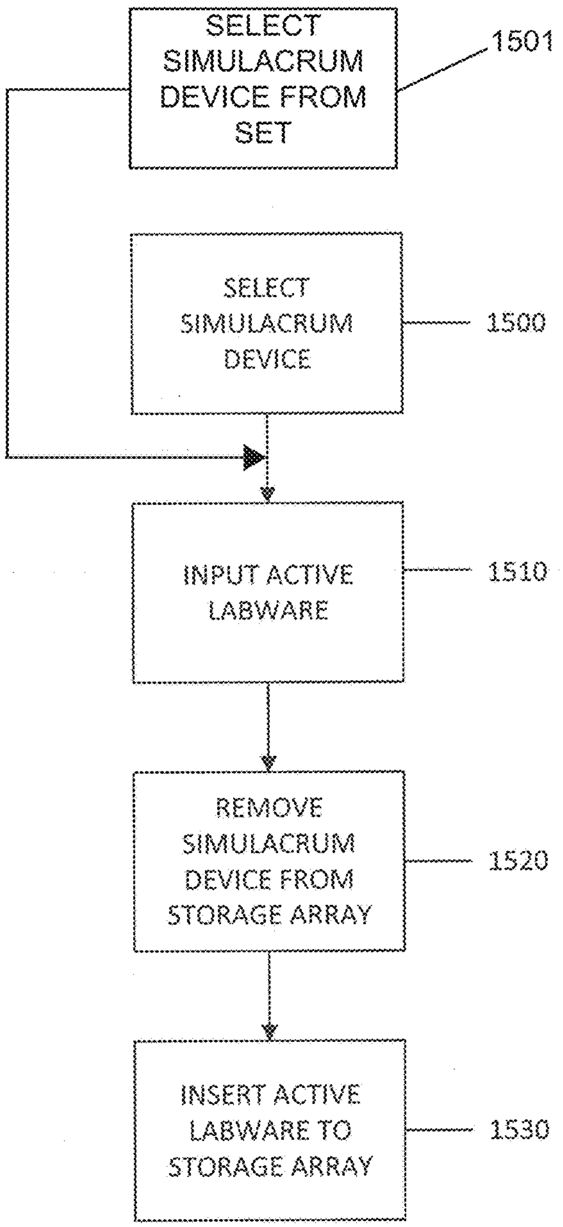

Referring to FIGS. 2A, 11B, and 15, where an active sample tray 281 filled to a maximum capacity with samples 182 (i.e., referred to as a "filled active sample tray") is to be input to the storage array SA, rather than transfer samples from the filled sample tray 281 to a multi-state simulacrum tray 199BT the filled active sample tray 281 may entirely replace/substitute a selected one of the multi-state simulacrum tray 199BT (which as described herein may be part of a set of simulacrum devices SLSB) in the storage array SA. Here the controller 170 may select (for replacement/substitute) a simulacrum labware device 199 (FIG. 15, Block 1500, 1501), such as multi-state simulacrum tray 199BT, that is surrounded by other multi-state simulacrum trays 199BT or filled active sample trays 281. Active labware, such as the filled active sample tray 281, is input to the store 100B (FIG. 15, Block 1510) in a manner similar to that described above. The selected multi-state simulacrum tray 199BT is removed from the storage array SA (such as with the transport shuttle 212) (FIG. 15, Block 1520) and the filled active sample tray 182 is inserted to the storage array SA in the place of the just removed multi-state simulacrum tray 199BT (FIG. 15, Block 1530) so that other multi-state simulacrum trays 199BT or filled active sample trays 281 surrounding the just input filled active sample tray 182 within the storage array SA at least in part effect a quick and uniform cooling (as described above) of the samples 182 within the just input filled active sample tray 182. Removal of the filled active sample tray 281 from the storage array SA occurs in a substantially reverse manner to that described above where a multi-state simulacrum tray 199BT or simulacrum tray units 199AT is substituted for the just removed filled active sample tray 281 in the storage array SA.

Figure 11C:
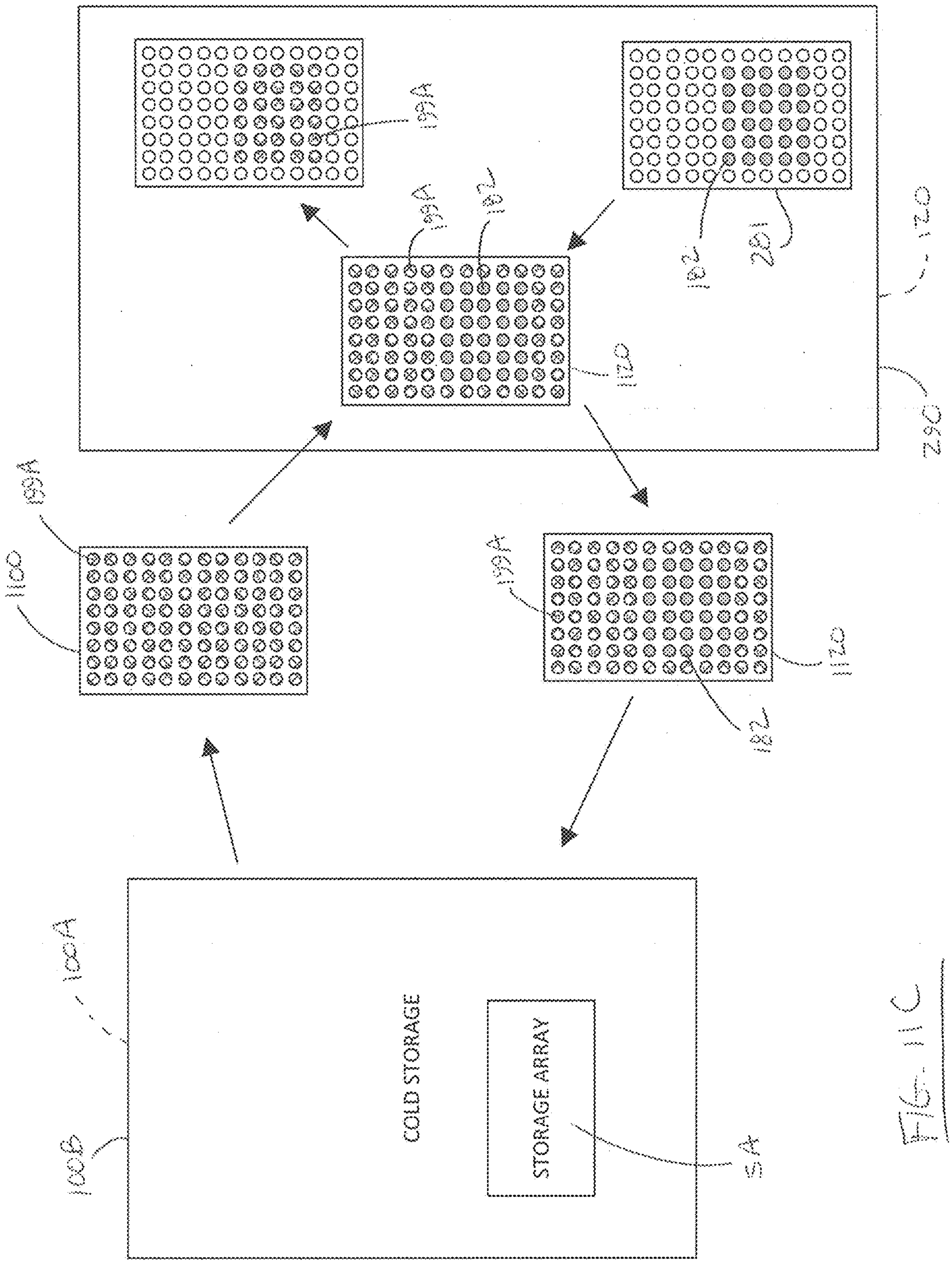
FIG. 11C is an exemplary schematic illustration of an active labware and simulacrum labware substitute swap in a storage array of the automated temperature controlled sample specimen laboratory storage system of FIGS. 1A and 2A in accordance with aspects of the present disclosure.
Figure 16:
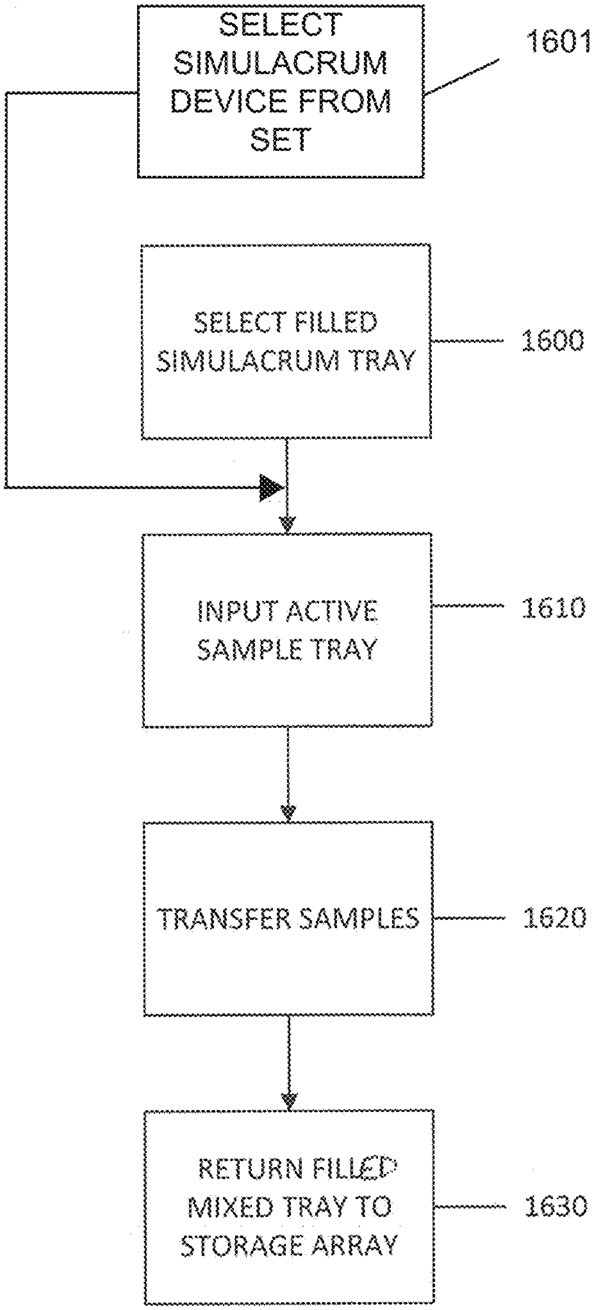

Referring to FIGS. 2A, 11C, and 16, in one or more aspects, the multi-state simulacrum trays 199BT are filled with simulacrum sample container units 199AS to further increase the thermal mass of the simulacrum labware held in any given storage location 210SL of the storage array SA; while in other aspects, an active tray 281 is filled with simulacrum sample container units 199AS to simulate the thermal mass of a filled active sample tray 281 (i.e., filled to a maximum capacity with samples) in any given storage location 210SL of the storage array SA. Here, regardless of whether the multi-state simulacrum trays 199BT filled with simulacrum sample container units 199AS and/or the active sample tray 281 filled with simulacrum sample container units 199AS (e.g., collectively referred to for purposes of this example as "filled simulacrum trays") is/are employed, one or more active samples may be transferred to the storage array SA so as to replace or substitute a respective one or more of the simulacrum sample container units 199AS in the filled trays. The trays, now containing both simulacrum sample container units 199AS and active samples are referred to as "filled mixed trays."

The controller 170 selects a filled simulacrum tray 1100 (FIG. 16, Block 1600) from the storage array SA and effects transfer of the filled simulacrum tray 1100 to, for example, the sample selector module 290. Where, for example, the simulacrum tray 1100 is part of a set of simulacrum devices (such as set SLSB—see FIG. 3B), the controller 170 selects the simulacrum tray 1100 from the set of simulacrum devices SLSB (FIG. 16, Block 1601). The active sample tray 281 is input to the store 100B (FIG. 16, Block 1610)

through, for example the input/output module 230 and transferred to the sample selector module 290 (such as with the transport shuttle 212). The sample selector module 290 removes a simulacrum labware unit(s) 199A, such as simulacrum sample container unit(s) 199AS, from the filled simulacrum tray 1100 and replaces/substitutes (e.g., swaps) the simulacrum labware unit(s) 199A with a sample 182 from the active sample tray 281 (FIG. 16, Block 1620). As may be realized, the simulacrum tray 1100 with the simulacrum labware unit(s) 199AS held therein may be provided as a set, or part of a set, such that the sample selector module 290 removes and replaces one or more of the simulacrum sample containers 199AS (i.e., as a granular unit of the set as described herein) with the samples 182. The removed simulacrum sample containers 199AS may be placed in a respective tray for storage in a cold store, such as buffer 147, 141; while in other aspects the simulacrum sample containers 199AS may be removed from the store 100B. With a desired number (or all) of the samples 182 transferred a state of the filled simulacrum tray 1100 has changed from a simulacrum state to a mixed state, and the tray is now referred to as the filled mixed tray 1120. The transport shuttle 212 transfers/returns the filled mixed tray 1120 to the storage array SA (FIG. 16, Block 1630).

The controller 170 may replace the simulacrum labware units 199A located in the center of the filled simulacrum tray (as opposed to the peripheral edge of the filled tray) so that the samples 182 transferred to the filled mixed tray 1120 are surrounded or otherwise encircled by the simulacrum labware units 199A remaining in the filled mixed tray 1120. Here, the remaining simulacrum labware units 199A effect a quick and uniform cooling of the samples 182 in the manner described above. When individual samples 182 are removed from the store 100A, 100B, the samples 182 are removed from the filled mixed tray 1120 and replaced/substituted with a simulacrum labware unit 199A in a manner substantially opposite to that described above so that the thermal capacity of the store 100A, 100B remains at a maximum thermal capacity as described above.

While the above example shows (FIG. 11C) the simulacrum labware units 199A being transferred to a tray other than the active sample tray 281, in other aspects the simulacrum labware units 199A may be transferred to the active sample tray 281 from which the active samples 182 are picked. It should be understood that while trays were used in the above example, any of the simulacrum labware devices, simulacrum labware units, active labware devices LWD, and active labware units LWU described herein may be employed.

The substituting of the simulacrum sample container units 199AS with individual active labware units LWU (such as sample tubes 182 and cassettes 477) and vice versa may be effected in a two-step transfer or a single step transfer. In the two-step transfer, one of the simulacrum sample container unit 199AS and the active labware unit is picked from a first tray and placed in a second tray and then the other of the simulacrum sample container unit 199AS and the active labware unit is picked from a third tray (or the second tray) and placed in the first tray. The two step transfer may be performed with the sample selector module 290 in a manner substantially similar to that described in U.S. Pat. No. 9,630,775 (titled "Sample Selector") and issued on Apr. 25, 2017, the disclosure of which was previously incorporated herein by reference in its entirety.

Figure 12A:
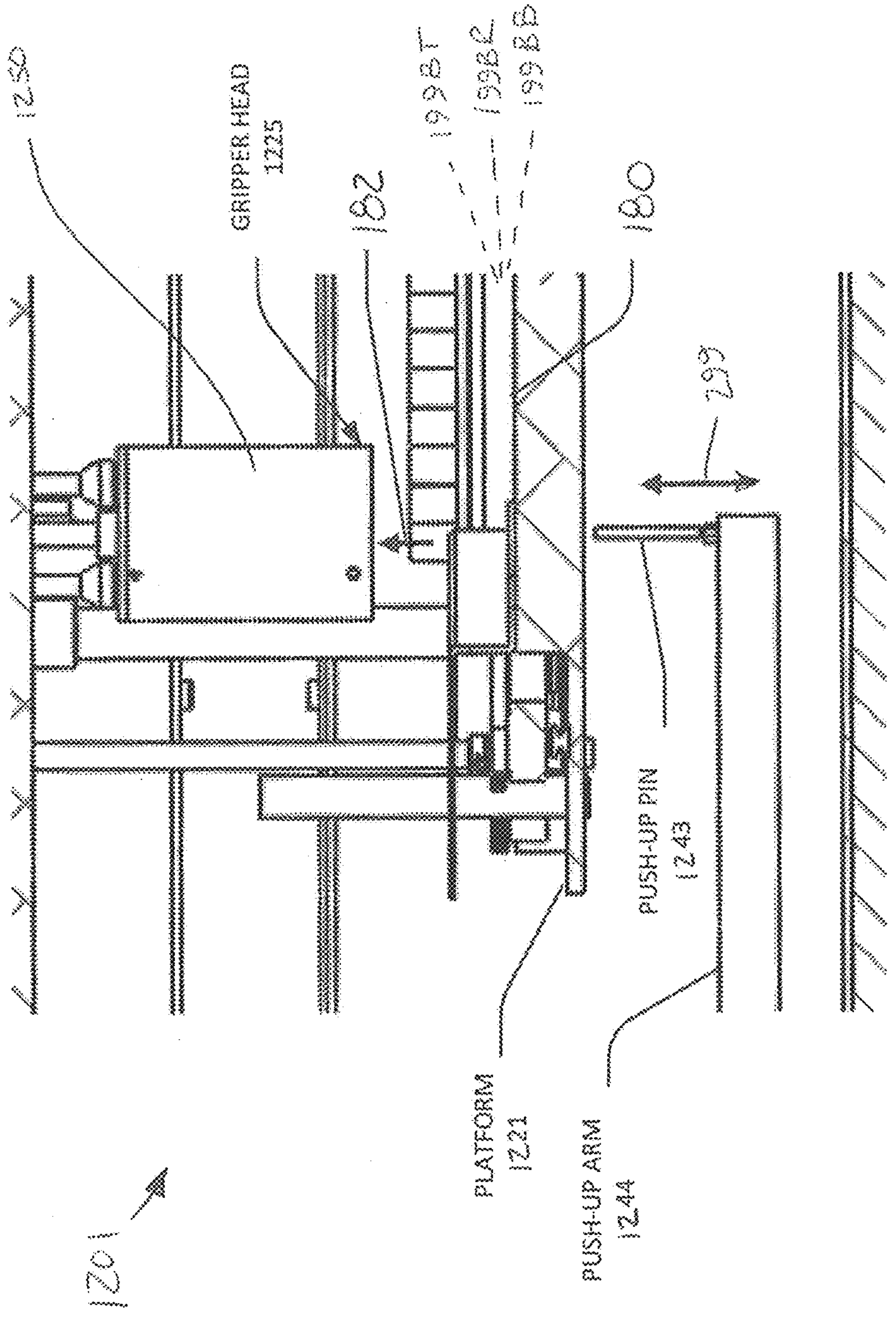
FIG. 12A is an exemplary schematic illustration of a portion of an automated transport of the automated temperature controlled sample specimen laboratory storage system of FIGS. 1A and 2A in accordance with aspects of the present disclosure.
Figure 12B:
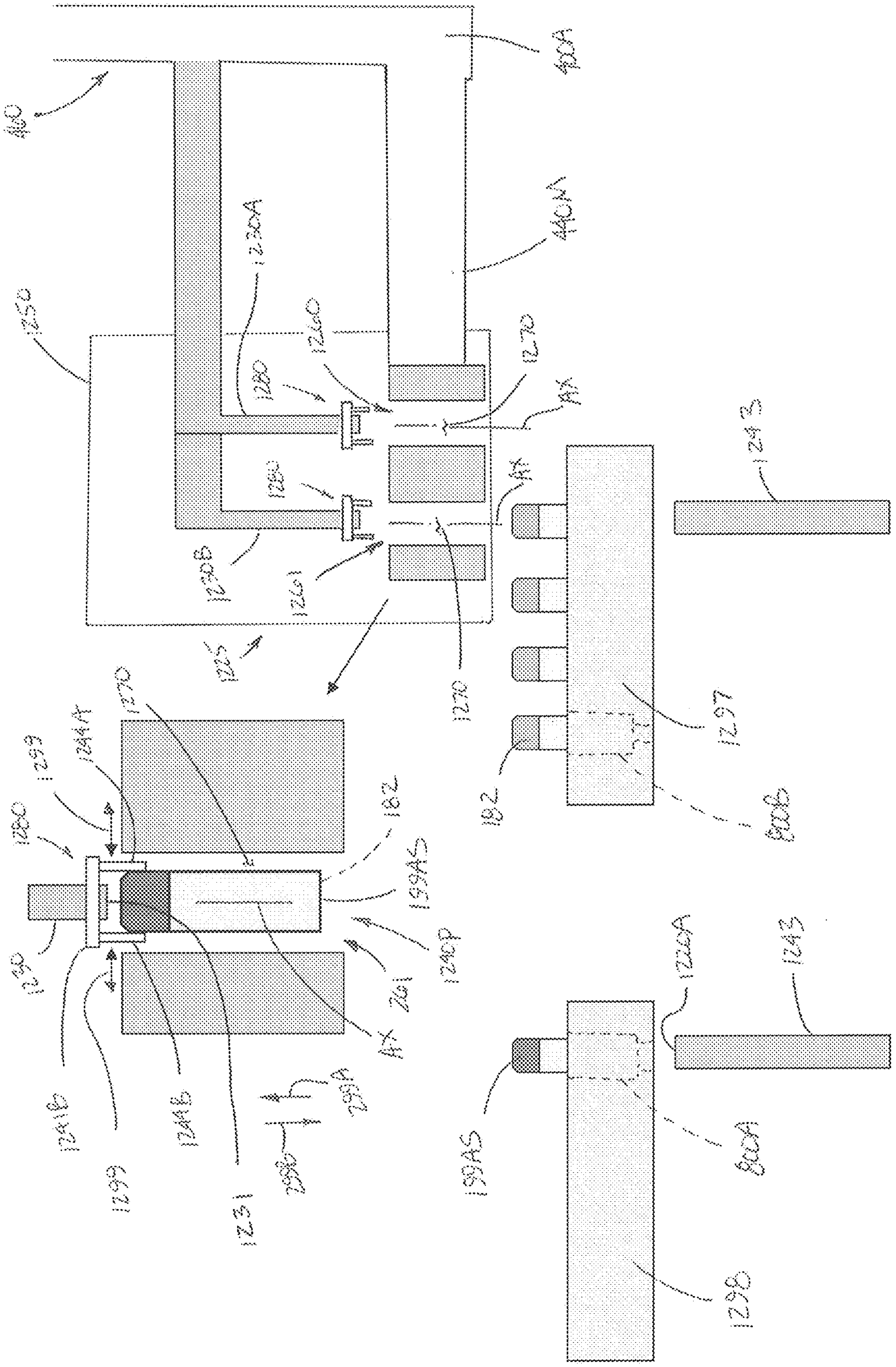
FIG. 12B is an exemplary schematic illustration of the portion of the automated transport of the automated temperature controlled sample specimen laboratory storage system of FIG. 12A in accordance with aspects of the present disclosure.
Figure 12C:
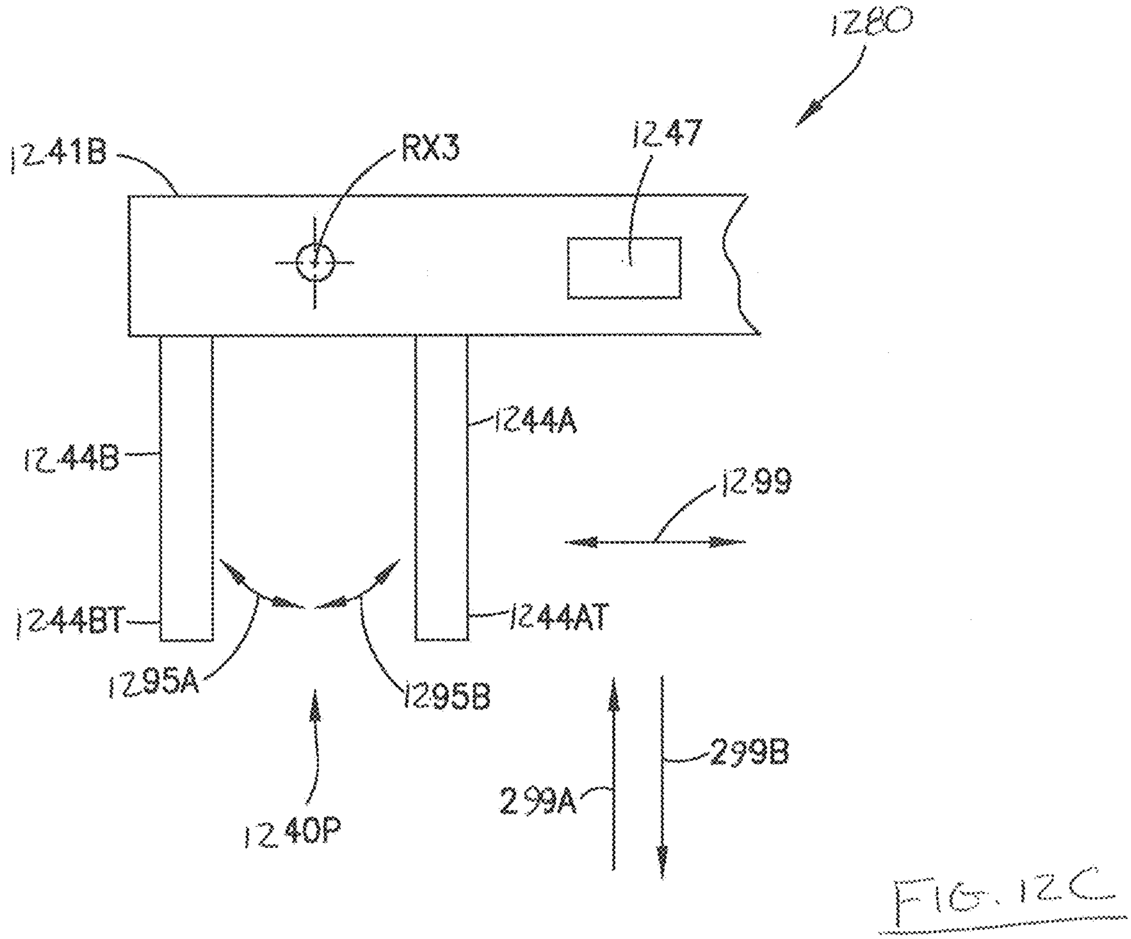
FIG. 12C is an exemplary schematic illustration of the portion of the automated transport of the automated temperature controlled sample specimen laboratory storage system of FIG. 12A in accordance with aspects of the present disclosure.

In the one-step transfer the sample selector module 290 is substantially similar to that described above; however, in this aspect the transfer arm portion 400A includes a multi-sample container holder 440M as illustrated in FIGS. 12A-12C. In FIG. 12A a portion of a transfer device 1201 (which is substantially similar to transfer device 201A, 201B) is shown in an operation of extracting/picking a sample tube 182 (or a simulacrum sample container unit 199AS) from a sample box 180 (or other suitable active sample holder or simulacrum labware device 199 such as those described herein). The multi-sample container holder 440M includes a gripper head 1225 and push-up pin 1243 (also referred to herein as a bottom push member). The gripper head 1125 is positioned above a target sample tube 182 and the push-up pin 1243 is positioned below, the target sample tube 182. The push-up arm 1244, to which the push-up pin is coupled, is driven by a shaft of the drive shaft assembly 460 (FIG. 2B), or in any other suitable manner, to move in the directions 297, 298 (FIG. 2B) in unison with the gripper head 1225. The push-up pin 1243 is driven (such as by the drive shaft assembly 460) in direction 299 so that the push-up pin is raises up through a platform 1221 (holding the sample box 180, and which may be substantially similar to sample tray supports 300R1, 300R2 described above) and the sample box 180, contacting and raising a top portion of the sample tube 182 above the other sample tubes 182 in the sample box 180 so as to provide sufficient clearance around the target sample tube 182 to allow the gripper head 1225 access to the target sample tube 182. The gripper head 1225 grips the top of the sample tube 182 and lifts the sample tube 182 up and out of the sample box 180. In one aspect, the gripper head lifts the sample tube 182 into, and/or the push-up pin 1243 lifts the sample tube 182 into, for example, an insulated hood 1250 that surrounds gripper holding locations 1260, 1261 of the gripper head 1225. As described above, one of the gripper holding locations 1260, 1261 is for holding a labware unit LWU or labware device LWD and the other one of the gripper holding locations 1260, 1261 is a spare holding location for holding a simulacrum labware substitute 199 that corresponds with the a labware unit LWU or labware device LWD to effect a swapping of the a labware unit LWU or labware device LWD with the simulacrum labware substitute 199.

Referring to FIGS. 12B and 12C the gripper head 1225 and a portion of the multi-sample container holder 440M is illustrated in further detail. In the example illustrated, the multi-sample container holder 440M includes two gripper holding locations 1260, 1261 but in other aspects there may be more than two gripper holding locations. Each gripper holding location 1260, 1261 includes an insulated sample holding cavity 1270 configured to substantially maintain a temperature of the sample within the sample tubes 182 (or a temperature of the simulacrum sample container units 199AS) being transferred by the transfer device 1201. The insulated sample holding cavity 1270 of each gripper holding location 1260, 1261 are disposed within the insulated hood 1250.

A respective gripper 1280 is provided for each gripper holding location 1260, 1261. Each gripper 1280 includes a base member 1241B and two movable fingers 1244A, 1244B coupled to the base member 1241B. In one or more aspects the two movable fingers 1244A, 1244B form a sample container passage 1240P between the fingers, however, the sample container passage may not extend through the base member 1241B (e.g. the sample container passage is not a through passage and only allows insertion of the sample tube 182 into the gripper 1280 in one direction 299A). In other aspects the sample container passage may extend through the base member 1241B to allow insertion of sample tubes 182 into the gripper 1280 in directions 299A, 299B. The gripper 1280 includes any suitable actuator(s) (e.g., one or more linear actuator 1247) connected to the movable fingers 1244A, 1244B for gripping (e.g. closing the gripper) and releasing (e.g. opening the gripper) sample tubes 182. In one aspect the movable fingers 1244A, 1244B may be mounted to the base member so as to move linearly relative to the base member 1241B in the direction of arrow 1299 towards and away from each other to respectively grip and release a sample tube 182. In another aspect the movable fingers 1244A, 1244B may be mounted to the base member so as to pivot relative to a predetermined axis of rotation RX2 of the base member 1241B for pivoting tips 1244AT, 1244BT (e.g. free ends) of the movable fingers 1244A, 1244B in the directions of arrows 1295A, 1295B, towards and away from each other to respectively grip and release a sample tube 182. In other aspects, the gripper 1280 may have only one movable finger (either one of fingers 1244A, 1244B) which may operate/move as described above relative to the other finger 1244A, 1244B (which is stationary) for gripping and releasing a sample tube 182.

In one or more aspects, as illustrated in FIG. 12B at least one top (e.g. upper) pusher member 1230A, 1230B is provided on the at least one transfer arm portion 400A to, at least in part, move to sample tube 182 from the gripper 1280 (and gripper head 1225) in direction 299B into a holding location of sample box 180 (or other suitable active sample holder or simulacrum labware device 199 such as those described herein). In one or more other aspects, the at least one top pusher member 1230A, 1230B may not be provided on the at least one transfer arm portion 400A (see FIG. 12A) such that the sample tubes 182 may be provided to the gripper 1280 by, for example, the bottom (e.g. lower) pusher member 1220 in a manner substantially similar to that described herein and where the sample tubes 182 are placed into sample box 180 (or other suitable active sample holder or simulacrum labware device 199 such as those described herein) by gravity (e.g. the sample container falls freely from the gripper 1280 when released for placement into a sample holding location).

Referring again to FIG. 12B, each of the at least one top pusher member 1230A, 1230B may include a sample container engagement portion 1231 extending therefrom towards the gripper 1280. Likewise the bottom pusher member 1243 may also include a sample container engagement portion 1220A extending therefrom towards the gripper 1280. Each of the sample container engagement portions 1231, 1220A may be substantially aligned with an axis AX of the sample container passage 1240P and be configured to pass at least partially through the sample container passage 1240P to effect transfer of sample tubes 182 to or from the gripper 1280 as described herein. In one aspect the sample container engagement portions 1231, 1220A may have a push pin or rod configuration but in other aspects the sample container engagement portions 1231, 1220A may have any suitable shape and size for at least a partial insertion into the sample container passage 1240P and for engagement with the sample tubes 182.

It is noted that while the gripper 1280 is described above with respect to handling of sample tubes 182 (and the simulacrum sample container units 199AS corresponding to the sample tubes 182), the opposing movable fingers 1244A, 1244B of the gripper 1280 also provide for gripping labware having any suitable shape. For example, the opposing movable fingers 1244A, 1244B of the gripper 1280 are also configured to grip labware having substantially hexahedron shapes including, but not limited to, sample cassettes 477, and the simulacrum sample container units 199AS corresponding to the sample cassettes 477.

Referring to FIGS. 12A-12C and 13A-13D an exemplary one-step transfer/substitution of sample tube 182 with a simulacrum sample container unit 199AS will be described. Here, the one-step transfer/substitution is distinguish from a two-step transfer, where in the two-step transfer a first labware unit is picked and place in one step and a second labware unit is picked and placed in a second step distinct from the transfer/pick/place of the first labware unit). The one-step transfer/substitution of the sample tube 182 with the simulacrum sample container units 199AS effected with the gripper head 1225 includes picking of a first labware unit from a first holding location, picking a second labware unit from a second holding location so that both the first and second labware units are simultaneously held by the gripper head 1225, and then a substantially immediate (e.g., after picking of the second labware unit) placement of the first labware unit in the second holding location followed by placement of the second labware unit in the first (or other) holding location so that the second labware unit is "fast" swapped with the first labware unit at the second holding location.

In the example provided the gripper head includes two top pusher members 1230A, 1230B (i.e., a top pusher member 1230A, 1230B for each gripper holding location 1260, 1261); however, in other aspects the transfer of the sample tube 182 and the simulacrum sample container unit 199AS from the gripper head 1225 to a holding location 800 (see FIG. 8) of the labware devices 1297, 1298 (which may be any combination of the active labware devices LWD described herein and the simulacrum labware devices 199B described herein) is effected by gravity as described herein.

Figure 13A:
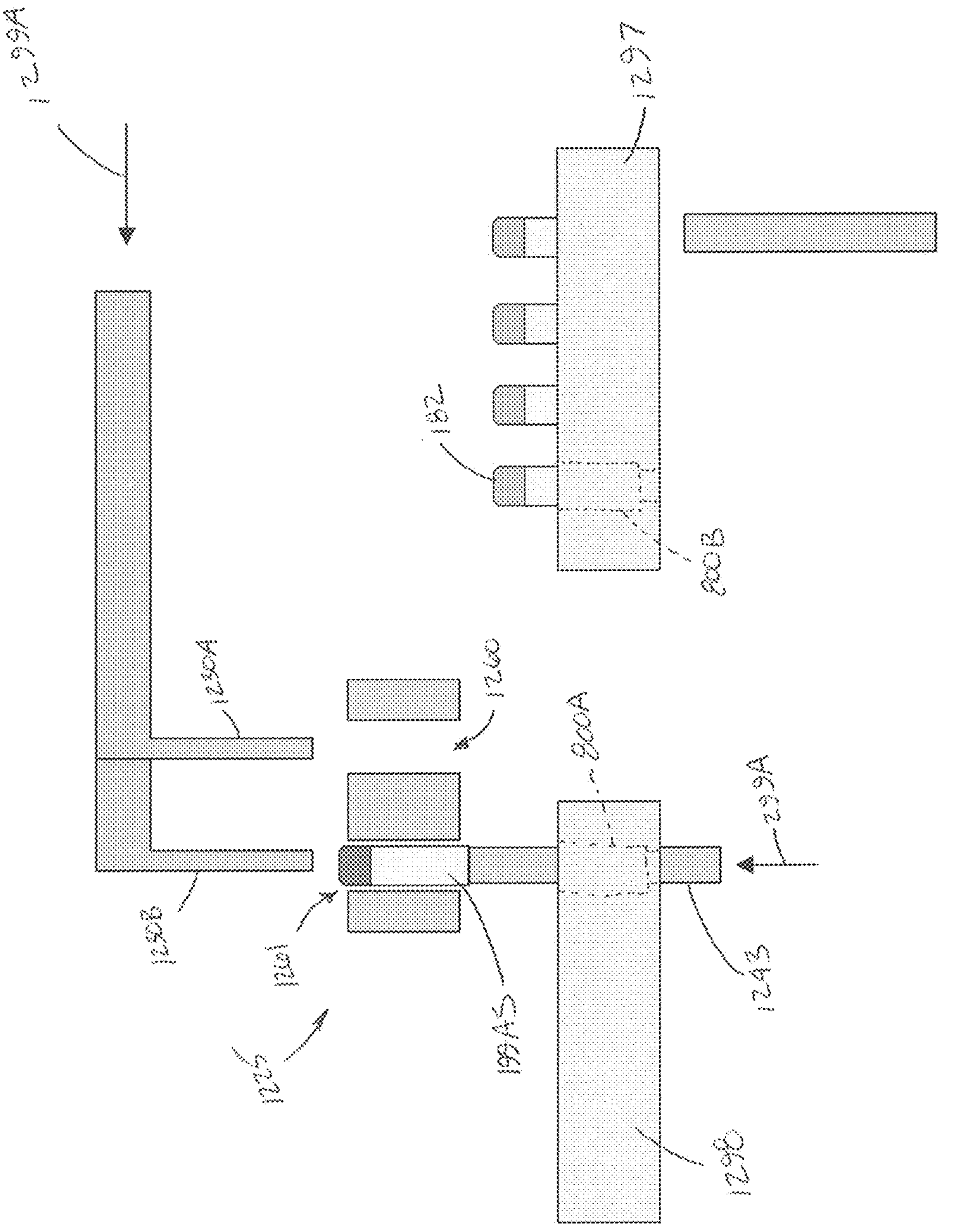
FIGS. 13A-13D are a sequence of schematic illustrations of an active labware and simulacrum labware substitute swap with the automated transport of FIG. 12A in accordance with aspects of the present disclosure.
Figure 13B:
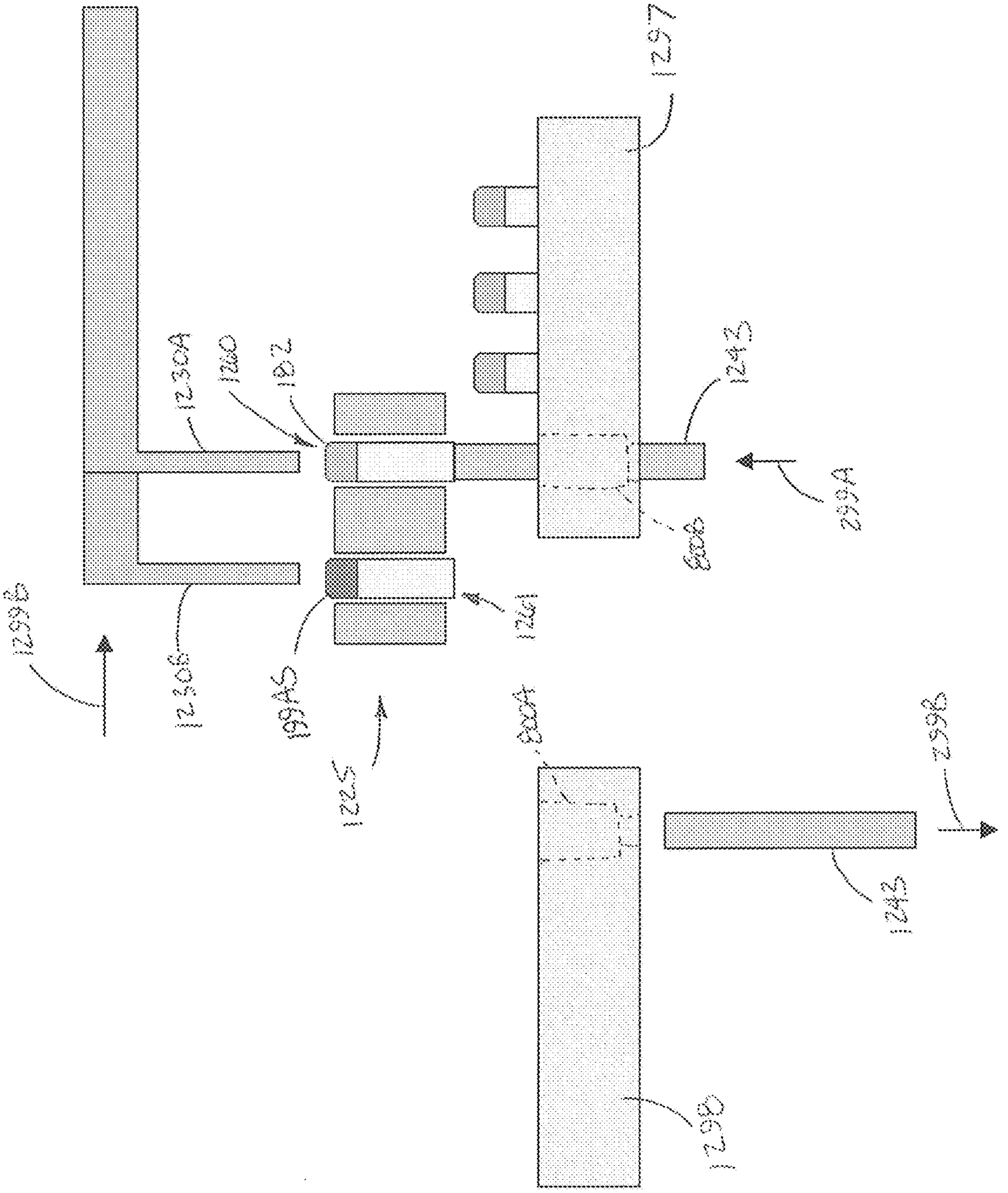
Figure 13C:
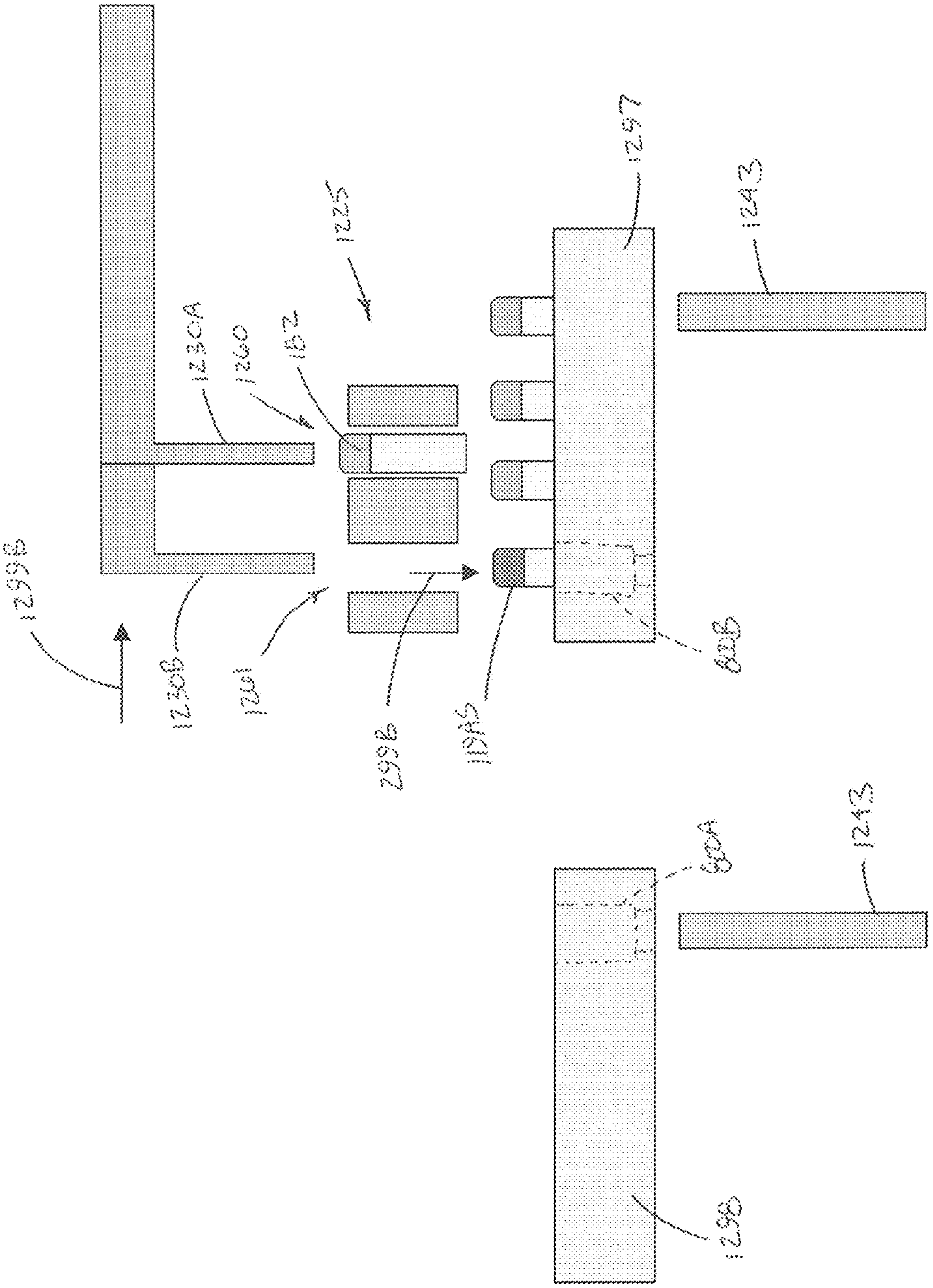
Figure 13D:
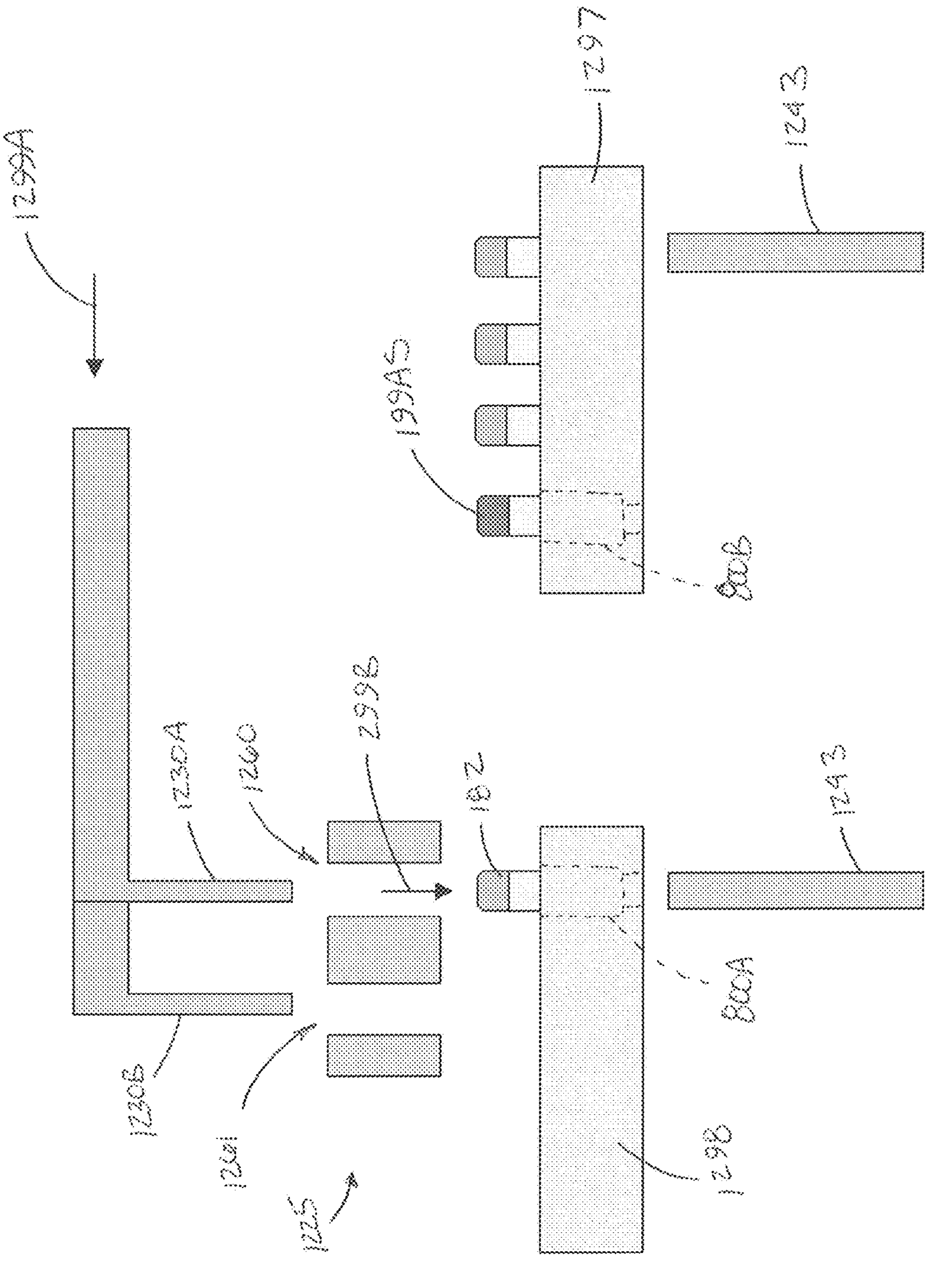
Figure 17:
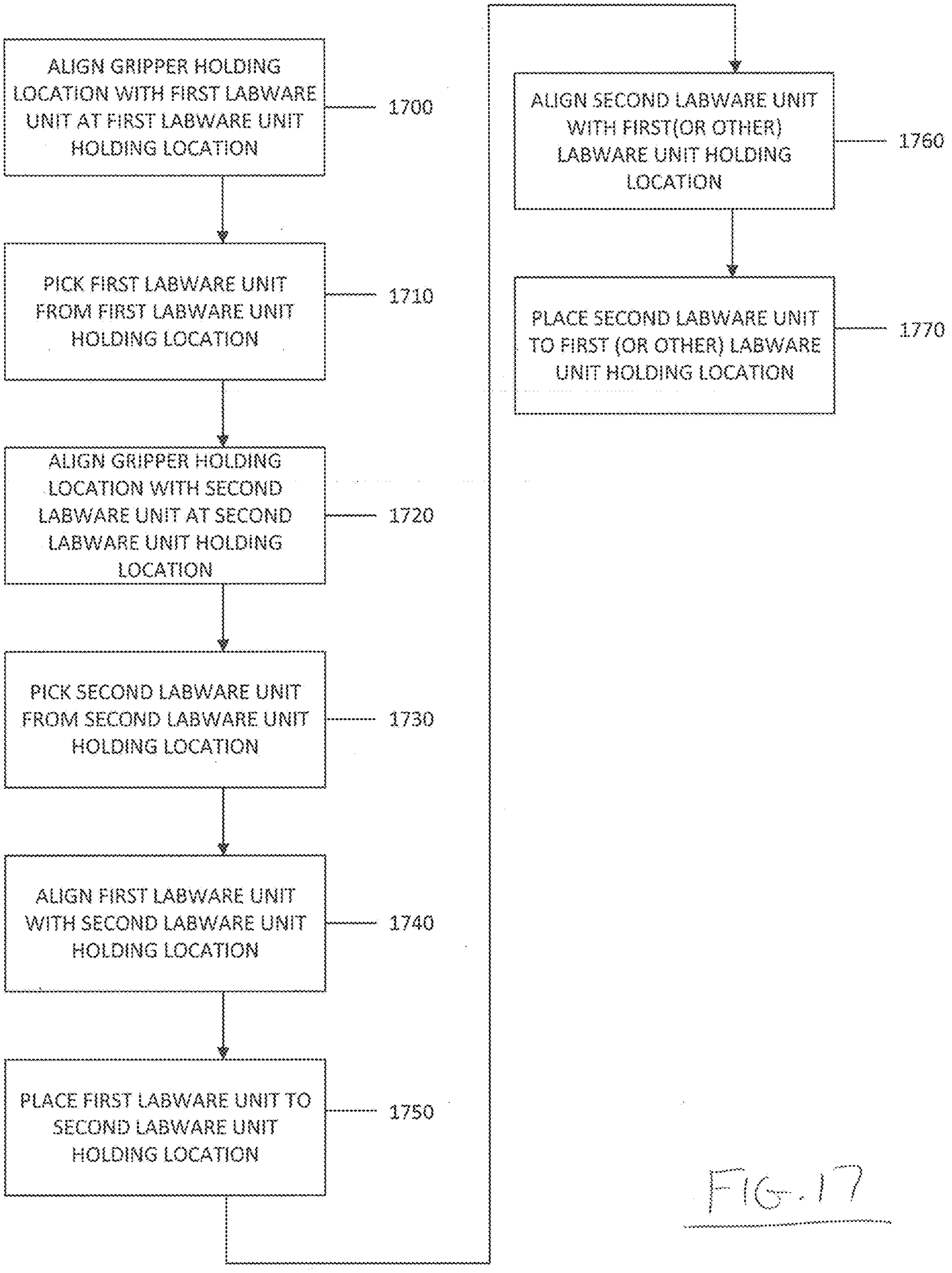

To substitute the sample holder 182 held in labware device 1297 with the simulacrum sample container unit 199AS held in labware device 1298, the gripper head 1225 moves in direction 1299A so as to align one of the gripper holding locations 1260, 1261 with the simulacrum sample container unit 199AS (e.g., the first labware unit) at the first (labware unit) holding location 800A of labware device 1298 (FIG. 17, Block 1700) (see FIG. 13A). The simulacrum sample container unit 199AS is picked from the first holding location 800A by the gripper head 1225 (the grippers 1280 are omitted in FIGS. 13A-13D for clarity) (FIG. 17, Block 1710). To pick the simulacrum sample container unit 199AS from the first holding location 800A, the push-up pin 1243 extends through the first holding location 800A of labware device 1298 to move the simulacrum sample container unit 199AS in direction 299A into the gripper head 1225 so that the simulacrum sample container unit 199AS is gripped by gripper 1280 (FIG. 12B) of gripper holding location 1261.

With the simulacrum sample container unit 199AS held by the gripper head 1225, the gripper head 1225 moves in direction 1299B so as to align the other of the gripper holding locations 1260, 1261 (i.e., the spare holding location that is not holding the simulacrum sample container unit 199AS) with the sample holder 182 (e.g., the second labware unit) at the second (labware unit) holding location 800B of labware device 1297 (FIG. 17, Block 1720) (see FIG. 13A). Here, the gripper holding location 1260 is aligned with the sample holder 182. The sample holder 182 is picked from the second holding location 800B by the gripper head 1225 (FIG. 17, Block 1730). To pick the sample holder 182 from the second holding location 800B, the push-up pin 1243 (which may be same or different than the push-up pin 1243 employed for labware device 1298) extends through the second holding location 800B of labware device 1297 to move the sample holder 182 in direction 299A into the gripper head 1225 so that the sample holder 182 is gripped by gripper 1280 (FIG. 12B) of gripper holding location 1260.

With both the sample tube 182 and the simulacrum sample container unit 199AS held by the gripper head 1225, the gripper head moves in direction 1299B to align the simulacrum sample container unit 199AS with the second holding location 800B (FIG. 17, Block 1740). The simulacrum sample container unit 199AS is placed to the second holding location 800B (FIG. 17, Block 1750) by releasing the simulacrum sample container unit 199AS from the gripper 1280 and lowering the simulacrum sample container unit 199AS from the gripper holding location 1261 at least in part with the top pusher member 1230B; while in other aspects the released simulacrum sample container unit 199AS is lowered under the force of gravity as described herein. The placement of the simulacrum sample container unit 199AS to the second holding location 800B occurs in rapid succession (e.g., substantially immediately) after picking of the sample holder 182 from the second holding location 800B.

To place the sample holder 182, the gripper head 1225 moves in direction 1299A so as to align the other of the gripper holding locations 1260, 1261 (i.e., the spare holding location that is now holding the sample holder 182) with the first holding location 800A of labware device 1298 (FIG. 17, Block 1760) (see FIG. 13A). Here, the gripper holding location 1260 is aligned with the sample holder 182. The sample holder 182 is placed to the first holding location 800A (FIG. 17, Block 1770) by releasing the sample holder 182 from the gripper 1280 and lowering the sample holder 182 from the gripper holding location 1260 at least in part with the top pusher member 1230A; while in other aspects the released sample holder 182 is lowered under the force of gravity as described herein. It is noted that the top grippers 1230A, 1230B are independently operable for movement in direction 299.

As can be seen from the above, the aspects of the present disclosure provide for simulacrum labware units 199A and simulacrum labware devices 199B, at least portions of which have a high thermal mass. These simulacrum labware substitutes 199 fill a store 100A, 100B so as to maximize thermal inertia throughout storage arrays SA of the stores 100A, 100B to extend the time it takes to increase temperature in the stores 100A, 100B due to, for example, a loss of power and/or a loss of refrigeration. The simulacrum labware substitutes 199 are swapped for corresponding active labware units LWU and/or active labware devices LWD using automated transports of the stores 100A, 100B so that the active labware units LWU and/or active labware devices LWD are placed within the store 100A, 100B so that other simulacrum labware substitutes within the store 100A, 100B decrease the time it takes to freeze the samples within the active labware units LWU and/or active labware devices LWD.

Figure 20:
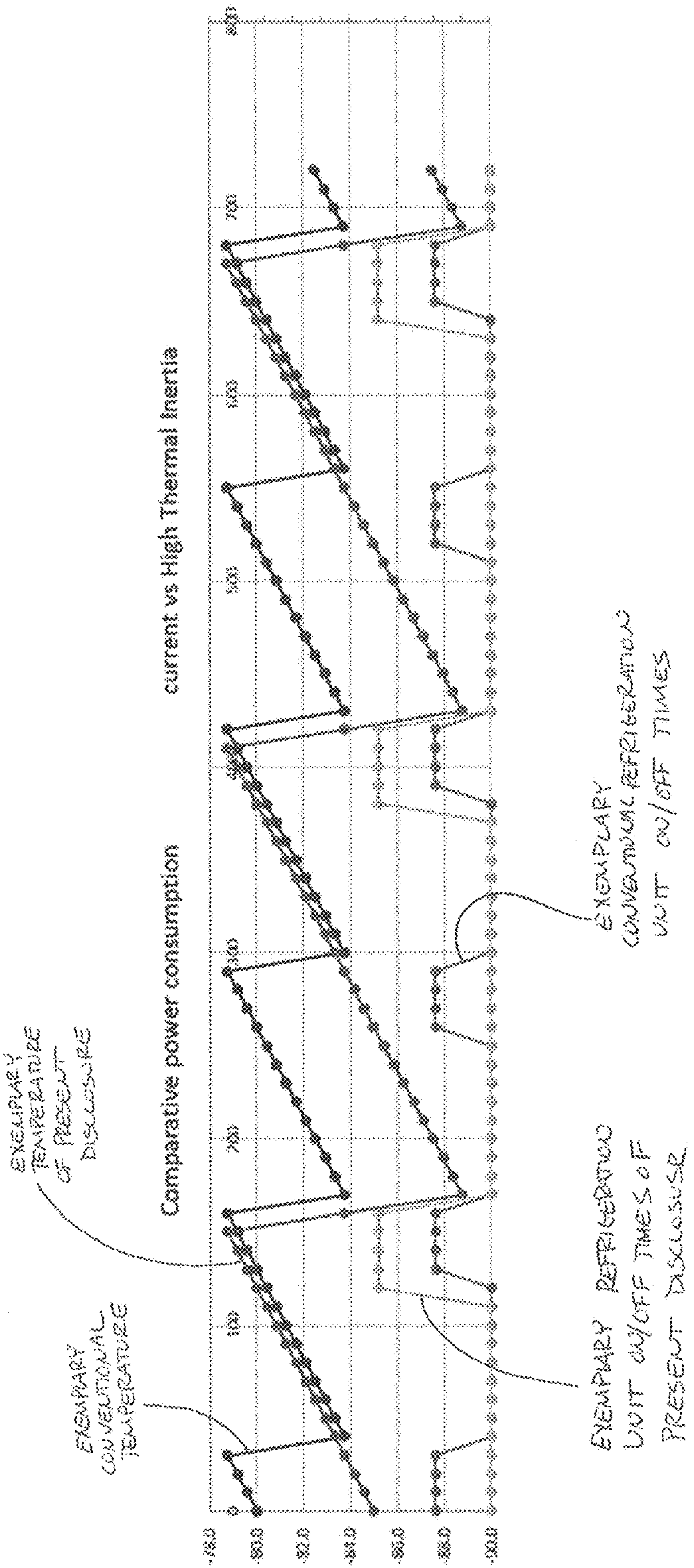
FIG. 20 is an exemplary graph of model data illustrating a comparative reduction in power consumption of the automated temperature controlled sample specimen laboratory storage systems described herein, in accordance with aspects of the present disclosure.
Figure 21:
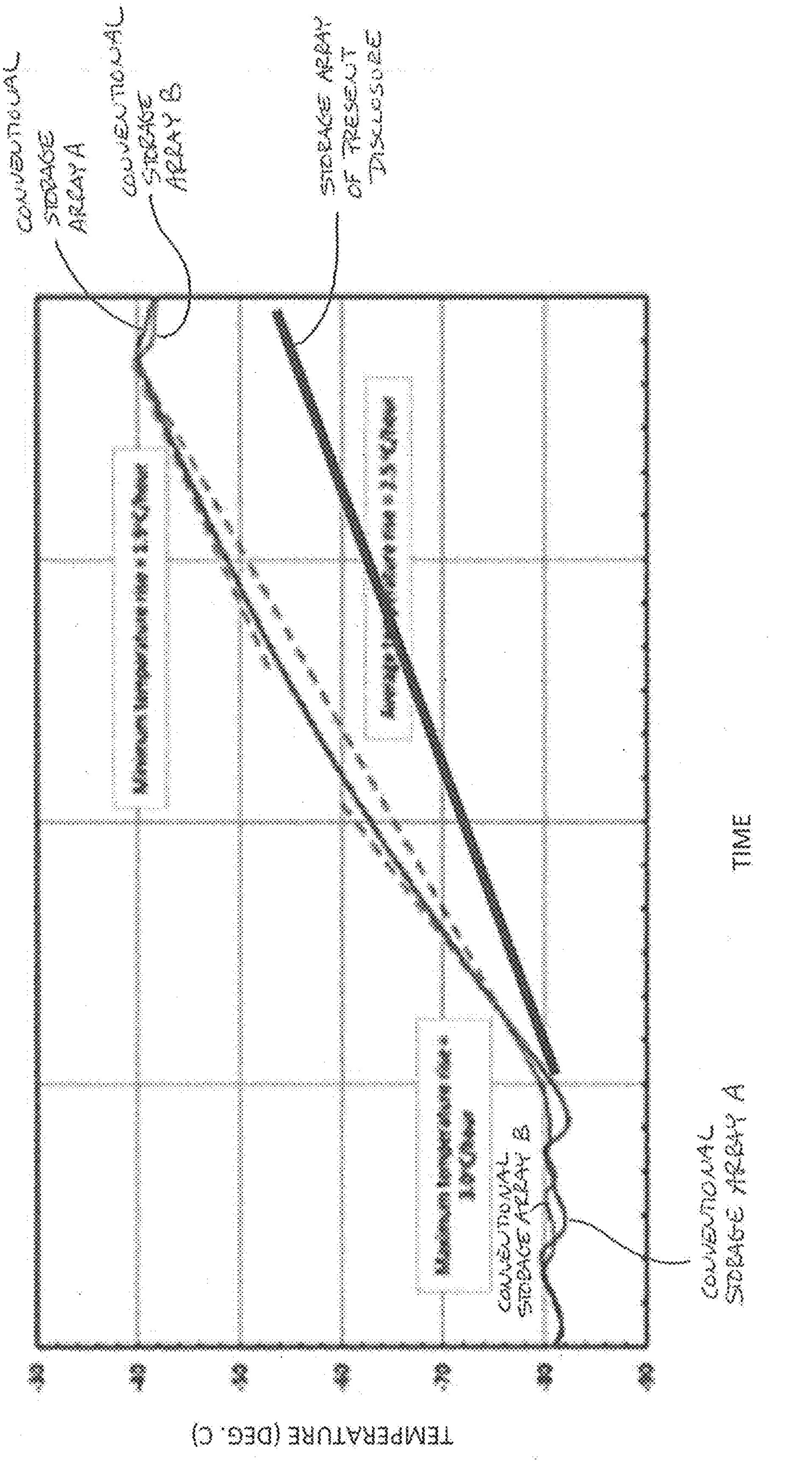
FIG. 21 is an exemplary graph of model data illustrating a comparison between a temperature rise in conventional storage arrays of an automated temperature controlled sample specimen laboratory storage system and a temperature rise in the automated temperature controlled sample specimen laboratory storage systems described herein in accordance with aspects of the present disclosure.

Referring to FIGS. 20 and 21, the aspects of the present disclosure described herein provide for the maximizing of the thermal inertia of the storage areas of a store 100A, 100B substantially at all times. This maximization of thermal inertia effects one or more of a reduction of warm-up rates in case of power loss (see FIG. 21 comparing the warm up rates of conventional stores with that of the stores described herein), longer periods of times with refrigeration units of the storage areas turned off or producing a minimum refrigeration output (leading to energy savings—see FIG. 20), an increased temperature stability in the storage areas of the store 100A, 100B, and increased temperature uniformity as the simulacrum labware substitutes 199 settle near the predetermined temperature set point of the storage areas. In accordance with the aspects of the present disclosure the controller 170 is configured to (e.g., includes any suitable non-transitory program code that) leverage(s) the thermal density and high thermal inertia (i.e., high thermal capacity) provided by the simulacrum labware substitutes 199 within the store 100A, 100B to lower cycling of the refrigeration units for the storage areas (i.e., the on/off cycling of the refrigeration units to maintain the predetermined temperature set point is reduced, i.e., fewer on/off cycles). The leveraging of the thermal density and high thermal inertia maximizes power off or production of minimum refrigeration output periods of the refrigeration units (i.e., as a result of the decreased cycling of the refrigeration units) and minimizes (or otherwise avoids) rapid cycling of the refrigeration units, compared to (see FIG. 20) conventional refrigeration of empty (or partially filled) stores (e.g., the conventional refrigeration requiring increased power on periods as a result of increased/higher cycling rates of the refrigeration units of conventional storage). The leveraging of the thermal density and high thermal inertia provides for longer cycles times (e.g., with the refrigeration units off) due to, for example, longer steady state running temperatures provided by the simulacrum labware substitutes 199 compared to (see FIG. 20) conventional refrigeration of empty (or partially filled) conventional stores (which require frequent and short refrigeration cycles due to losses in the refrigeration system/store due to frequent transients from steady state operation and an increased time to bring (and maintain) the refrigeration system/store to a steady state operating temperature throughout operation of the conventional store).

In accordance with one or more aspects of the present disclosure a temperature controlled sample specimen laboratory storage system for storing sample specimens disposed in one or more of labware units and labware devices is provided. The temperature controlled sample specimen laboratory storage system comprising:

a refrigerated chamber with a storage array therein having predetermined storage locations, each configured for holding therein at least one of the one or more of the labware units and labware devices per storage location, the predetermined storage locations defining a predetermined capacity of one or more of labware unit storage and labware device storage of the storage array, where the storage array has a predetermined area; and at least one simulacrum labware substitute having a predetermined characteristic that simulates a corresponding one of the one or more of the labware units and labware devices so that the at least one simulacrum labware substitute and the corresponding one of the one or more of the labware units and labware devices are interchangeable with respect to each storage location holding the at least one simulacrum labware substitute swapped for the corresponding one of the one or more of the labware units and labware devices; and wherein the at least one simulacrum labware substitute held in the storage location is disposed within the storage array so that the predetermined capacity of the one or more of the labware unit storage and the labware device storage of the storage array, of predetermined area, is unconstrained by the at least one simulacrum labware substitute held in the storage location.

In accordance with one or more aspects of the present disclosure the predetermined capacity of the one or more of the labware unit storage and the labware device storage of the storage array remains a maximum capacity independent of the at least one simulacrum labware substitute held in the storage location.

In accordance with one or more aspects of the present disclosure the predetermined characteristic of the at least one simulacrum labware substitute has a first thermal mass characteristic that is an analogue for a second thermal mass characteristic of the respective one of the one or more of the interchangeable labware units and labware devices.

In accordance with one or more aspects of the present disclosure the first thermal mass characteristic and the second thermal mass characteristic are the same in character and in magnitude.

In accordance with one or more aspects of the present disclosure the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

In accordance with one or more aspects of the present disclosure the addition and removal of the at least one simulacrum labware substitute is balanced with the addition and removal of the corresponding one of the one or more of the labware units and labware devices so as to maximize fill of the storage array throughout the storage array.

In accordance with one or more aspects of the present disclosure the automated transport has a gripper configured to automatically engage and swap, at each storage location, the one or more of the labware units and labware devices with the at least one simulacrum labware substitute, and vice versa, so that fill of the storage array is substantially constant, throughout the storage array, with addition and removal of the one or more of the labware units and labware devices from each storage location.

In accordance with one or more aspects of the present disclosure the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

In accordance with one or more aspects of the present disclosure the at least one simulacrum labware substitute is configured and disposed within the storage array so that the at least one simulacrum labware substitute held in each storage location effects predetermined thermal inertia bias sustaining thermal equilibrium across each other storage location of the storage array separate from refrigeration of the refrigerated chamber.

In accordance with one or more aspects of the present disclosure the at least one simulacrum labware substitute effects thermal equilibrium from within the storage location holding the at least one simulacrum labware substitute in swap for holding the one or more of the labware units and labware devices in the storage location.

In accordance with one or more aspects of the present disclosure the temperature controlled sample specimen laboratory storage system further comprises a buffer, in the refrigerated chamber, for the at least one simulacrum labware substitute, the buffer being separate and distinct from the storage array and each storage location of the storage array.

In accordance with one or more aspects of the present disclosure the storage array of the refrigerated chamber is at least one from (1) a sample container holding plate, (2) a sample container holding tray, (3) a plate holder, (4) a tray holder, (5) a sample holding rack, (6) a sample holding box, and (7) a portable or fixed store rack disposed for holding one or more of a sample container holding plate, a sample container holding tray, a plate holder, a tray holder, a sample holding rack, and a sample holding box in stored array.

In accordance with one or more aspects of the present disclosure the labware devices are portable to and from the storage array and insertable into and removable from each storage location of the storage array, and is at least one from (1) a sample container holding plate, (2) a sample container holding tray, (3) a plate holder, (4) a tray holder, (5) a sample holding rack, (6) a sample holding box, and (7) a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

In accordance with one or more aspects of the present disclosure the labware units are at least one from a vial, tube, cassette, and a microwell plate.

In accordance with one or more aspects of the present disclosure the labware units are portable specimen sample containers of unitary construction.

In accordance with one or more aspects of the present disclosure the labware devices are each a portable labware unit holder for at least one labware unit.

In accordance with one or more aspects of the present disclosure more than one simulacrum labware substitute are shaped so that the at least one simulacrum labware substitute, held in a storage location and another simulacrum labware substitute held in another storage location communicate with each other over a thermal transfer link so as to cooperate in sustainment of thermal equilibrium across each other storage location of the storage array separate from refrigeration of the refrigerated chamber.

In accordance with one or more aspects of the present disclosure the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

In accordance with one or more aspects of the present disclosure different simulacrum labware substitutes, at least one of which has different thermal mass than another, are disposed in storage locations of the storage array to provide a predetermined thermal inertia profile or gradient in at least one axis over the storage array.

In accordance with one or more aspects of the present disclosure different simulacrum labware substitutes, at least one of which has different thermal mass than another, are disposed in storage locations of the storage array to provide a predetermined thermal inertia profile or gradient in at least one axis relative to a predetermined storage location holding the at least one simulacrum labware substitute.

In accordance with one or more aspects of the present disclosure the at least one simulacrum labware substitute is preloaded in the storage location.

In accordance with one or more aspects of the present disclosure a temperature controlled sample specimen laboratory storage system for storing sample specimens disposed in one or more of labware units and labware devices is provided. The temperature controlled sample specimen laboratory storage system comprising:

a refrigerated chamber with a storage array therein having predetermined storage locations, each configured for holding therein at least one of the one or more of the labware units and labware devices per storage location, the predetermined storage locations defining a predetermined capacity of one or more of labware unit storage and labware device storage of the storage array, where the storage array has a predetermined area; and at least one simulacrum labware substitute having a predetermined characteristic that simulates a corresponding one of the one or more of the labware units and labware devices so that the at least one simulacrum labware substitute and the corresponding one of the one or more of the labware units and labware devices are interchangeable at each storage location for holding the one or more of the labware units and labware devices so that the one or more of the labware units and labware devices and the at least one simulacrum labware substitute are swapped for each other at the storage location; and wherein disposition of the at least one simulacrum labware substitute held in the storage location is unconstrained throughout the storage array so that the predetermined capacity of the one or more of the labware unit storage and the labware device storage of the storage array, of a predetermined area, is maintained at a maximum.

In accordance with one or more aspects of the present disclosure the predetermined capacity of the one or more of the labware unit storage and the labware device storage of the storage array remains a maximum capacity independent of the at least one simulacrum labware substitute held in the storage location.

In accordance with one or more aspects of the present disclosure the predetermined characteristic of the at least one simulacrum labware substitute has a first thermal mass characteristic that is an analogue for a second thermal mass characteristic of the respective one of the one or more of the interchangeable labware units and labware devices.

In accordance with one or more aspects of the present disclosure the first thermal mass characteristic and the second thermal mass characteristic are the same in character and in magnitude.

In accordance with one or more aspects of the present disclosure the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

In accordance with one or more aspects of the present disclosure the addition and removal of the at least one simulacrum labware substitute is balanced with the addition and removal of the corresponding one of the one or more of the labware units and labware devices so as to maximize fill of the storage array throughout the storage array.

In accordance with one or more aspects of the present disclosure the automated transport has a gripper configured to automatically engage and swap, at each storage location, the one or more of the labware units and labware devices with the at least one simulacrum labware substitute, and vice versa, so that fill of the storage array is substantially constant, throughout the storage array, with addition and removal of the one or more of the labware units and labware devices from each storage location.

In accordance with one or more aspects of the present disclosure the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

In accordance with one or more aspects of the present disclosure the at least one simulacrum labware substitute is configured and disposed within the storage array so that the at least one simulacrum labware substitute held in each storage location effects predetermined thermal inertia bias sustaining thermal equilibrium across each other storage location of the storage array separate from refrigeration of the refrigerated chamber.

In accordance with one or more aspects of the present disclosure the simulacrum labware substitute effects thermal equilibrium from within the storage location holding the at least one simulacrum labware substitute in swap for holding the one or more of the labware units and labware devices in the storage location.

In accordance with one or more aspects of the present disclosure a temperature controlled sample specimen laboratory storage system further comprises a buffer, in the refrigerated chamber, for the at least one simulacrum labware substitute, the buffer being separate and distinct from the storage array and each storage location of the storage array.

In accordance with one or more aspects of the present disclosure the storage array of the refrigerated chamber is at least one from (1) a sample container holding plate, (2) a sample container holding tray, (3) a plate holder, (4) a tray holder, (5) a sample holding rack, (6) a sample holding box, and (7) a portable or fixed store rack disposed for holding one or more of a sample container holding plate, a sample container holding tray, a plate holder, a tray holder, a sample holding rack, and a sample holding box in stored array.

In accordance with one or more aspects of the present disclosure the labware devices are portable to and from the storage array and insertable into and removable from each storage location of the storage array, and is at least one from (1) a sample container holding plate, (2) a sample container holding tray, (3) a plate holder, (4) a tray holder, (5) a sample holding rack, (6) a sample holding box, and (7) a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

In accordance with one or more aspects of the present disclosure the labware units are at least one from a vial, tube, cassette, and a microwell plate.

In accordance with one or more aspects of the present disclosure the labware units are portable specimen sample containers of unitary construction.

In accordance with one or more aspects of the present disclosure the labware devices are each a portable labware unit holder for at least one labware unit.

In accordance with one or more aspects of the present disclosure more than one simulacrum labware substitute are shaped so that the at least one simulacrum labware substitute, held in a storage location and another simulacrum labware substitute held in another storage location communicate with each other over a thermal transfer link so as to cooperate in sustainment of thermal equilibrium across each other storage location of the storage array separate from refrigeration of the refrigerated chamber.

In accordance with one or more aspects of the present disclosure the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

In accordance with one or more aspects of the present disclosure different simulacrum labware substitutes having at least one of which has different thermal mass than another, are disposed in storage locations of the storage array to provide a predetermined thermal inertia profile, or gradient in at least one axis over the storage array.

In accordance with one or more aspects of the present disclosure different simulacrum labware substitutes having at least one of which has different thermal mass than another, are disposed in storage locations of the storage array to provide a predetermined thermal inertia profile, or gradient in at least one axis relative to a predetermined storage location holding the at least one simulacrum labware substitute.

In accordance with one or more aspects of the present disclosure the at least one simulacrum labware substitute is preloaded in the storage location.

In accordance with one or more aspects of the present disclosure a temperature controlled sample specimen laboratory storage system for storing sample specimens disposed in one or more of labware units and labware devices is provided. The temperature controlled sample specimen laboratory storage system comprising:

a refrigerated chamber with a storage array therein having predetermined storage locations, each of the storage locations are configured for holding therein at least one of the one or more of the labware units and labware devices per storage location at a refrigerated thermal equilibrium; and at least one simulacrum labware substitute, each of the at least one simulacrum labware substitute having a predetermined thermal mass analogous with that of each of the at least one of the one or more labware units and labware devices, and the at least one simulacrum labware substitute and the at least one of the one or more of the labware units and the labware devices are interchangeable at each storage location for holding the one or more of the labware units and the labware devices so that the at least one of the one or more labware units and labware devices and the at least one simulacrum labware substitute are swapped for each other at the storage location; and wherein the at least one simulacrum labware substitute held in the storage location is disposed within the storage array so that the at least one simulacrum labware substitute held in each storage location throughout the storage array effects predetermined thermal inertia bias so as to maintain refrigerated thermal equilibrium, via thermal inertia bias, throughout the storage array separate and distinct from refrigeration of the refrigerated chamber.

In accordance with one or more aspects of the present disclosure the at least one simulacrum labware substitute held in each storage location throughout the storage array effects thermal bias response, about a thermal equilibrium of the refrigerated chamber, so as to maintain the refrigerated thermal equilibrium throughout the storage array.

In accordance with one or more aspects of the present disclosure the predetermined storage locations define a predetermined capacity of one or more of labware units storage and labware devices storage of the storage array, for the storage array of a predetermined area, and the predetermined capacity of the one or more of the labware units storage and the labware devices storage of the storage array, of predetermined area, is unconstrained by the at least one simulacrum labware substitute held in swap for at least one of the one or more labware units and labware devices in the storage location.

In accordance with one or more aspects of the present disclosure the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

In accordance with one or more aspects of the present disclosure the addition and removal of the at least one simulacrum labware substitute is balanced with the addition and removal of the corresponding one of the one or more of the labware units and labware devices so as to maximize fill of the storage array throughout the storage array.

In accordance with one or more aspects of the present disclosure the automated transport has a gripper configured to automatically engage and swap, at each storage location, the one or more of the labware units and labware devices with the at least one simulacrum labware substitute, and vice versa, so that fill of the storage array is substantially constant, throughout the storage array, with addition and removal of the one or more of the labware units and labware devices from each storage location.

In accordance with one or more aspects of the present disclosure the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

In accordance with one or more aspects of the present disclosure the at least one simulacrum labware substitute effects the refrigerated thermal equilibrium from within a storage location of the predetermined storage locations holding the at least one simulacrum labware substitute in swap for holding the one or more of the labware units and labware devices in the storage location.

In accordance with one or more aspects of the present disclosure the temperature controlled sample specimen laboratory storage system further comprises a buffer, in the refrigerated chamber, for the at least one simulacrum labware substitute, the buffer being separate and distinct from the storage array and each storage location of the storage array.

In accordance with one or more aspects of the present disclosure the storage array of the refrigerated chamber is at least one from (1) a sample container holding plate, (2) a sample container holding tray, (3) a plate holder, (4) a tray holder, (5) a sample holding rack, (6) a sample holding box, and (7) a portable or fixed store rack disposed for holding one or more of a sample container holding plate, a sample container holding tray, a plate holder, a tray holder, a sample holding rack, and a sample holding box in stored array.

In accordance with one or more aspects of the present disclosure the labware devices are portable to and from the storage array and insertable into and removable from each storage location of the storage array, and is at least one from (1) a sample container holding plate, (2) a sample container holding tray, (3) a plate holder, (4) a tray holder, (5) a sample holding rack, (6) a sample holding box, and (7) a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

In accordance with one or more aspects of the present disclosure the labware units are at least one from a vial, tube, cassette, and a microwell plate.

In accordance with one or more aspects of the present disclosure the labware units are portable specimen sample containers of unitary construction.

In accordance with one or more aspects of the present disclosure the labware devices are each a portable labware unit holder for at least one labware unit.

In accordance with one or more aspects of the present disclosure more than one simulacrum labware substitute are shaped so that the at least one simulacrum labware substitute, held in a storage location and another simulacrum labware substitute held in another storage location communicate with each other over a thermal transfer link so as to cooperate in sustainment of the refrigerated thermal equilibrium across each other storage location of the storage array separate from refrigeration of the refrigerated chamber.

In accordance with one or more aspects of the present disclosure the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

In accordance with one or more aspects of the present disclosure different simulacrum labware substitutes having at least one of which has different thermal mass than another, are disposed in storage locations of the storage array to provide a predetermined thermal inertia profile, or gradient in at least one axis over the storage array.

In accordance with one or more aspects of the present disclosure different simulacrum labware substitutes having at least one of which has different thermal mass than another, are disposed in storage locations of the storage array to provide a predetermined thermal inertia profile, or gradient in at least one axis relative to a predetermined storage location holding the at least one simulacrum labware substitute.

In accordance with one or more aspects of the present disclosure the at least one simulacrum labware substitute is preloaded in the storage location.

In accordance with one or more aspects of the present disclosure a method for controlling a temperature within a temperature controlled sample specimen laboratory storage system is provided. The temperature controlled sample specimen laboratory storage system being configured to store sample specimens disposed in one or more of labware units and labware devices and including a refrigerated chamber with a storage array therein having predetermined storage locations, each configured for holding therein at least one of the one or more of the labware units and labware devices per storage location, the predetermined storage locations defining a predetermined capacity of one or more of labware unit storage and labware device storage of the storage array, where the storage array has a predetermined area. The method comprising:

- providing at least one simulacrum labware substitute having a predetermined characteristic that simulates a corresponding one of the one or more of the labware units and labware devices so that the at least one simulacrum labware substitute and the corresponding one of the one or more of the labware units and labware devices are interchangeable with respect to each storage location holding the at least one simulacrum labware substitute swapped for the corresponding one of the one or more of the labware units and labware devices; and
- disposing the at least one simulacrum labware substitute in at least one of the predetermined storage locations within the storage array so that the predetermined capacity of the one or more of the labware unit storage and the labware device storage of the storage array, of predetermined area, is unconstrained by the at least one simulacrum labware substitute held in the at least one predetermined storage location.

In accordance with one or more aspects of the present disclosure the predetermined capacity of the one or more of the labware unit storage and the labware device storage of the storage array remains a maximum capacity independent of the at least one simulacrum labware substitute held in the storage location.

In accordance with one or more aspects of the present disclosure the predetermined characteristic of the at least one simulacrum labware substitute has a first thermal mass characteristic that is an analogue for a second thermal mass characteristic of the respective one of the one or more of the interchangeable labware units and labware devices.

In accordance with one or more aspects of the present disclosure the first thermal mass characteristic and the second thermal mass characteristic are the same in character and in magnitude.

In accordance with one or more aspects of the present disclosure the method further comprises balancing addition and removal of the at least one simulacrum labware substitute from the storage array, with addition and removal of a corresponding one of the one or more of the labware units and labware devices from the storage array, wherein balancing is effected with an automated transport of the temperature controlled sample specimen laboratory storage system.

In accordance with one or more aspects of the present disclosure the addition and removal of the at least one simulacrum labware substitute is balanced with the addition and removal of the corresponding one of the one or more of the labware units and labware devices so as to maximize fill of the storage array throughout the storage array.

In accordance with one or more aspects of the present disclosure the method further comprises automatically engaging and swapping, at each storage location and with a gripper of the automated transport, the one or more of the labware units and labware devices with the at least one simulacrum labware substitute, and vice versa, so that fill of the storage array is substantially constant, throughout the storage array, with addition and removal of the one or more of the labware units and labware devices from each storage location.

In accordance with one or more aspects of the present disclosure the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

In accordance with one or more aspects of the present disclosure the at least one simulacrum labware substitute is configured and disposed within the storage array so that the at least one simulacrum labware substitute held in each storage location effects predetermined thermal inertia bias sustaining thermal equilibrium across each other storage location of the storage array separate from refrigeration of the refrigerated chamber.

In accordance with one or more aspects of the present disclosure the at least one simulacrum labware substitute effects thermal equilibrium from within the storage location holding the at least one simulacrum labware substitute in swap for holding the one or more of the labware units and labware devices in the storage location.

In accordance with one or more aspects of the present disclosure the method further comprises providing a buffer, in the refrigerated chamber, for the at least one simulacrum labware substitute, the buffer being separate and distinct from the storage array and each storage location of the storage array.

In accordance with one or more aspects of the present disclosure the storage array of the refrigerated chamber is at least one from (1) a sample container holding plate, (2) a sample container holding tray, (3) a plate holder, (4) a tray holder, (5) a sample holding rack, (6) a sample holding box, and (7) a portable or fixed store rack disposed for holding one or more of a sample container holding plate, a sample container holding tray, a plate holder, a tray holder, a sample holding rack, and a sample holding box in stored array.

In accordance with one or more aspects of the present disclosure the labware devices are portable to and from the storage array and insertable into and removable from each storage location of the storage array, and is at least one from (1) a sample container holding plate, (2) a sample container holding tray, (3) a plate holder, (4) a tray holder, (5) a sample holding rack, (6) a sample holding box, and (7) a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

In accordance with one or more aspects of the present disclosure the labware units are at least one from a vial, tube, cassette, and a microwell plate.

In accordance with one or more aspects of the present disclosure the labware units are portable specimen sample containers of unitary construction.

In accordance with one or more aspects of the present disclosure the labware devices are each a portable labware unit holder for at least one labware unit.

In accordance with one or more aspects of the present disclosure more than one simulacrum labware substitute are shaped so that the at least one simulacrum labware substitute, held in a storage location and another simulacrum labware substitute held in another storage location communicate with each other over a thermal transfer link so as to cooperate in sustainment of thermal equilibrium across each other storage location of the storage array separate from refrigeration of the refrigerated chamber.

In accordance with one or more aspects of the present disclosure the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

In accordance with one or more aspects of the present disclosure different simulacrum labware substitutes having at least one of which has different thermal mass than another, are disposed in storage locations of the storage array to provide a predetermined thermal inertia profile, or gradient in at least one axis over the storage array.

In accordance with one or more aspects of the present disclosure different simulacrum labware substitutes having at least one of which has different thermal mass than another, are disposed in storage locations of the storage array to provide a predetermined thermal inertia profile, or gradient in at least one axis relative to a predetermined storage location holding the at least one simulacrum labware substitute.

In accordance with one or more aspects of the present disclosure the method further comprises preloading the at least one simulacrum labware substitute in the storage location.

In accordance with one or more aspects of the present disclosure a method for controlling a temperature within a temperature controlled sample specimen laboratory storage system is provided. The temperature controlled sample specimen laboratory storage system is configured to store sample specimens disposed in one or more of labware units and labware devices and including a refrigerated chamber with a storage array therein having predetermined storage locations, each of the storage locations are configured for holding therein at least one of the one or more of the labware units and labware devices per storage location at a refrigerated thermal equilibrium. The method comprises:

providing at least one simulacrum labware substitute, each of the at least one simulacrum labware substitute having a predetermined thermal mass analogous with that of each of the at least one of the one or more labware units and labware devices, and the at least one simulacrum labware substitute and the at least one of the one or more of the labware units and the labware devices are interchangeable at each storage location for holding the one or more of the labware units and the labware devices so that the at least one of the one or more labware units and labware devices and the at least one simulacrum labware substitute are swapped for each other at the storage location; and disposing the at least one simulacrum labware substitute in at least one of the predetermined storage locations within the storage array so that the at least one simulacrum labware substitute held in each storage location throughout the storage array effects predetermined thermal inertia bias so as to maintain refrigerated thermal equilibrium, via thermal inertia bias, throughout the storage array separate and distinct from refrigeration of the refrigerated chamber.

In accordance with one or more aspects of the present disclosure the at least one simulacrum labware substitute held in each storage location throughout the storage array effects thermal bias response, about a thermal equilibrium of the refrigerated chamber, so as to maintain the refrigerated thermal equilibrium throughout the storage array.

In accordance with one or more aspects of the present disclosure the predetermined storage locations define a predetermined capacity of one or more of labware units storage and labware devices storage of the storage array, for the storage array of a predetermined area, and the predetermined capacity of the one or more of the labware units storage and the labware devices storage of the storage array, of predetermined area, is unconstrained by the at least one simulacrum labware substitute held in swap for at least one of the one or more labware units and labware devices in the storage location.

In accordance with one or more aspects of the present disclosure the method further comprises balancing addition and removal of the at least one simulacrum labware substitute from the storage array, with addition and removal of a corresponding one of the one or more of the labware units and labware devices from the storage array, wherein balancing is effected with the automated transport.

In accordance with one or more aspects of the present disclosure the addition and removal of the at least one simulacrum labware substitute is balanced with the addition and removal of the corresponding one of the one or more of the labware units and labware devices so as to maximize fill of the storage array throughout the storage array.

In accordance with one or more aspects of the present disclosure the method further comprises automatically engaging and swapping, at each storage location and with a gripper of the automated transport, the one or more of the labware units and labware devices with the at least one simulacrum labware substitute, and vice versa, so that fill of the storage array is substantially constant, throughout the storage array, with addition and removal of the one or more of the labware units and labware devices from each storage location.

In accordance with one or more aspects of the present disclosure the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

In accordance with one or more aspects of the present disclosure the at least one simulacrum labware substitute effects the refrigerated thermal equilibrium from within a storage location of the predetermined storage locations holding the at least one simulacrum labware substitute in swap for holding the one or more of the labware units and labware devices in the storage location.

In accordance with one or more aspects of the present disclosure the method further comprises a buffer, in the refrigerated chamber, for the at least one simulacrum labware substitute, the buffer being separate and distinct from the storage array and each storage location of the storage array.

In accordance with one or more aspects of the present disclosure the storage array of the refrigerated chamber is at least one from (1) a sample container holding plate, (2) a sample container holding tray, (3) a plate holder, (4) a tray holder, (5) a sample holding rack, (6) a sample holding box, and (7) a portable or fixed store rack disposed for holding one or more of a sample container holding plate, a sample container holding tray, a plate holder, a tray holder, a sample holding rack, and a sample holding box in stored array.

In accordance with one or more aspects of the present disclosure the labware devices are portable to and from the storage array and insertable into and removable from each storage location of the storage array, and is at least one from (1) a sample container holding plate, (2) a sample container holding tray, (3) a plate holder, (4) a tray holder, (5) a sample holding rack, (6) a sample holding box, and (7) a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

In accordance with one or more aspects of the present disclosure the labware units are at least one from a vial, tube, cassette, and a microwell plate.

In accordance with one or more aspects of the present disclosure the labware units are portable specimen sample containers of unitary construction.

In accordance with one or more aspects of the present disclosure the labware devices are each a portable labware unit holder for at least one labware unit.

In accordance with one or more aspects of the present disclosure more than one simulacrum labware substitute are shaped so that the at least one simulacrum labware substitute, held in a storage location and another simulacrum labware substitute held in another storage location communicate with each other over a thermal transfer link so as to cooperate in sustainment of the refrigerated thermal equilibrium across each other storage location of the storage array separate from refrigeration of the refrigerated chamber.

In accordance with one or more aspects of the present disclosure the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

In accordance with one or more aspects of the present disclosure different simulacrum labware substitutes having at least one of which has different thermal mass than another, are disposed in storage locations of the storage array to provide a predetermined thermal inertia profile, or gradient in at least one axis over the storage array.

In accordance with one or more aspects of the present disclosure different simulacrum labware substitutes having at least one of which has different thermal mass than another, are disposed in storage locations of the storage array to provide a predetermined thermal inertia profile, or gradient in at least one axis relative to a predetermined storage location holding the at least one simulacrum labware substitute.

In accordance with one or more aspects of the present disclosure the method further comprises preloading the at least one simulacrum labware substitute in the storage location.

In accordance with one or more aspects of the present disclosure a temperature control sample specimen simulacrum labware unit for a temperature controlled sample specimen labware store having sample specimen labware unit storage locations is provided. The simulacrum labware unit comprising:

an exterior case configured for storage at each of the sample specimen labware unit storage locations, the exterior case being sized and shaped commensurate with size and shape of a corresponding sample specimen labware unit so that the temperature control sample specimen simulacrum labware unit and the corresponding sample specimen labware unit are interchangeable with each other at each of the sample specimen labware unit storage locations; and a thermal mass held in the exterior case, that forms a temperature control with the temperature control sample specimen simulacrum labware unit in the temperature controlled sample specimen labware store;

wherein the exterior case and thermal mass provide the temperature control sample specimen simulacrum labware unit with a predetermined thermal characteristic so that the temperature control sample specimen simulacrum labware unit forms a substitute for the corresponding sample specimen labware unit at each storage location.

In accordance with one or more aspects of the present disclosure at each of the sample specimen labware unit storage locations, the temperature control sample specimen simulacrum labware unit and the corresponding sample specimen labware unit are fungible with respect to the predetermined thermal characteristic, and are swapped as like kind.

In accordance with one or more aspects of the present disclosure the predetermined thermal characteristic of the temperature control sample specimen simulacrum labware unit has a first thermal mass characteristic that is an analogue for a second thermal mass characteristic of the corresponding sample specimen labware unit/device.

In accordance with one or more aspects of the present disclosure the first thermal mass characteristic and the second thermal mass characteristic are the same in character and in magnitude.

In accordance with one or more aspects of the present disclosure the thermal mass is one or more of a metal, a fluid, and a semi-solid material.

In accordance with one or more aspects of the present disclosure the metal comprises one or more of aluminum, stainless steel, bismuth, and a metal alloy mass.

In accordance with one or more aspects of the present disclosure the fluid comprises a phase change material.

In accordance with one or more aspects of the present disclosure the phase change material comprises one or more of a wax and a substance, that is non-aqueous and non-saline, that stabilizes temperature by melting or solidifying to absorb or release heat whenever temperatures are warmer or cooler than the melting point of the substance.

In accordance with one or more aspects of the present disclosure the semi-solid material comprises a gel.

In accordance with one or more aspects of the present disclosure the gel comprises dimethyl sulfoxide.

In accordance with one or more aspects of the present disclosure the exterior case is permanently sealed.

In accordance with one or more aspects of the present disclosure the exterior case and the thermal mass therein form a substantially solid unit so that the temperature control sample specimen simulacrum unit is free of cavities.

In accordance with one or more aspects of the present disclosure the temperature control sample specimen simulacrum unit is configured so as to prevent insertion of a sample specimen therein.

In accordance with one or more aspects of the present disclosure the exterior case and the thermal mass are configured so that the temperature control sample specimen simulacrum unit is configured for extended and stable room temperature storage.

In accordance with one or more aspects of the present disclosure a set of temperature control sample specimen simulacrum labware units for a temperature controlled sample specimen labware store having sample specimen labware unit storage locations is provided. The set of simulacrum labware units comprising:

more than one temperature control sample specimen simulacrum labware units, each temperature control sample specimen simulacrum labware unit having:

an exterior case configured for storage at each of the sample specimen labware unit storage locations, the exterior case being sized and shaped commensurate with size and shape of a corresponding sample specimen labware unit so that the temperature control sample specimen simulacrum labware unit and the corresponding sample specimen labware unit are interchangeable with each other at each of the sample specimen labware unit storage locations; and a thermal mass held in the exterior case, that forms a temperature control with the temperature control sample specimen simulacrum labware unit in the temperature controlled sample specimen labware store;

wherein the exterior case and thermal mass provide the temperature control sample specimen simulacrum labware unit with a predetermined thermal characteristic so that the temperature control sample specimen simulacrum labware unit forms a substitute for the corresponding sample specimen labware unit at each storage location.

In accordance with one or more aspects of the present disclosure at each of the sample specimen labware unit storage locations, each of the temperature control sample specimen simulacrum labware units and the corresponding sample specimen labware units are fungible with respect to the predetermined thermal characteristic, and are swapped as like kind.

In accordance with one or more aspects of the present disclosure the predetermined thermal characteristic of the temperature control sample specimen simulacrum labware unit has a first thermal mass characteristic that is an analogue for a second thermal mass characteristic of the corresponding sample specimen labware unit.

In accordance with one or more aspects of the present disclosure the first thermal mass characteristic and the second thermal mass characteristic are the same in character and in magnitude.

In accordance with one or more aspects of the present disclosure each temperature control sample specimen simulacrum labware unit in the set of temperature control sample specimen simulacrum labware unit has a same predetermined thermal characteristic.

In accordance with one or more aspects of the present disclosure the thermal mass is one or more of a metal, a fluid, and a semi-solid material.

In accordance with one or more aspects of the present disclosure the metal comprises one or more of aluminum, stainless steel, bismuth, and a metal alloy mass.

In accordance with one or more aspects of the present disclosure the fluid comprises a phase change material.

In accordance with one or more aspects of the present disclosure the phase change material comprises one or more of a wax and a substance, that is non-aqueous and non-saline, that stabilizes temperature by melting or solidifying to absorb or release heat whenever temperatures are warmer or cooler than the melting point of the substance.

In accordance with one or more aspects of the present disclosure the semi-solid material comprises a gel.

In accordance with one or more aspects of the present disclosure the gel comprises dimethyl sulfoxide.

In accordance with one or more aspects of the present disclosure each temperature control sample specimen simulacrum labware unit in the set of temperature control sample specimen simulacrum labware unit has a same composition.

In accordance with one or more aspects of the present disclosure the exterior case is permanently sealed.

In accordance with one or more aspects of the present disclosure the exterior case and the thermal mass therein form a substantially solid unit so that the temperature control sample specimen simulacrum unit is free of cavities.

In accordance with one or more aspects of the present disclosure the temperature control sample specimen simulacrum unit is configured so as to prevent insertion of a sample specimen therein.

In accordance with one or more aspects of the present disclosure the exterior case and the thermal mass are configured so that the temperature control sample specimen simulacrum unit is configured for extended and stable room-temperature storage.

In accordance with one or more aspects of the present disclosure a temperature control sample specimen simulacrum labware device for a temperature controlled sample specimen labware store having sample specimen labware device storage locations is provided. The simulacrum labware device comprising:

an exterior case configured for storage at each of the sample specimen labware device storage locations, the exterior case being sized and shaped commensurate with size and shape of a corresponding sample specimen labware device so that the temperature control sample specimen simulacrum labware device and the corresponding sample specimen labware device are interchangeable with each other at each of the sample specimen labware device storage locations; and a thermal mass held in the exterior case, that forms a temperature control with the temperature control sample specimen simulacrum labware device in the temperature controlled sample specimen labware store;

wherein the exterior case and thermal mass provide the temperature control sample specimen simulacrum labware device with a predetermined thermal characteristic so that the temperature control sample specimen simulacrum labware device forms a substitute for the corresponding sample specimen labware device at each storage location.

In accordance with one or more aspects of the present disclosure at each of the sample specimen labware device storage locations, the temperature control sample specimen simulacrum labware device and the corresponding sample specimen labware device are fungible with respect to the predetermined thermal characteristic, and are swapped as like kind.

In accordance with one or more aspects of the present disclosure the predetermined thermal characteristic of the temperature control sample specimen simulacrum labware device has a first thermal mass characteristic that is an analogue for a second thermal mass characteristic of the corresponding sample specimen labware device.

In accordance with one or more aspects of the present disclosure the first thermal mass characteristic and the second thermal mass characteristic are the same in character and in magnitude.

In accordance with one or more aspects of the present disclosure the thermal mass is one or more of a metal, a fluid, and a semi-solid material.

In accordance with one or more aspects of the present disclosure the metal comprises one or more of aluminum, stainless steel, bismuth, and a metal alloy mass.

In accordance with one or more aspects of the present disclosure the fluid comprises a phase change material.

In accordance with one or more aspects of the present disclosure the phase change material comprises one or more of a wax and a substance, that is non-aqueous and non-saline, that stabilizes temperature by melting or solidifying to absorb or release heat whenever temperatures are warmer or cooler than the melting point of the substance.

In accordance with one or more aspects of the present disclosure the semi-solid material comprises a gel.

In accordance with one or more aspects of the present disclosure the gel comprises dimethyl sulfoxide.

In accordance with one or more aspects of the present disclosure the exterior case is permanently sealed.

In accordance with one or more aspects of the present disclosure the exterior case and the thermal mass therein form a substantially solid unit so that the temperature control sample specimen simulacrum device is free of cavities.

In accordance with one or more aspects of the present disclosure the temperature control sample specimen simulacrum device is configured so as to prevent insertion of a sample specimen therein.

In accordance with one or more aspects of the present disclosure the exterior case and the thermal mass are configured so that the temperature control sample specimen simulacrum device is configured for extended and stable room temperature storage.

In accordance with one or more aspects of the present disclosure a set of temperature control sample specimen simulacrum labware devices for a temperature controlled sample specimen labware store having sample specimen labware device storage locations is provided. The set of simulacrum labware devices comprising:

more than one temperature control sample specimen simulacrum labware devices, each temperature control sample specimen simulacrum labware device having:

an exterior case configured for storage at each of the sample specimen labware device storage locations, the exterior case being sized and shaped commensurate with size and shape of a corresponding sample specimen labware device so that the temperature control sample specimen simulacrum labware device and the corresponding sample specimen labware device are interchangeable with each other at each of the sample specimen labware device storage locations; and a thermal mass held in the exterior case, that forms a temperature control with the temperature control sample specimen simulacrum labware device in the temperature controlled sample specimen labware store;

wherein the exterior case and thermal mass provide the temperature control sample specimen simulacrum labware device with a predetermined thermal characteristic so that the temperature control sample specimen simulacrum labware device forms a substitute for the corresponding sample specimen labware device at each storage location.

In accordance with one or more aspects of the present disclosure at each of the sample specimen labware device storage locations, each of the temperature control sample specimen simulacrum labware devices and the corresponding sample specimen labware devices are fungible with respect to the predetermined thermal characteristic, and are swapped as like kind.

In accordance with one or more aspects of the present disclosure the predetermined thermal characteristic of the temperature control sample specimen simulacrum labware device has a first thermal mass characteristic that is an analogue for a second thermal mass characteristic of the corresponding sample specimen labware device.

In accordance with one or more aspects of the present disclosure the first thermal mass characteristic and the second thermal mass characteristic are the same in character and in magnitude.

In accordance with one or more aspects of the present disclosure each temperature control sample specimen simulacrum labware device in the set of temperature control sample specimen simulacrum labware device has a same predetermined thermal characteristic.

In accordance with one or more aspects of the present disclosure the thermal mass is one or more of a metal, a fluid, and a semi-solid material.

In accordance with one or more aspects of the present disclosure the metal comprises one or more of aluminum, stainless steel, bismuth, and a metal alloy mass.

In accordance with one or more aspects of the present disclosure the fluid comprises a phase change material.

In accordance with one or more aspects of the present disclosure the phase change material comprises one or more of a wax and a substance, that is non-aqueous and non-saline, that stabilizes temperature by melting or solidifying to absorb or release heat whenever temperatures are warmer or cooler than the melting point of the substance.

In accordance with one or more aspects of the present disclosure the semi-solid material comprises a gel.

In accordance with one or more aspects of the present disclosure the gel comprises dimethyl sulfoxide.

In accordance with one or more aspects of the present disclosure each temperature control sample specimen simulacrum labware device in the set of temperature control sample specimen simulacrum labware device has a same composition.

In accordance with one or more aspects of the present disclosure the exterior case is permanently sealed.

In accordance with one or more aspects of the present disclosure the exterior case and the thermal mass therein form a substantially solid unit so that the temperature control sample specimen simulacrum device is free of cavities.

In accordance with one or more aspects of the present disclosure the temperature control sample specimen simulacrum device is configured so as to prevent insertion of a sample specimen therein.

In accordance with one or more aspects of the present disclosure the exterior case and the thermal mass are configured so that the temperature control sample specimen simulacrum device is configured for extended and stable room-temperature storage.

It should be understood that the foregoing description is only illustrative of the aspects of the present disclosure. Various alternatives and modifications can be devised by those skilled in the art without departing from the aspects of the present disclosure. Accordingly, the aspects of the present disclosure are intended to embrace all such alternatives, modifications and variances that fall within the scope of any claims appended hereto. Further, the mere fact that different features are recited in mutually different dependent or independent claims does not indicate that a combination of these features cannot be advantageously used, such a combination remaining within the scope of the aspects of the present disclosure.

What is claimed is:

1. A temperature controlled sample specimen laboratory storage system for storing sample specimens disposed in one or more of labware units and labware devices, the temperature controlled sample specimen laboratory storage system comprising:

a refrigerated chamber with a storage array therein having predetermined storage locations, each configured for holding therein at least one of the one or more of the labware units and labware devices per storage location, the predetermined storage locations defining a predetermined capacity of one or more of labware unit storage and labware device storage of the storage array, where the storage array has a predetermined area, each labware unit is configured to contain a corresponding sample specimen, and each labware device is configured to hold one or more of the labware units; and at least one simulacrum labware substitute that is specimenless, and in contrast to each labware unit the at least one simulacrum labware substitute is configured so as to be incapable of containing sample specimen, and in contrast to each labware device the at least one simulacrum labware substitute is configured so as to be incapable of holding a labware unit so as to be incapable of laboratory functions, the at least one simulacrum labware substitute having a predetermined characteristic that simulates and represents each of the thermal characteristics of a corresponding one of the one or more of the labware units and labware devices so that the at least one simulacrum labware substitute and the corresponding one of the one or more of the labware units and labware devices are interchangeable with respect to each storage location holding the at least one simulacrum labware substitute swapped for the corresponding one of the one or more of the labware units and labware devices; and wherein the at least one simulacrum labware substitute held in the storage location is disposed within the storage array so that the predetermined capacity of the one or more of the labware unit storage and the labware device storage of the storage array, of the predetermined area, is unconstrained by the at least one simulacrum labware substitute held in the storage location.

2. The temperature controlled sample specimen laboratory storage system of claim 1, wherein the predetermined capacity of the one or more of the labware unit storage and the labware device storage of the storage array remains a maximum capacity independent of the at least one simulacrum labware substitute held in the storage location.

3. The temperature controlled sample specimen laboratory storage system of claim 1, wherein the predetermined characteristic of the at least one simulacrum labware substitute has a first thermal mass characteristic that is an analogue for a second thermal mass characteristic of the respective one of the one or more of the interchangeable labware units and labware devices.

4. The temperature controlled sample specimen laboratory storage system of claim 1, wherein the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

5. The temperature controlled sample specimen laboratory storage system of claim 1, wherein the at least one simulacrum labware substitute is configured and disposed within the storage array so that the at least one simulacrum labware substitute held in each storage location effects predetermined thermal inertia bias sustaining thermal equilibrium across each other storage location of the storage array separate from refrigeration of the refrigerated chamber.

6. The temperature controlled sample specimen laboratory storage system of claim 1, wherein the at least one simulacrum labware substitute effects thermal equilibrium from within the storage location holding the at least one simulacrum labware substitute in swap for holding the one or more of the labware units and labware devices in the storage location.

7. The temperature controlled sample specimen laboratory storage system of claim 1, further comprising a buffer, in the refrigerated chamber, for the at least one simulacrum labware substitute, the buffer being separate and distinct from the storage array and each storage location of the storage array.

8. The temperature controlled sample specimen laboratory storage system of claim 1, wherein the storage array of the refrigerated chamber is at least one from:

- a sample container holding plate,
- a sample container holding tray,
- a plate holder,
- a tray holder,
- a sample holding rack,
- a sample holding box, and
- a portable or fixed store rack disposed for holding one or more of a sample container holding plate, a sample container holding tray, a plate holder, a tray holder, a sample holding rack, and a sample holding box in stored array.

9. The temperature controlled sample specimen laboratory storage system of claim 1, wherein the labware devices are portable to and from the storage array and insertable into and removable from each storage location of the storage array, and is at least one from:

- a sample container holding plate,
- a sample container holding tray,
- a plate holder,
- a tray holder,
- a sample holding rack,
- a sample holding box, and
- a portable store rack disposed for holding one or more of a sample container holding plate, a sample container holding tray, a plate holder, a tray holder, a sample holding rack, and a sample holding box in stored array within the portable store rack and insertable into and removable from store rack storage locations arrayed in the refrigerated chamber.

10. The temperature controlled sample specimen laboratory storage system of claim 1, wherein the labware units are at least one from a vial, tube, cassette, and a microwell plate.

11. The temperature controlled sample specimen laboratory storage system of claim 1, wherein the labware units are portable specimen sample containers of unitary construction.

12. The temperature controlled sample specimen laboratory storage system of claim 1, wherein the labware devices are each a portable labware unit holder for at least one labware unit.

13. The temperature controlled sample specimen laboratory storage system of claim 1, wherein more than one simulacrum labware substitute are shaped so that the at least one simulacrum labware substitute, held in a storage location and another simulacrum labware substitute held in another storage location communicate with each other over a thermal transfer link so as to cooperate in sustainment of thermal equilibrium across each other storage location of the storage array separate from refrigeration of the refrigerated chamber.

14. The temperature controlled sample specimen laboratory storage system of claim 1, wherein the at least one simulacrum labware substitute of a corresponding labware unit or labware device, is selectable from other different interchangeable simulacrum labware substitutes each of which corresponding to the corresponding labware unit or labware device, each of the different simulacrum labware substitutes having a different thermal mass characteristic.

15. The temperature controlled sample specimen laboratory storage system of claim 1, wherein the at least one simulacrum labware substitute is loaded in the storage location.

16. A temperature controlled sample specimen laboratory storage system for storing sample specimens disposed in one or more of labware units and labware devices, the temperature controlled sample specimen laboratory storage system comprising:

- a refrigerated chamber with a storage array therein having predetermined storage locations, each configured for holding therein at least one of the one or more of the labware units and labware devices per storage location, the predetermined storage locations defining a predetermined capacity of one or more of labware unit storage and labware device storage of the storage array, where the storage array has a predetermined area, each labware unit is configured to contain a corresponding sample specimen, and each labware device is configured to hold one or more of the labware units; and
- at least one simulacrum labware substitute that is specimenless, and in contrast to each labware unit the at least one simulacrum labware substitute is configured so as to be incapable of containing sample specimen, and in contrast to each labware device the at least one simulacrum labware substitute is configured so as to be incapable of holding a labware unit so as to be incapable of laboratory functions, the at least one simulacrum labware substitute having a predetermined characteristic that simulates and represents each of the thermal characteristics of a corresponding one of the one or more of the labware units and labware devices so that the at least one simulacrum labware substitute and the corresponding one of the one or more of the labware units and labware devices are interchangeable at each storage location for holding the one or more of the labware units and labware devices so that the one or more of the labware units and labware devices and the at least one simulacrum labware substitute are swapped for each other at the storage location; and
- wherein disposition of the at least one simulacrum labware substitute held in the storage location is unconstrained throughout the storage array so that the predetermined capacity of the one or more of the labware unit storage and the labware device storage of the storage array, of a predetermined area, is maintained at a maximum.

17. The temperature controlled sample specimen laboratory storage system of claim 16, wherein the predetermined capacity of the one or more of the labware unit storage and the labware device storage of the storage array remains a maximum capacity independent of the at least one simulacrum labware substitute held in the storage location.

18. The temperature controlled sample specimen laboratory storage system of claim 16, wherein the predetermined characteristic of the at least one simulacrum labware substitute has a first thermal mass characteristic that is an analogue for a second thermal mass characteristic of the respective one of the one or more of the interchangeable labware units and labware devices.

19. The temperature controlled sample specimen laboratory storage system of claim 18, wherein the first thermal mass characteristic and the second thermal mass characteristic are the same in character and in magnitude.

20. The temperature controlled sample specimen laboratory storage system of claim 16, wherein the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

21. The temperature controlled sample specimen laboratory storage system of claim 20, wherein the addition and removal of the at least one simulacrum labware substitute is balanced with the addition and removal of the corresponding one of the one or more of the labware units and labware devices so as to maximize fill of the storage array throughout the storage array.

22. The temperature controlled sample specimen laboratory storage system of claim 20, wherein the automated transport has a gripper configured to automatically engage and swap, at each storage location, the one or more of the labware units and labware devices with the at least one simulacrum labware substitute, and vice versa, so that fill of the storage array is substantially constant, throughout the storage array, with addition and removal of the one or more of the labware units and labware devices from each storage location.

23. The temperature controlled sample specimen laboratory storage system of claim 22, wherein the gripper has a holding location for holding the one or more of the labware units and labware devices held by the gripper of the automated transport, and a spare holding location for holding the at least one simulacrum labware substitute held by the gripper and swapping, at each storage location, the one or more of the labware units and labware devices and the simulacrum labware substitute with each other.

24. A temperature controlled sample specimen laboratory storage system for storing sample specimens disposed in one or more of labware units and labware devices, the temperature controlled sample specimen laboratory storage system comprising:

a refrigerated chamber with a storage array therein having predetermined storage locations, each of the storage locations are configured for holding therein at least one of the one or more of the labware units and labware devices per storage location at a refrigerated thermal equilibrium, each labware unit is configured to contain a corresponding sample specimen, and each labware device is configured to hold one or more of the labware units; and at least one simulacrum labware substitute that is specimenless, and in contrast to each labware unit the at least one simulacrum labware substitute is configured so as to be incapable of containing sample specimen, and in contrast to each labware device the at least one simulacrum labware substitute is configured so as to be incapable of holding a labware unit so as to be incapable of laboratory functions, the at least one simulacrum labware substitute, each of the at least one simulacrum labware substitute having a predetermined thermal mass analogous with that of each of the at least one of the one or more labware units and labware devices, and the at least one simulacrum labware substitute and the at least one of the one or more of the labware units and the labware devices are interchangeable at each storage location for holding the one or more of the labware units and the labware devices so that the at least one of the one or more labware units and labware devices and the at least one simulacrum labware substitute are swapped for each other at the storage location; and wherein the at least one simulacrum labware substitute held in the storage location is disposed within the storage array so that the at least one simulacrum labware substitute held in each storage location throughout the storage array effects predetermined thermal inertia bias so as to maintain the refrigerated thermal equilibrium, via thermal inertia bias, throughout the storage array separate and distinct from refrigeration of the refrigerated chamber.

25. The temperature controlled sample specimen laboratory storage system of claim 24, wherein the at least one simulacrum labware substitute held in each storage location throughout the storage array effects thermal bias response, about a thermal equilibrium of the refrigerated chamber, so as to maintain the refrigerated thermal equilibrium throughout the storage array.

26. The temperature controlled sample specimen laboratory storage system of claim 25, wherein the predetermined storage locations define a predetermined capacity of one or more of labware units storage and labware devices storage of the storage array, for the storage array of a predetermined area, and the predetermined capacity of the one or more of the labware units storage and the labware devices storage of the storage array, of predetermined area, is unconstrained by the at least one simulacrum labware substitute held in swap for at least one of the one or more labware units and labware devices in the storage location.

27. The temperature controlled sample specimen laboratory storage system of claim 24, wherein the temperature controlled sample specimen laboratory storage system is automated, and further comprises an automated transport, the automated transport being configured to balance addition and removal of the at least one simulacrum labware substitute from the storage array, with addition and removal of a corresponding one of the one or more of the labware units and labware devices from the storage array.

28. The temperature controlled sample specimen laboratory storage system of claim 27, wherein the addition and removal of the at least one simulacrum labware substitute is balanced with the addition and removal of the corresponding one of the one or more of the labware units and labware devices so as to maximize fill of the storage array throughout the storage array.

29. The temperature controlled sample specimen laboratory storage system of claim 24, wherein the at least one simulacrum labware substitute effects the refrigerated thermal equilibrium from within a storage location of the predetermined storage locations holding the at least one simulacrum labware substitute in swap for holding the one or more of the labware units and labware devices in the storage location.

30. The temperature controlled sample specimen laboratory storage system of claim 24, wherein the labware units are at least one from a vial, tube, cassette, and a microwell plate.

31. The temperature controlled sample specimen laboratory storage system of claim 24, wherein the labware units are portable specimen sample containers of unitary construction.

32. The temperature controlled sample specimen laboratory storage system of claim 24, wherein the labware devices are each a portable labware unit holder for at least one labware unit.

* * * * *